(12) United States Patent
Birch et al.

(10) Patent No.: US 8,188,092 B2
(45) Date of Patent: May 29, 2012

(54) SUBSTITUTED PYRAZINES AS DGAT-1 INHIBITORS

(75) Inventors: Alan Martin Birch, Macclesfield (GB); Roger John Butlin, Macclesfield (GB); Leonie Campbell, Macclesfield (GB); Clive Green, Macclesfield (GB); Andrew Leach, Macclesfield (GB); Michael James Waring, Macclesfield (GB); Paul Michael Murray, Bristol (GB); Per Olof Ryberg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/818,187

(22) Filed: Jun. 18, 2010

(65) Prior Publication Data
US 2010/0324068 A1 Dec. 23, 2010

Related U.S. Application Data

(60) Provisional application No. 61/218,539, filed on Jun. 19, 2009.

(51) Int. Cl.
*A61K 31/4965* (2006.01)
(52) U.S. Cl. .................... 514/255.06; 544/406
(58) Field of Classification Search ............ 514/255.06; 544/406
See application file for complete search history.

(56) References Cited

U.S. PATENT DOCUMENTS

| | | | |
|---|---|---|---|
| 3,245,989 A | 4/1966 | Palazzo | |
| 4,983,731 A | 1/1991 | Wagner et al. | |
| 5,491,172 A | 2/1996 | Lee et al. | |
| 6,608,185 B1 | 8/2003 | Omura et al. | |
| 6,624,185 B2 | 9/2003 | Glombik et al. | |
| 7,138,414 B2 | 11/2006 | Schoenafinger et al. | |
| 7,453,010 B2 | 11/2008 | Bovy et al. | |
| 7,749,997 B2 | 7/2010 | Birch et al. | |
| 7,795,283 B2 | 9/2010 | Birch et al. | |
| 2002/0183384 A1 | 12/2002 | Cornicelli et al. | |
| 2003/0072757 A1 | 4/2003 | Farese et al. | |
| 2004/0102432 A1 | 5/2004 | Sanganee et al. | |
| 2005/0070545 A1 | 3/2005 | Fox et al. | |
| 2007/0123504 A1 | 5/2007 | Bolin et al. | |
| 2007/0155832 A1 | 7/2007 | Haeberlein et al. | |
| 2007/0249620 A1 | 10/2007 | Kurata et al. | |
| 2008/0090876 A1 | 4/2008 | Cheng et al. | |
| 2008/0096874 A1 | 4/2008 | Birch et al. | |
| 2008/0306059 A1 | 12/2008 | Birch et al. | |
| 2008/0312282 A1 | 12/2008 | Judd et al. | |
| 2009/0048258 A1 | 2/2009 | Ogino et al. | |
| 2009/0093497 A1 | 4/2009 | Bolin et al. | |
| 2009/0197926 A1 | 8/2009 | Birch et al. | |
| 2009/0209602 A1 | 8/2009 | Butlin et al. | |
| 2009/0215779 A1 | 8/2009 | Butlin et al. | |
| 2009/0275620 A1 | 11/2009 | Butlin et al. | |
| 2009/0298853 A1 | 12/2009 | Bauer et al. | |
| 2010/0029727 A1 | 2/2010 | Johnstone et al. | |
| 2010/0160397 A1 | 6/2010 | Birch et al. | |
| 2010/0173958 A1 | 7/2010 | Bennett et al. | |
| 2010/0184813 A1 | 7/2010 | Birch et al. | |
| 2010/0311737 A1 | 12/2010 | Birch et al. | |
| 2010/0317653 A1 | 12/2010 | Birch et al. | |

FOREIGN PATENT DOCUMENTS

| | | |
|---|---|---|
| DE | 10223273 | 12/2003 |
| EP | 1236468 | 9/2002 |
| EP | 1541563 | 6/2005 |
| EP | 1661889 | 5/2006 |
| EP | 1760071 | 3/2007 |
| JP | 2002284741 | 3/2002 |
| JP | 2004/067635 | 3/2004 |
| JP | 2005/206492 | 8/2005 |
| JP | 2007/131584 | 5/2007 |
| JP | 2007/191471 | 8/2007 |

(Continued)

OTHER PUBLICATIONS

Adcock et al., "Electronic effect of the tricyanomethyl group by carbon-13 and fluorine-19 NMR: nature of aryl fluorine-19 NMR polar field effects in the benzene and naphthalene ring systems" Journal of Organic Chemistry 44 (17): 3004-3017 (1979).

(Continued)

*Primary Examiner* — James O Wilson
*Assistant Examiner* — Douglas M Willis

(57) ABSTRACT

DGAT-1 inhibitor compounds of formula (I), pharmaceutically-acceptable salts and pro-drugs thereof are described, together with pharmaceutical compositions, processes for making them and their use in treating, for example, obesity

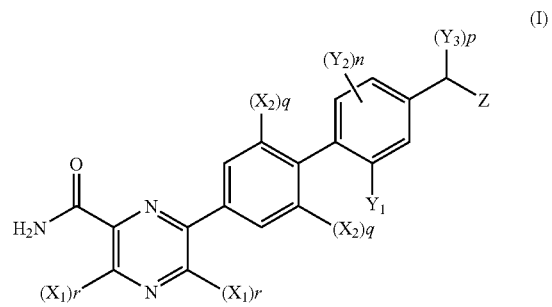

wherein, for example, r is 0 or 1 and $X_1$ is linear (1-3C)alkyl;
q is 0 or 1 and $X_2$ is fluoro, chloro or (1-3C)alkyl;
$Y_1$ is selected from fluoro, chloro, bromo, cyano, (1-3C)alkyl and (1-2C)alkoxy;
n is 0, 1 or 2 and $Y_2$ is fluoro, chloro or (1-3C)alkyl;
p is 0, 1 or 2 and $Y_3$ is (1-3C)alkyl or forms a (3-5C)cycloalkyl ring;
Z is carboxy or —$CONHSO_2Me$ or —$CONRbRc$ wherein Rb and Rc are independently selected, for example, from hydrogen and (1-4C)alkyl or Rb and Rc are linked so as to form a morpholine ring or a (4-6C)heterocyclic ring and when Z is —CONRbRc the Rb and Rc groups may be optionally substituted by carboxy.

13 Claims, No Drawings

FOREIGN PATENT DOCUMENTS

| | | |
|---|---|---|
| JP | 2010132590 | 6/2010 |
| WO | WO 94/26702 | 11/1994 |
| WO | WO 00/58491 | 10/2000 |
| WO | WO 00/72832 | 12/2000 |
| WO | WO 02/20484 | 3/2002 |
| WO | WO 03/099772 | 12/2003 |
| WO | WO 2004/007455 | 1/2004 |
| WO | WO 2004/017920 | 3/2004 |
| WO | WO 2004/032882 | 4/2004 |
| WO | WO 2004/047755 | 6/2004 |
| WO | WO 2004/062601 | 7/2004 |
| WO | WO 2004/089927 | 10/2004 |
| WO | WO 2004/100881 | 11/2004 |
| WO | WO 2004/110350 | 12/2004 |
| WO | WO 2005/013907 | 2/2005 |
| WO | WO 2005/027892 | 3/2005 |
| WO | WO 2005/037826 | 4/2005 |
| WO | 2005/044250 | 5/2005 |
| WO | WO 2005/044250 | 5/2005 |
| WO | WO 2005/046670 | 5/2005 |
| WO | WO 2005/072740 | 8/2005 |
| WO | WO 2006/004200 | 1/2006 |
| WO | WO 2006/019020 | 2/2006 |
| WO | WO 2006/044775 | 4/2006 |
| WO | WO 2006/054370 | 5/2006 |
| WO | 2006/064189 | 6/2006 |
| WO | WO 2006/064189 | 6/2006 |
| WO | WO 2006/082010 | 8/2006 |
| WO | WO 2006/082952 | 8/2006 |
| WO | WO 2006/113919 | 10/2006 |
| WO | WO 2006/120125 | 11/2006 |
| WO | 2006/134317 | 12/2006 |
| WO | WO 2006/134317 | 12/2006 |
| WO | WO 2007/007588 | 1/2007 |
| WO | WO 2007/016538 | 2/2007 |
| WO | WO 2007/060140 | 5/2007 |
| WO | 2007/071966 | 6/2007 |
| WO | WO 2007/071966 | 6/2007 |
| WO | WO 2007/074753 | 7/2007 |
| WO | WO 2007/124337 | 11/2007 |
| WO | WO 2007/126957 | 11/2007 |
| WO | WO 2007/137103 | 11/2007 |
| WO | WO 2007/137107 | 11/2007 |
| WO | 2007/138304 | 12/2007 |
| WO | 2007/138311 | 12/2007 |
| WO | 2007/141502 | 12/2007 |
| WO | 2007/141517 | 12/2007 |
| WO | 2007/141538 | 12/2007 |
| WO | 2007/141545 | 12/2007 |
| WO | 2007/144571 | 12/2007 |
| WO | WO 2007/138304 | 12/2007 |
| WO | WO 2007/138311 | 12/2007 |
| WO | WO 2007/141502 | 12/2007 |
| WO | WO 2007/141517 | 12/2007 |
| WO | WO 2007/141538 | 12/2007 |
| WO | WO 2007/141545 | 12/2007 |
| WO | WO 2007/144571 | 12/2007 |
| WO | WO 2008/011130 | 1/2008 |
| WO | WO 2008/011131 | 1/2008 |
| WO | WO 2008/039007 | 4/2008 |
| WO | WO 2008/039008 | 4/2008 |
| WO | WO 2008/040651 | 4/2008 |
| WO | WO 2008/046216 | 4/2008 |
| WO | WO 2008/048991 | 4/2008 |
| WO | WO 2008/058402 | 5/2008 |
| WO | WO 2008/067257 | 6/2008 |
| WO | WO 2008/073865 | 6/2008 |
| WO | WO 2008/099221 | 8/2008 |
| WO | WO 2008/129319 | 10/2008 |
| WO | WO 2008/134690 | 11/2008 |
| WO | WO 2008/134693 | 11/2008 |
| WO | WO 2008/141976 | 11/2008 |
| WO | WO 2008/148840 | 12/2008 |
| WO | WO 2008/148849 | 12/2008 |
| WO | WO 2008/148851 | 12/2008 |
| WO | WO 2008/148868 | 12/2008 |
| WO | WO 2008/154642 | 12/2008 |
| WO | WO 2009/009041 | 1/2009 |
| WO | WO 2009/011285 | 1/2009 |
| WO | 2009/024821 | 2/2009 |
| WO | WO 2009/016462 | 2/2009 |
| WO | WO 2009/024821 | 2/2009 |
| WO | WO 2009/037222 | 3/2009 |
| WO | WO 2009/040410 | 4/2009 |
| WO | WO 2009/071483 | 6/2009 |
| WO | 2009/081195 | 7/2009 |
| WO | WO 2009/081195 | 7/2009 |
| WO | WO 2009/112445 | 9/2009 |
| WO | WO 2009/119534 | 10/2009 |
| WO | WO 2009/126624 | 10/2009 |
| WO | WO 2009/126861 | 10/2009 |
| WO | WO 2009/137938 | 11/2009 |
| WO | WO 2010/007046 | 1/2010 |
| WO | WO 2010/017040 | 2/2010 |
| WO | WO 2010/023609 | 3/2010 |
| WO | WO 2010/048149 | 4/2010 |
| WO | WO 2010/056496 | 5/2010 |
| WO | WO 2010/056506 | 5/2010 |
| WO | WO 2010/059602 | 5/2010 |
| WO | WO 2010/059606 | 5/2010 |
| WO | WO 2010/059611 | 5/2010 |
| WO | WO 2010/065310 | 6/2010 |
| WO | WO 2010/070343 | 6/2010 |
| WO | WO 2010/077861 | 7/2010 |
| WO | WO 2010/083280 | 7/2010 |
| WO | WO 2010/084979 | 7/2010 |
| WO | WO 2010/086820 | 8/2010 |
| WO | WO 2010/089685 | 8/2010 |
| WO | WO 2010/089686 | 8/2010 |
| WO | WO 2010/091041 | 8/2010 |
| WO | WO 2010/095766 | 8/2010 |
| WO | WO 2010/107765 | 9/2010 |
| WO | WO 2010/107768 | 9/2010 |
| WO | WO 2010/108051 | 9/2010 |
| WO | WO 2010/122968 | 10/2010 |

OTHER PUBLICATIONS

Anderson et al. "Identification of a Form of Acyl-CoA:Cholesterol Acyltransferase Specific to Liver and Intestine in Nonhuman Primates" J Biol Chem 273(41):26747-26754 (1998).

Birch et al. "Discovery of a Potent, Selective, and Orally Efficacious Pyrimidinooxazinyl Bicyclooctaneacetic Acid Diacylglycerol Acyltransferase-1 Inhibitor" J. Med. Chem. 52(6):1558-1568 (2009).

Birch et al. "DGAT1 inhibitors as anti-obesity and anti-diabetic agents" Current Opinion in Drug Discovery and Development 13(4):489-96 (Jul. 2010).

Brown and Goldstein "Lipoprotein metabolism in the macrophage: implications for cholesterol deposition in atherosclerosis" Annu Rev Biochem. 52:223-261 (1983).

Burnett and Huff "Avasimibe Pfizer" Curr Opin Investig Drugs 3(9):1328-1333 (2002).

CAPLUS RN 404032-15-1, retrieved from CAPLUS on Jul. 17, 2009.

Cases et al. "ACAT-2, A Second Mammalian Acyl-CoA:Cholesterol Acyltransferase" J Biol Chem 273(41):26755-26764 (1998).

Cases et al. "Cloning of DGAT2, a Second Mammalian Diacylglycerol Acyltransferase, and Related Family Members" J. Biol. Chem. 276(42):38870-38876 (2001).

Cases et al. "Identification of a gene encoding an acyl CoA:diacylglycerol acyltransferase, a key enzyme in triacylglycerol synthesis" Proc Natl Acad Sci U S A. 95(22):13018-13023 (1998).

Chang et al. "Molecular cloning and functional expression of human acyl-coenzyme A:cholesterol acyltransferase cDNA in mutant Chinese hamster ovary cells" J. Biol. Chem. 268(28):20747-20755 (1993).

Chen et al. "Increased Insulin and Leptin Sensitivity in Mice Lacking ACYL COA: Diacylglycerol Acyltransferase 1" Journal of Clinical Investigation 109(8):1049-1055 (2002).

Chen et al. "Inhibition of Triglyceride Synthesis as a Treatment Strategy for Obesity: Lessons From DGAT1-Deficient Mice" Arteriosclerosis, Thrombosis, and Vascular Biology 25(3): 482-486 (2005).

Chen et al. "Obesity resistance and enhanced glucose metabolismin mice transplanted with white adipose tissue lacking acyl CoA:diacylglycerol acyltransferase 1" J. Clin. Invest. 111(11):1715-1722 (2003).

Coleman "Diacylglycerol acyltransferase and monoacylglycerol acyltransferase from liver and intestine" Methods in Enzymology 209:98-104 (1992).

Field and Salome "Effect of dietary fat saturation, cholesterol and cholestyramine on acyl-CoA: cholesterol acyltransferase activity in rabbit intestinal microsomes" Biochimica et Biophysica Acta 712(3):557-570 (1982).

Hoffman et al. "Synthesis and evaluation of 2-pyridinone derivatives as HIV-1-specific reverse transcriptase inhibitors. 4. 3[2-(Benzoxazol-2-yl)ethyl]-5-ethyl-6-methylpyridin-2(1H)-one and analogs" Journal of Medicinal Chemistry 36(8):953-966 (1993).

Hubbard et al. "Antisense and small-molecule modulation of diacylglycerol acyltransferase" Expert Opinion on Therapeutic Patents 17(11): 1331-1339 (2007).

Insull Jr. et al. "Efficacy and short-term safety of a new ACAT inhibitor, avasimibe, on lipids, lipoproteins, and apolipoproteins, in patients with combined hyperlipidemia" Atherosclerosis 157(1):137-144 (2001).

Lehner and Kuksis "Biosynthesis of triacylglycerols" Prog Lipid Res. 35(2):169-201 (1996).

Oelkers et al. "Characterization of Two Human Genes Encoding Acyl Coenzyme A:Cholesterol Acyltransferase-related Enzymes" J Biol Chem 273(41):26765-26771 (1998).

Robertson et al. "Preclinical Safety Evaluation of Avasimibe in Beagle Dogs: An ACAT Inhibitor with Minimal Adrenal Effects" Toxicological Sciences 2001 US, 59(2):324-334 (2001).

Sawhney et al. "Synthesis of some 2-(5-substituted 1,3,4-oxadiazol-2-yl)-, 2-(5-substituted 1,3,4-thiadiazol-2-yl)- and 2-(3-mercapto-4-substituted-4H-1,2,4-triazol-5 -yl)- benzimidazoles as potential antiinflammatory agents" Indian Journal of Chemistry Section B, 30B:407-412 (1991).

Smith et al. "Obesity resistance and multiple mechanisms of triglyceride synthesis in mice lacking DGAT" Nature Genetics 25:87-90 (2000).

Yen et al. "Identification of a gene encoding MGAT1, a monoacylglycerol acyltransferase" Proc Natl Acad Sci U S A. 99(13):8512-8517 (2002).

Yen et al. "Thematic Review Series: Glycerolipids. DGAT enzymes and triacylglycerol biosynthesis" Journal of Lipid Research 49: 2283-2301 (2008).

Zammit et al. "Diacylglycerol acyltransferases: Potential roles as pharmacological targets" Pharmacology & Therapeutics 118(3):295-302 (2008).

Zhao et al. "Validation of diacyl glycerolacyltransferase I as a novel target for the treatment of obesity and dyslipidemia using a potent and selective small molecule inhibitor" J. Med. Chem. 51:380-383 (2008).

B.K. Hubbard et al., "Antisense and small-molecule modulation of diacylglycerol acyltransferase", Expert Opinion on Therapeutic Patents 17(11): 1331-1339 (2007).

International Search Report and Written Opinion dated Aug. 12, 2010 for PCT GB2010/051003.

International Search Report and Written Opinion for PCT/GB2008/051199, dated Mar. 31, 2009.

S. Birtles et al., "Pharmacological effect of DGAT1 inhibition on food intake and post-prandial lipaemia-determination of the mechanism of action", Poster, Cheshire, UK, Mar. 24-26, 2010.

S. Birtles et al., "Pharmacological effect of DGAT1 inhibition on food intake and post-prandial lipaemia-determination of the mechanism of action", Abstract, Cheshire, UK, Mar. 24-26, 2010.

B.M. Fox et al., "Discovery of pyrrolopyridazines as novel DGAT1 inhibitors", Bioorg. Med. Chem. Lett. 20: 6030-6033 (2010).

W. Langhans et al., "Fatty acid oxidation in the energostatic control of eating—a new idea", Appetite 51: 446-451 (2008).

Y. Nakada et al., "Novel acyl coenzyme A (CoA): Diacylglycerol acyltransferase-1 inhibitors: Synthesis and biological activities of diacylethylenediamine derivatives", Bioorg. Med. Chem. 18: 2785-2795 (2010).

SUBSTITUTED PYRAZINES AS DGAT-1 INHIBITORS

This application claims the benefit under 35 U.S.C. §119 (e) of Application No. 61/218,539 (US) filed on Jun. 19, 2009, which is herein incorporated by reference in its entirety.

The present invention relates to compounds which inhibit acetyl CoA(acetyl coenzyme A):diacylglycerol acyltransferase (DGAT1) activity, processes for their preparation, pharmaceutical compositions containing them as the active ingredient, methods for the treatment of disease states associated with DGAT1 activity, to their use as medicaments and to their use in the manufacture of medicaments for use in the inhibition of DGAT1 in warm-blooded animals such as humans. In particular this invention relates to compounds useful for the treatment of type II diabetes, insulin resistance, impaired glucose tolerance and obesity in warm-blooded animals such as humans, more particularly to the use of these compounds in the manufacture of medicaments for use in the treatment of type II diabetes, insulin resistance, impaired glucose tolerance and obesity in warm-blooded animals such as humans.

Acyl CoA:diacylglycerol acyltransferase (DGAT) is found in the microsomal fraction of cells. It catalyzes the final reaction in the glycerol phosphate pathway, considered to be the main pathway of triglyceride synthesis in cells by facilitating the joining of a diacylglycerol with a fatty acyl CoA, resulting in the formation of triglyceride. Although it is unclear whether DGAT is rate-limiting for triglyceride synthesis, it catalyzes the only step in the pathway that is committed to producing this type of molecule [Lehner & Kuksis (1996) Biosynthesis of triacylglycerols. Prog. Lipid Res. 35: 169-201].

Two DGAT genes have been cloned and characterised (DGAT1 and DGAT2). Both of the encoded proteins catalyse the same reaction although they share no sequence homology. The DGAT1 gene was identified from sequence database searches because of its similarity to acyl CoA:cholesterol acyltransferase (ACAT) genes. [Cases et al (1998) Identification of a gene encoding an acyl CoA:diacylglycerol acyltransferase, a key enzyme in triacylglycerol synthesis. Proc. Natl. Acad. Sci. USA 95: 13018-13023]. DGAT1 activity has been found in many mammalian tissues, including adipocytes.

Because of the previous lack of molecular probes, little is known about the regulation of DGAT1. DGAT1 is known to be significantly up-regulated during adipocyte differentiation.

Studies in gene knockout mice have indicated that modulators of the activity of DGAT1 would be of value in the treatment of type II diabetes and obesity. DGAT1 knockout (Dgat1$^{-/-}$) mice, are viable and capable of synthesizing triglycerides, as evidenced by normal fasting serum triglyceride levels and normal adipose tissue composition. Dgat1$^{-/-}$ mice have less adipose tissue than wild-type mice at baseline and are resistant to diet-induced obesity. Metabolic rate is ~20% higher in Dgat1$^{-/-}$ mice than in wild-type mice on both regular and high-fat diets [Smith et al (2000) Obesity resistance and multiple mechanisms of triglyceride synthesis in mice lacking DGAT. Nature Genetics 25: 87-90]. Increased physical activity in Dgat1$^{-/-}$ mice partially accounts for their increased energy expenditure. The Dgat1$^{-/-}$ mice also exhibit increased insulin sensitivity and a 20% increase in glucose disposal rate. Leptin levels are 50% decreased in the Dgat1$^{-/-}$ mice in line with the 50% decrease in fat mass.

When Dgat1$^{-/-}$ mice are crossed with ob/ob mice, these mice exhibit the ob/ob phenotype [Chen et al (2002) Increased insulin and leptin sensitivity in mice lacking acyl CoA:diacylglycerol acyltransferase J. Clin. Invest. 109:1049-1055] indicating that the Dgat1$^{-/-}$ phenotype requires an intact leptin pathway. When Dgat1$^{-/-}$ mice are crossed with Agouti mice a decrease in body weight is seen with normal glucose levels and 70% reduced insulin levels compared to wild type, agouti or ob/ob/Dgat1$^{-/-}$ mice.

Transplantation of adipose tissue from Dgat1$^{-/-}$ mice to wild type mice confers resistance to diet-induced obesity and improved glucose metabolism in these mice [Chen et al (2003) Obesity resistance and enhanced glucose metabolism in mice transplanted with white adipose tissue lacking acyl CoA:diacylglycerol acyltransferase J. Clin. Invest. 111: 1715-1722].

Various International Applications disclose compounds which inhibit DGAT-1, for example WO 2006/064189 describes certain oxadiazole compounds which inhibit DGAT-1. However, there remains a need for further DGAT-1 inhibitors possessing desirable properties, such as, for example, pharmaco-kinetic/dynamic and/or physico-chemical and/or toxicological profiles.

Accordingly, the present invention provides a compound of formula (I), or a pharmaceutically-acceptable salt, or pro-drug thereof,

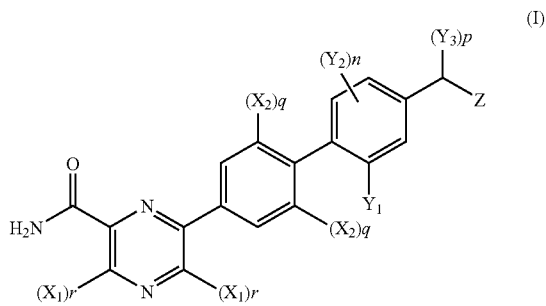

wherein each r is independently 0 or 1 and each $X_1$ is independently selected from linear (1-3C)alkyl, (2-3C)alkenyl, (2-3C)alkynyl, (1-2C)alkoxy, methoxymethyl, amino and cyano;
each q is independently 0 or 1 and each $X_2$ is independently selected from fluoro, chloro, bromo, amino, cyano, (1-3C)alkyl, (2-3C)alkenyl, (2-3C)alkynyl and (1-2C)alkoxy;
$Y_1$ is selected from fluoro, chloro, bromo, cyano, (1-3C)alkyl and (1-2C)alkoxy;
n is 0, 1 or 2 and each $Y_2$ is independently selected from fluoro, chloro, bromo, cyano, hydroxy, (1-3C)alkyl and (1-2C)alkoxy;
p is 0, 1 or 2 and each $Y_3$ is independently (1-3C)alkyl or when p is 2 each $Y_3$ may also link to form a (3-5C)cycloalkyl ring;
Z is carboxy or a group Q selected from —CONHSO$_2$Me or one of the following rings,

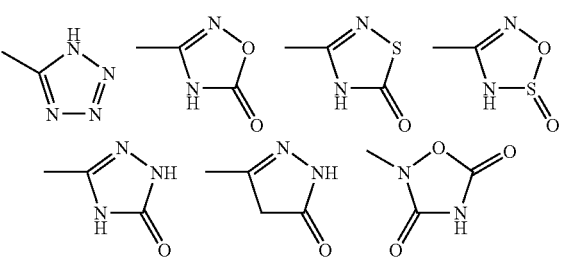

-continued

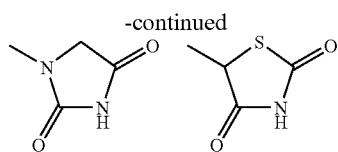

or Z is —CONRbRc wherein Rb and Rc are independently selected from hydrogen, (1-4C)alkyl and (1-4C)alkoxyethyl or Rb and Rc are linked so as to form a morpholine ring or a (4-6C)heterocyclic ring, and when Z is —CONRbRc the (1-4C)alkyl group and morpholine or (4-6C)heterocyclic rings that may be formed may be optionally substituted on an available carbon atom by carboxy or a group Q;
and wherein any carbon atom in a linear (1-3C)alkyl, (1-3C) alkyl or (1-2C)alkoxy containing group defined above may be optionally substituted by up to 3 fluoro atoms.

For the avoidance of doubt when p=2 the group

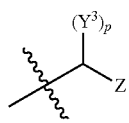

denotes the group

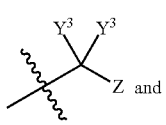

when p=0 the group

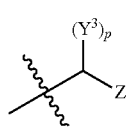

denotes the group

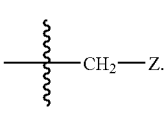

A further feature is any of the claims or embodiments herein with the proviso that any of the specific Examples herein, or a pharmaceutically-acceptable salt of any of these, are individually disclaimed.

A further feature of the invention is a compound of formula (I) comprising a carboxylic acid mimic or bioisosteres of the group Z. As used herein, the reference to carboxylic acid mimic or bioisostere includes groups as defined in The Practice of Medicinal Chemistry, Wermuth C. G. Ed.: Academic Press: New York, 1996, p 203 which is incorporated herein by reference. Particular examples of such groups include —SO$_3$H, —S(O)$_2$NHR$^{13}$, —S(O)$_2$NHC(O)R$^{13}$, —CH$_2$S(O)$_2$R$^{13}$, —C(O)NHS(O)$_2$R$^{13}$, —C(O)NHOH, —C(O)NHCN, —CH(CF$_3$)OH, C(CF$_3$)$_2$OH, —P(O)(OH)$_2$ and groups of sub-formula (a)-(i') below

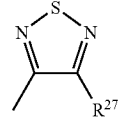 (a)

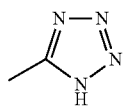 (b)

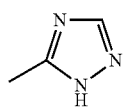 (c)

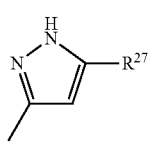 (d)

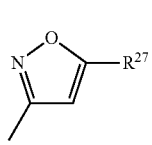 (e)

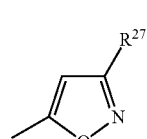 (f)

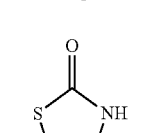 (g)

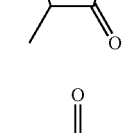 (h)

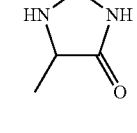 (i)

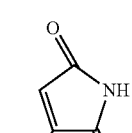 (j)

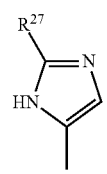

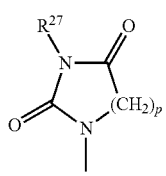 (k)
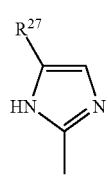 (l)
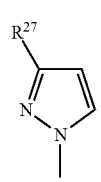 (m)
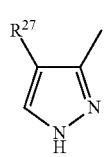 (n)
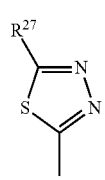 (o)
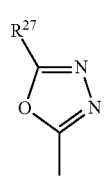 (p)
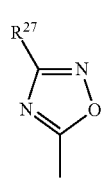 (q)
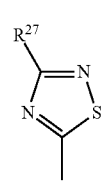 (r)
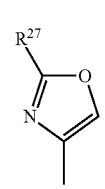 (s)
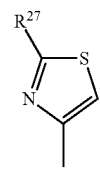 (t)
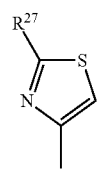 (u)
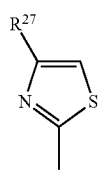 (v)
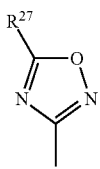 (w)
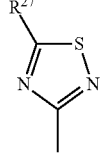 (x)
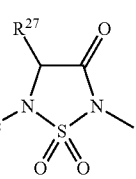 (y)
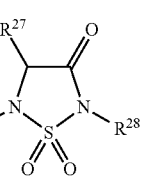 (z)
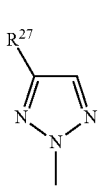 (a′)
(b′)

(c')
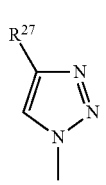

(d')
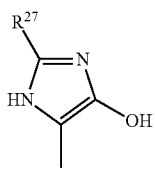

(e')
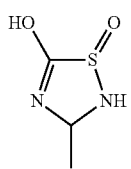

(f')
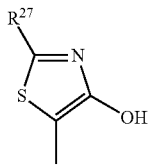

(g')
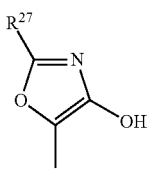

(h')
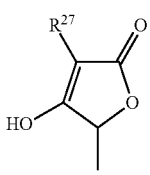

(i')
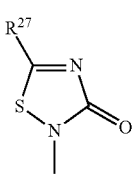

where p in sub-formula (k) is 1 or 2, $R^{27}$ and $R^{28}$ are independently selected from hydrogen, hydroxy, (1-6C)alkoxy, thiol, (1-6C)alkylthio, —C(O)$R^{29}$, —S(O)$R^{30}$, —SO$_2$$R^{31}$, —NR$^{32}$R$^{33}$, —NHCN, halogen and trihalomethyl, where $R^{29}$, $R^{30}$ and $R^{31}$ are —OR$^{34}$, (1-6C)alkyl, —NR$^{32}$R$^{33}$ or trihalomethyl, $R^{32}$ and $R^{33}$ are independently selected from hydrogen, (1-6C)alkyl, —SO$_2$$R^{34}$ and —COR$^{35}$, where $R^{35}$ is (1-6C)alkyl or trihalomethyl, and $R^{34}$ is hydrogen, (1-6C)alkyl or trihalomethyl and $R^{13}$ is selected from hydrogen, (1-6C)alkyl, hydroxy, halo, amino, cyano, ((1-3C)alkyl)CONH—, carboxy, (1-6C)alkoxy, (1-6C)alkoxycarbonyl, carbamoyl, N-((1-6C)alkyl)carbamoyl, halo((1-6C)alkyl) (such as trifluoromethyl), (1-6C)alkylsulphonyl or (1-6C)alkylsulphinyl. Particular examples of $R^{27}$ or $R^{28}$ are hydroxy.

Particular carboxylic acid mimic or bioisosteres are a tetrazole group of sub-formula (b) and —C(O)NHS(O)$_2$Me.

In this specification the term "alkyl" includes both straight and branched chain alkyl groups, unless otherwise stated, and references to individual alkyl groups such as "propyl" are specific for the straight chain version only. An analogous convention applies to other generic terms. Unless otherwise stated the term "alkyl" advantageously refers to chains with 1-10 carbon atoms, suitably from 1-6 carbon atoms, preferably 1-4 carbon atoms.

In this specification the term "alkoxy" means an alkyl group as defined hereinbefore linked to an oxygen atom.

Particular values include for linear (1-3C)alkyl, methyl, ethyl and propyl; for (1-4C)alkyl, methyl, ethyl, propyl and butyl; for (2-3C)alkenyl, ethenyl; for (2-3C)alkynyl, ethynyl; for (1-2C)alkoxy, methoxy and ethoxy; for (1-4C)alkoxy, methoxy, ethoxy and propoxy; for —CONRbRc, —CONH$_2$ and —CONHMe.

Particular values include for any carbon atom in a linear (1-3C)alkyl, (1-2C)alkoxy, (1-4C)alkyl or (1-4C)alkoxy group that may be optionally substituted by up to 3 fluoro atoms, a group such as, for example, trifluoromethyl, difluoromethyl, difluoromethoxy or trifluoromethoxy.

For the avoidance of doubt it is to be understood that where in this specification a group is qualified by 'hereinbefore defined' or 'defined hereinbefore' the said group encompasses the first occurring and broadest definition as well as each and all of the particular definitions for that group.

If not stated elsewhere, suitable optional substituents for a particular group are those as stated for similar groups herein.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as Group (I) (alkali metal) salt, Group (II) (alkaline earth) metal salt, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions.

Other suitable pharmaceutically-acceptable salts are mentioned in, for example, Berge et al. (J. Pharm. Sci., 1977, 66, 1-19) and/or Handbook of Pharmaceutical Salts: Properties, Selection and Use by Stahl and Wermuth (Wiley-VCH, 2002), each of which is incorporated herein by reference.

A feature of the invention relates to a compound of the invention, such as any one of the Examples, in the free acid or free base form or as a pharmaceutically acceptable salt thereof. Such forms may be prepared by standard techniques.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings (for example those for group Q) within this specification can represent only one of the possible tautomeric forms. It is to be understood that the invention encompasses any tautomeric form which inhibits DGAT1 activity and is not to be limited merely to any one tautomeric form utilised within the formulae drawings.

Pro-drugs of compounds of formula (I), and salts thereof, are also within the scope of the invention.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984),
each of which is incorporated herein by reference.

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

Particular prodrugs are an ester of a carboxy group selected from a (1-6C)alkyl ester, a (1-6C)alkoxymethyl ester, a (1-6C)alkanoyloxymethyl ester, a phthalidyl ester, a (3-8C)cycloalkoxycarbonyloxy(1-6C)alkyl ester, a 1,3-dioxolan-2-ylmethyl ester, a (1-6C)alkoxycarbonyloxyethyl ester, an aminocarbonylmethyl ester and a mono- or di-N-((1-6C)alkyl) version of an aminocarbonylmethyl ester.

Particular prodrugs are (1-4C)alkyl esters of the carboxylic acid in compounds of formula (I).

It will be appreciated by those skilled in the art that certain compounds of formula (I) contain asymmetrically substituted carbon and/or sulfur atoms, and accordingly may exist in, and be isolated in, optically-active and racemic forms. Some compounds of formula (I) may exhibit polymorphism. It is to be understood that the present invention encompasses any racemic, optically-active, polymorphic or stereoisomeric form, or mixtures thereof, which form possesses properties useful in the inhibition of DGAT1 activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DGAT1 activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DGAT1 activity.

As stated before, a range of compounds are provided that have good DGAT1 inhibitory activity. They have good physical and/or pharmacokinetic properties in general. The compounds possess particular, desirable pharmaceutical and/or physical and/or pharmacokinetic/dynamic and/or toxicological properties and/or selective activity for DGAT1.

In one embodiment there is provided a compound as claimed in any one of the claims, or a pharmaceutically-acceptable salt, or pro-drug thereof, wherein the pyrazine is substituted on an available carbon atom by one or two linear (1-3C)alkyl substituents, in particular methyl, and in particular dimethyl.

Particular values of substituents in compounds of formula (I) are as follows (such values may be used where appropriate with any of the other values, definitions, claims or embodiments defined hereinbefore or hereinafter), for example the skilled man will understand that, for example, the particular values (2) and (3) below may be incorporated into any of the claims or embodiments herein to define a scope in which the pyrazine is dimethyl-pyrazine . . .

(1) $X_1$ is linear (1-3C)alkyl;
(2) $X_1$ is methyl or ethyl, particularly methyl;
(3) each $X_1$ is methyl
(4) r is 1;
(5) r is 2
(6) r is 2 and each $X_1$ is linear (1-3C)alkyl;
(7) r is 2 and each $X_1$ is methyl;
(8) q is 0 or 1;
(9) one q is 0 and one q is 1;
(10) $X_2$ is bromo, fluoro or chloro;
(11) $X_2$ is fluoro or chloro;
(12) $X_2$ is fluoro;
(13) $Y_1$ is fluoro, chloro, methyl or trifluoromethyl;
(14) $Y_1$ is fluoro or chloro;
(15) $Y_1$ is chloro;
(16) n is 0 or 1;
(17) n is 0;
(18) $Y_2$ is fluoro, chloro or (1-3C)alkyl;
(19) $Y_2$ is fluoro, chloro or methyl;
(20) p is 0 or 1;
(21) p is 2;
(22) $Y_3$ is fluoro, chloro, (1-3C)alkyl or a cyclopropyl or cyclobutyl ring (formed from two $Y_3$ groups);
(23) $Y_3$ is (1-3C)alkyl or a cyclopropyl or cyclobutyl ring (formed from two $Y_3$ groups);
(24) p is 2 and $Y_3$ forms a (3-5C)cycloalkyl ring;
(25) Z is carboxy or —CONRbRc or

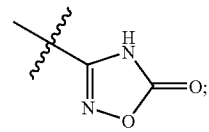

(26) Z is carboxy or —CONRbRc;
(27) Z is —CONRbRc;

(28) Z is carboxy;
(29) Rb is (1-4C)alkyl, optionally substituted by carboxy;
(30) Rc is hydrogen or (1-4C)alkyl;
(31) Rc is hydrogen or methyl, for example hydrogen;
(32) any carbon atom in a linear (1-3C)alkyl, (1-3C)alkyl or (1-2C)alkoxy containing group in $X_2$, $Y_2$ or $Y_1$ may be optionally substituted by up to 3 fluoro atoms;
(33) Z is —CONRbRc and Rb and Rc are linked so as to form a morpholine ring or a (4-6C)heterocyclic ring, such as an azetidine ring;
(34) Z is —CONRbRc and Rb and Rc are linked so as to form a morpholine ring or a (4-6C)heterocyclic ring, such as a piperidine ring;
(35) Z is —CONRbRc and the (1-4C)alkyl group and the morpholine or (4-6C)heterocyclic rings that may be formed by Rb and Rc are substituted on an available carbon atom by a carboxy group Q.
(36) Z is —CONRbRc and the (1-4C)alkyl group and the morpholine or (4-6C)heterocyclic rings that may be formed by Rb and Rc are substituted on an available carbon atom by a carboxy group or a group Q.

Thus, in another embodiment is a compound of formula (I), or a pharmaceutically-acceptable salt, or pro-drug thereof, wherein each r is 1 and each $X_1$ is methyl;
each q is independently 0 or 1 and each $X_2$ is independently selected from fluoro and chloro; $Y_1$ is selected from fluoro, chloro, and (1-3C)alkyl;
n is 0 or 1 and each $Y_2$ is independently selected from fluoro, chloro and (1-3C)alkyl;
p is 0, 1 or 2 and $Y_3$ is independently (1-3C)alkyl or when p is 2 each $Y_3$ may also link to form a (3-5C)cycloalkyl ring;
Z is carboxy or a group Q selected from —CONHSO$_2$Me or one of the following rings,

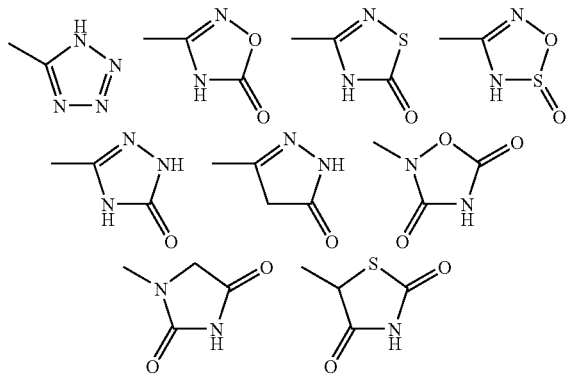

or Z is —CONRbRc wherein Rb and Rc are independently selected from hydrogen, (1-4C)alkyl and (1-4C)alkoxyethyl or Rb and Rc are linked so as to form a morpholine ring or a (4-6C)heterocyclic ring, and when Z is —CONRbRc the (1-4C)alkyl group and morpholine or (4-6C)heterocyclic rings that may be formed may be optionally substituted on an available carbon atom by carboxy or a group Q;
and wherein any carbon atom in a linear (1-3C)alkyl, (1-3C)alkyl or (1-2C)alkoxy containing group defined above may be optionally substituted by up to 3 fluoro atoms.

In another embodiment is a compound of formula (I), or a pharmaceutically-acceptable salt, or pro-drug thereof, wherein
each r is 1 and each $X_1$ is (1-3C)alkyl, for example methyl;
each q is independently 0, 1 or 2 and each $X_2$ is independently selected from fluoro and chloro;
$Y_1$ is selected from fluoro, chloro, and (1-3C)alkyl optionally substituted by upto three fluorine atoms;
n is 0 or 1 and each $Y_2$ is independently selected from fluoro, chloro and (1-3C)alkyl;
p is 0, 1 or 2 and $Y_3$ is independently (1-3C)alkyl or when p is 2 each $Y_3$ may also link to form a (3-5C)cycloalkyl ring;
Z is carboxy or a group Q selected from one of the following rings,

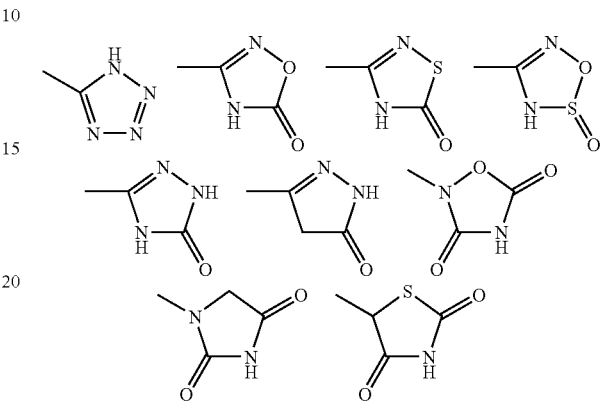

for example Z is carboxy, or a group

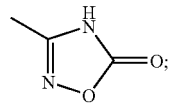

or Z is —CONRbRc wherein Rb and Rc are independently selected from hydrogen and (1-4C)alkyl or Rb and Rc are linked so as to form a (4-6C)heterocyclic ring, for example piperidine,
and when Z is —CONRbRc the (1-4C)alkyl group and (4-6C) heterocyclic ring that may be formed may be optionally substituted on an available carbon atom by carboxy.

In another embodiment there is provided a compound of formula (I) as defined in any of the embodiments herein wherein a pro-drug for Z as carboxy is a (1-6C)alkyl ester.

A further feature is any of the scopes defined herein with the proviso that specific Examples, such as Example 1, 2, 3, 4 etc. are individually disclaimed.

Further particular compounds of the invention are each of the Examples, each of which provides a further independent aspect of the invention. In further aspects, the present invention also comprises any particular compounds of the Examples or a pharmaceutically-acceptable salt thereof (such as, for example, a sodium, magnesium, tert-butylammonium, tris(hydroxymethyl)methylammonium, triethanolammonium, diethanolammonium, ethanolammonium, methylethanolammonium, diethylammonium or nicotinamide salt).

In a further aspect, the present invention also comprises any particular isomers of compounds of the Examples, or a pharmaceutically-acceptable salt of any of these.

A compound of formula (I) and its salts may be prepared by any process known to be applicable to the preparation of chemically related compounds. Such processes, when used to prepare a compound of the formula (I), or a pharmaceutically-acceptable salt thereof, are provided as a further feature of the invention.

In a further aspect the present invention also provides that the compounds of the formula (I) and salts thereof, can be prepared by the following processes, the processes of the Examples and analogous processes (wherein all variables are as hereinbefore defined for a compound of formula (I) unless otherwise stated) and thereafter if necessary any protecting groups can be removed and/or an appropriate salt formed. Any defined carboxylic acid groups may be replaced as appropriate by a mimic or bioisostere thereof, in particular groups defined as Q herein.

Variables shown in the schemes are defined or can be interpreted in the context of the variants described herein for the compounds of the invention. Analogous chemistry to that shown in the schemes and Examples may be used to prepare other ring variants and linking group options within the scope of the invention.

Also included as an aspect of the invention are the compounds obtainable by any of the processes or Examples described herein.

Process A

By modifying a substituent in, or introducing a substituent into, another compound of formula (I). Suitable methods for converting substituents into other substituents are known in the art; for example, an acid group may be converted into an amide group.

Compounds of formula (I) where, for example, Z is an acylsulfonamide group or Z is a tetrazole or oxadiazolone may be prepared from the corresponding carboxylic acid. The tetrazole may be introduced early in the synthetic route via an amide (which, for primary amides, may be converted to the nitrile by standard methods) which is then in turn converted into a tetrazole by reaction with azide. The tetrazole may be carried through the rest of the synthesis in protected form, e.g. N-benzylated or N-(2-cyanoethyl)ated. Similarly, the nitriles described above may be converted early in the synthetic sequence to an oxadiazolone by standard methods.

Process B

As described in the following processes (wherein the variables are appropriately as defined in any of the claims, embodiments or Examples herein), Suzuki coupling of an appropriate triflate, iodo-, bromo- or chloro-substituted aromatic compound can be performed with a suitably substituted intermediate boron-containing compound using standard methods with a suitable palladium catalyst, such as 1,1'-bis (diphenylphosphino)-ferrocenedichloro-palladium(II).

Process B1

Suzuki coupling of an appropriate triflate, iodo-, bromo- or chloro-substituted pyrazine derivative (IV) with a suitably substituted intermediate boron-containing compound of formula (II).

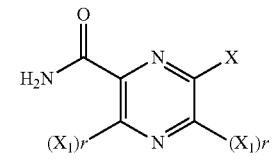

(IV)

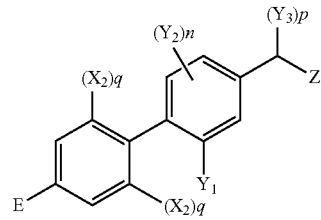

(II)

X in formula (IV) represents a leaving group such as triflate, iodo-, bromo- or chloro and E in formula (II) represents a boronic acid (—B(OH)$_2$) or a derivative thereof such as a boronate ester (—B(OR)$_2$ wherein R here is (1-4C)alkyl) or a cyclic boronate ester, such as pinacolato borane (4,4,5,5-tetramethyl-1,3,2-dioxaborolane).

Alternatively a Suzuki coupling of an appropriate triflate, iodo-, bromo- or chloro-pyrazine ester (III), particularly bromo- or chloro-pyrazine ethyl ester (III), can be used followed by removal of the protecting group by basic hydrolysis (for example of a methyl or ethyl ester). The pyrazine acid is then converted to the corresponding primary carboxamide by reaction with ammonia in the presence of a coupling agent, for example PyBOP.

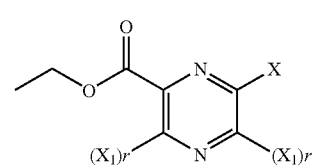

(III)

X in formula (III) represents a leaving group such as triflate, iodo-, bromo- or chloro.

An illustration of Process B1 is provided in the scheme below (for the dimethyl pyrazine variant) in which (Tf)$_2$O or PhNTf$_2$ may be used.

Scheme B1: Illustrative reaction scheme

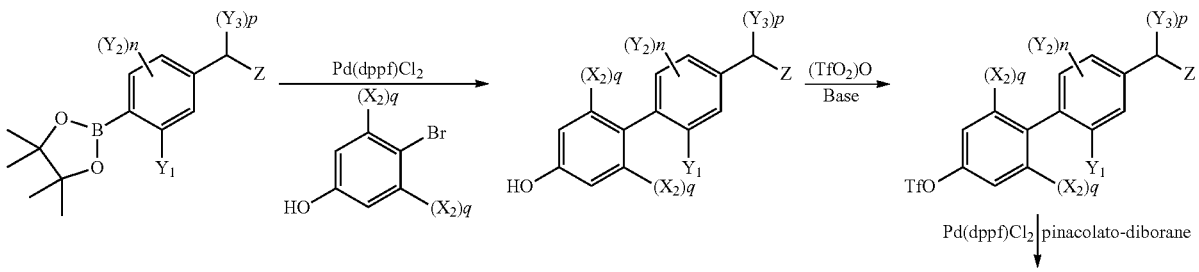

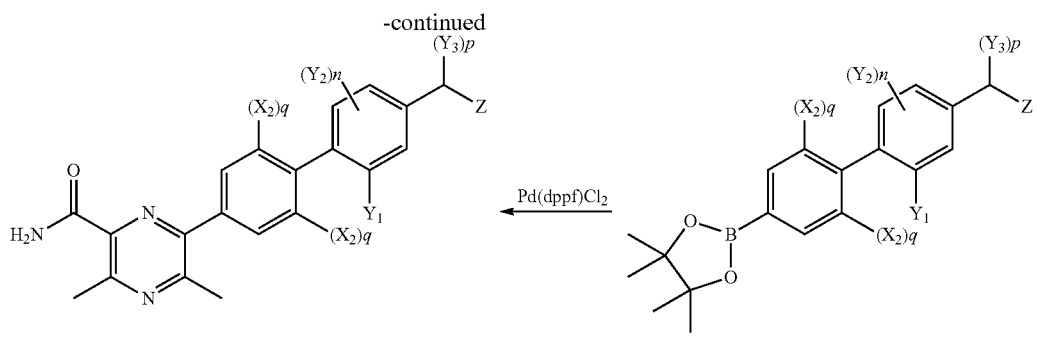

In Scheme B1, the variable substituents are those which are compatible with the reaction conditions. A protecting group, if used, can be removed, for example, by acid catalysed hydrolysis of a tert-butyl ester to give a compound of formula (I) where $Z=CO_2H$.

Preparation of Formula (III) Compounds

The following schemes illustrate how certain pyrazine ring variants may be prepared. Variables shown in the schemes are defined or can be interpreted in the context of the variants described herein for the compounds of the invention. Analogous chemistry to that shown in the schemes and Examples may be used to prepare other compounds within the scope of the invention.

Scheme B1-A: Reaction scheme for dialkylpyrazine and derivatives

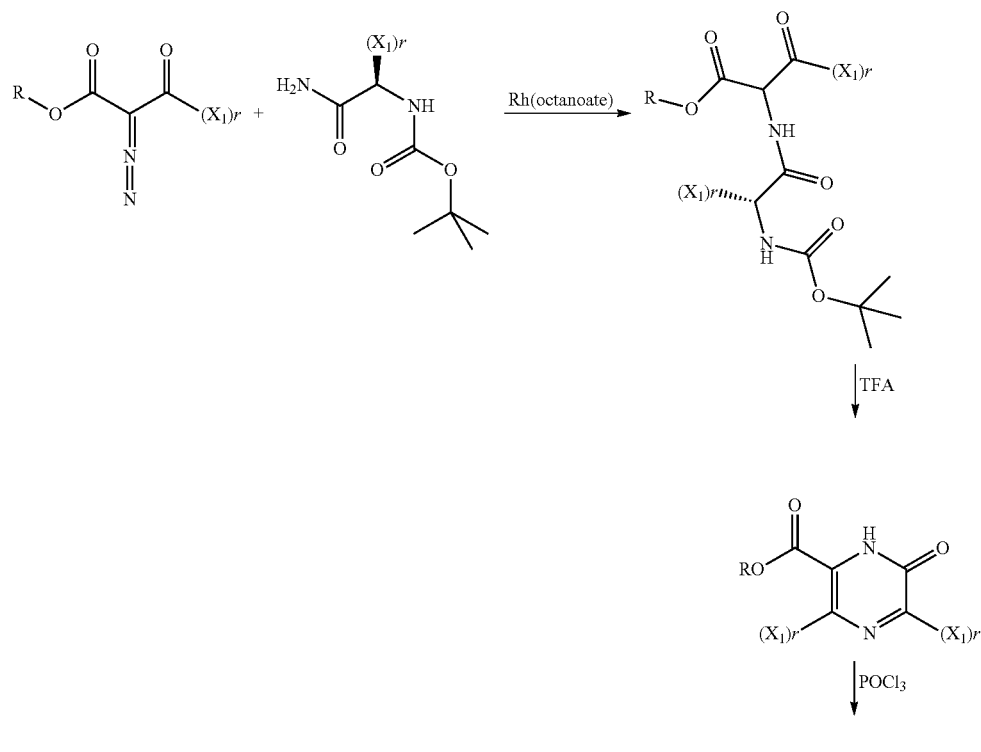

R in Scheme B1-A represents (1-4C)alkyl, for example, methyl or ethyl.

Scheme B1-B: Reaction scheme for mono-alkylpyrazine and derivatives

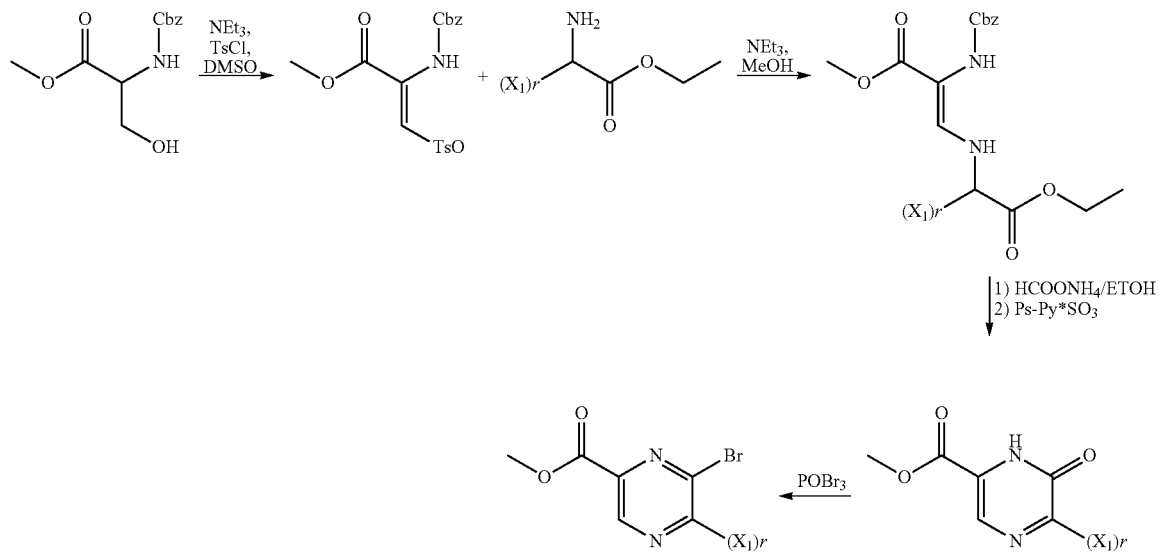

Preparation of Formula (III) and (IV) Compounds

Scheme B1-C: Reaction scheme for dimethypyrazine and derivatives

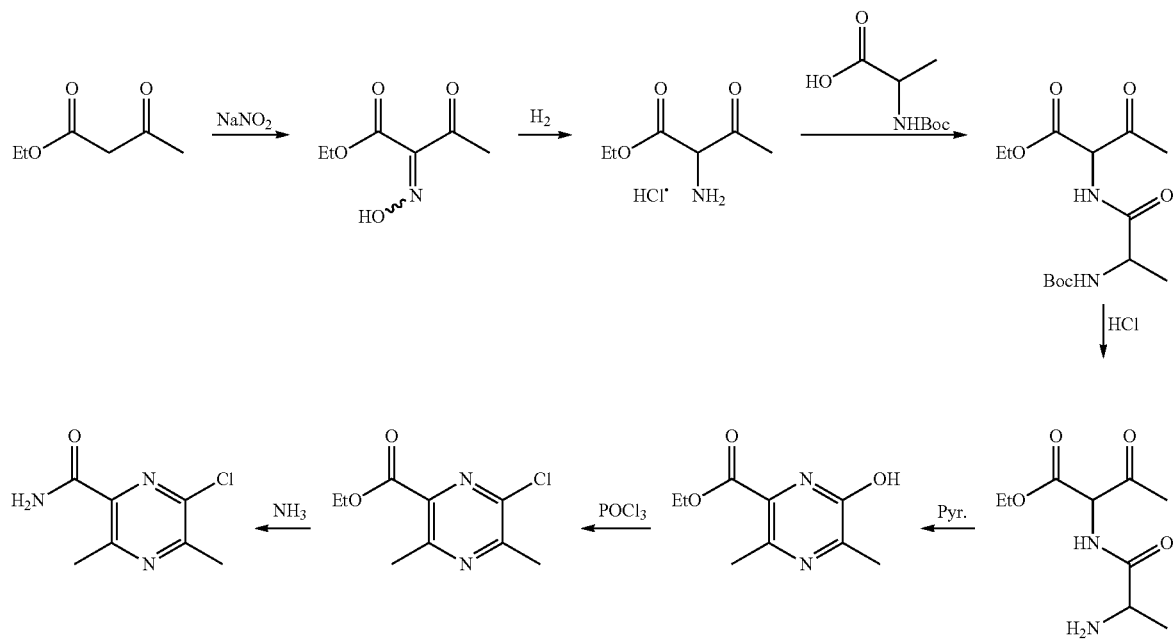

Analogues of pyrazine can be prepared using the procedure described by C. Christensen, C. W. Tornoe and M. Meldal, *QSAR & Combinatorial Science,* 2004, 23, (2-3), 109-116, for example, 3-methylpyrazine . . . .

Scheme B1-D: Reaction scheme for 3 mono-methylpyrazine and derivatives

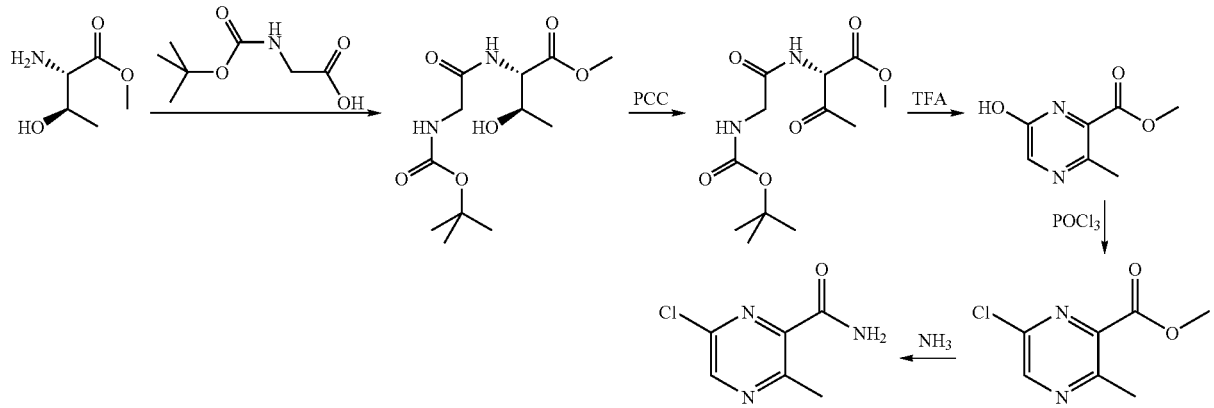

Preparation of Formula (II) Compounds

The following schemes illustrate how certain variants may be prepared. Variables shown in the schemes are defined or can be interpreted in the context of the variants described herein for the compounds of the invention. Analogous chemistry to that shown in the schemes and Examples may be used to prepare other compounds within the scope of the invention.

For compounds of formula (II) many appropriate intermediates are in the literature, or can be made by analogy, and introduction of various substitution patterns may be achieved through biphenyl Suzuki coupling (see Scheme B1-E):

Scheme B1-E: Reaction scheme for biphenyls

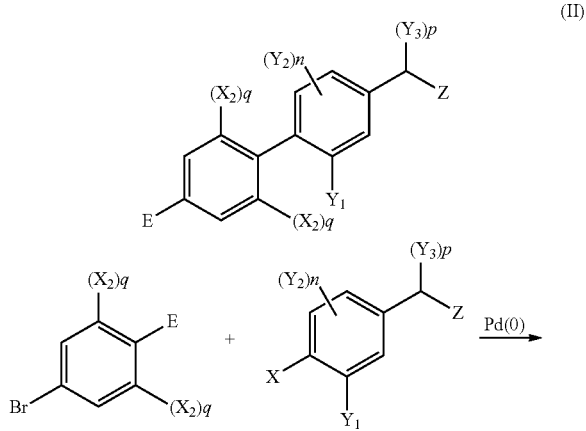

Scheme B2-A: Reaction scheme for biphenyl variants

-continued

In Scheme B1-E, X represents triflate, iodo-, bromo- or chloro and E represents a boronic acid (—B(OH)$_2$), a boronate ester (—B(OR)$_2$ wherein R here is (1-4C)alkyl) or a cyclic boronic ester, such as pinacolato borane.

The bromobiphenyl is then converted into the corresponding boron-containing derivative by standard methods.

For introduction of α-alkyl, dialkyl and cycloalkyl groups at the "Y$_3$ substitution position" standard alkylation methodology may be used on any suitable boronate ester compound, for example by deprotonation α-to the ester group using a lithium base such as LDA followed by quenching with an appropriate alkyl halide or alkyldihalide. Such chemistry is applicable in Process B1 and also Process B3 (see later).

Process B2

In an alternative sequence of Suzuki couplings a boronic ester of formula (V) is generated as an intermediate (wherein E represents a boronic acid (—B(OH)$_2$), a boronate ester (—B(OR)$_2$ wherein R here is (1-4C)alkyl) or a cyclic boronic ester, such as pinacolato borane), as illustrated by the scheme below (for the dimethylpyrazine variant). This intermediate is then used in a further Suzuki coupling to generate biphenyl compounds of formula (I).

Preparation of Formula (V) Compound Types (Ring A and Ring B)

(V)

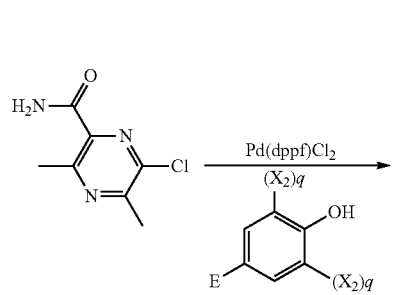
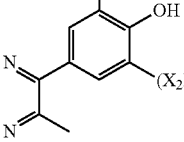
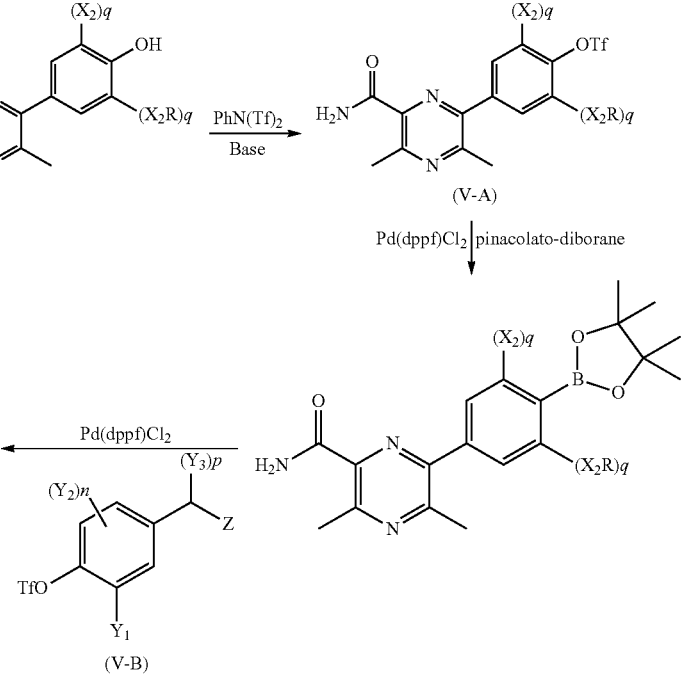

In Scheme B2-A, suitable aromatic substituents are those compatible with the reaction conditions. The phenol is converted into the corresponding triflate with $PhN(Tf)_2$ and a suitable base, such as potassium carbonate. The phenyltriflate is converted to the corresponding boronate ester followed by subsequent Suzuki reaction under standard methods with a suitable palladium catalyst, such as 1,1'-bis(diphenylphosphino)-ferrocenedichloropalladium(II). Alternatively, the boronate ester can be converted to the corresponding boronic acid.

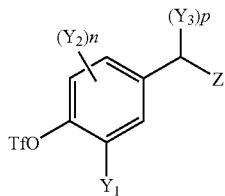

The compound of formula (V-B) can be prepared from the corresponding phenol compound by standard chemistry or from the corresponding methoxy compound after demethylation using $BBr_3$.

Process B3

In an alternative sequence of Suzuki couplings a boron-containing compound of formula (VI) (wherein E represents a boronic acid (—$B(OH)_2$), a boronate ester (—$B(OR)_2$ wherein R here is (1-4C)alkyl) or a cyclic boronic ester, such as pinacolato borane) is generated as an intermediate and reacted with the triflate of formula (V-A) in Scheme B2-A to generate biphenyl compounds of the formula (I).

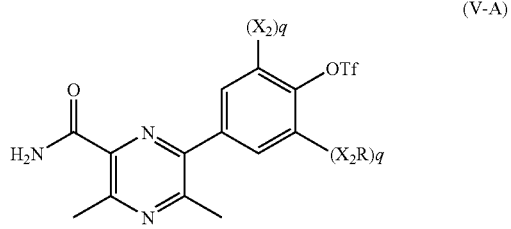

Chiral compounds (for example at the "Y3" position) can be prepared as follows . . .

(i) by chromatographic separation from a final mixture of compounds (for example, see the Examples); suitable hplc chiral stationary phases include Chiralpak OJ and AD columns;

(ii) by directed methylation utilising a chiral auxilliary by the method described by J. S Yadav et al Tet. Lett. 2007, 48, 2841-2843 and illustrated in the scheme below, followed by Suzuki coupling and hydrolytic cleavage of the auxilliary to afford a single enantiomer of the relevant Example compound;

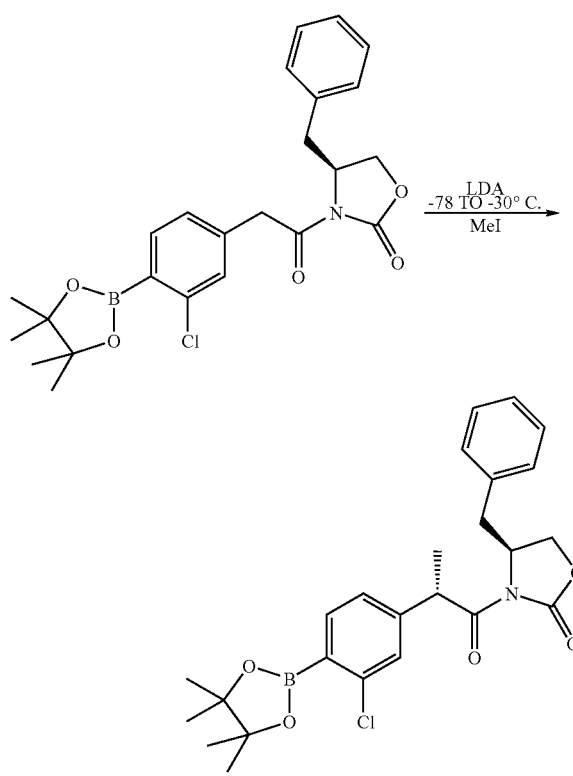

(iii) by final chiral reduction of an alpha-methylene acid by catalytic hydrogenation, for example as described by R Noyori et al. J. Org. Chem., 1987, 52, 3174-3176 and illustrated in the scheme below:

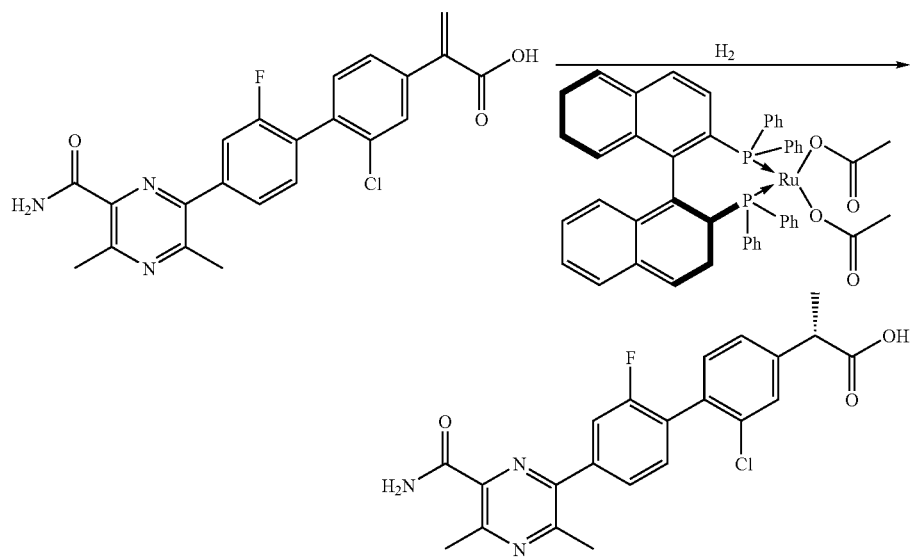

Such alpha-methylene acids may be prepared by reaction of the corresponding alpha-unsubstituted esters with formaldehyde or equivalent under standard conditions followed by basic hydrolysis of the ester.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, 5$^{th}$ Edition, by Jerry March and Michael Smith, published by John Wiley & Sons 2001, for general guidance on reaction conditions and reagents.

It will be appreciated that some intermediates to compounds of the formula (I) are also novel and these are provided as separate independent aspects of the invention. In particular, certain compounds of formula (IV) may form a further independent aspect of the invention. Furthermore, ester derivatives of compounds of formula (I) form a further aspect of the invention.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl or SEM may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the examples herein, to obtain necessary starting materials, and products.

The removal of any protecting groups and the formation of a pharmaceutically-acceptable salt are within the skill of an ordinary organic chemist using standard techniques. Furthermore, details on the these steps has been provided hereinbefore.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

According to a further aspect of the present invention there is provided a compound of formula (I), or a pharmaceutically acceptable salt, or a pro-drug thereof as defined hereinbefore for use in a method of treatment of the human or animal body by therapy.

We have found that compounds of the present invention inhibit DGAT1 activity and are therefore of interest for their blood glucose-lowering effects.

A further feature of the present invention is a compound of formula (I), or a pharmaceutically-acceptable salt, or a pro-drug thereof for use as a medicament.

Conveniently this is a compound of formula (I), or a pharmaceutically-acceptable salt, or a pro-drug thereof, for (use as a medicament for) producing an inhibition of DGAT1 activity in a warm-blooded animal such as a human being.

Particularly this is a compound of formula (I), or a pharmaceutically-acceptable salt, or a pro-drug thereof, for (use as a medicament for) treating diabetes mellitus and/or obesity in a warm-blooded animal such as a human being.

Thus according to a further aspect of the invention there is provided the use of a compound of formula (I), or a pharmaceutically-acceptable salt, or a pro-drug thereof in the manufacture of a medicament for use in the production of an inhibition of DGAT1 activity in a warm-blooded animal such as a human being.

Thus according to a further aspect of the invention there is provided the use of a compound of formula (I), or a pharmaceutically-acceptable salt, or a pro-drug thereof in the manufacture of a medicament for use in the treatment of diabetes mellitus and/or obesity in a warm-blooded animal such as a human being.

According to a further aspect of the invention there is provided a pharmaceutical composition which comprises a compound of formula (I) as defined hereinbefore, or a pharmaceutically-acceptable salt, or a pro-drug thereof, in association with a pharmaceutically-acceptable excipient or carrier for use in producing an inhibition of DGAT1 activity in an warm-blooded animal, such as a human being.

According to a further aspect of the invention there is provided a pharmaceutical composition which comprises a compound of formula (I) as defined hereinbefore, or a pharmaceutically-acceptable salt, or a pro-drug thereof, in association with a pharmaceutically-acceptable excipient or carrier for use in the treatment of diabetes mellitus and/or obesity in an warm-blooded animal, such as a human being.

According to a further feature of the invention there is provided a method for producing an inhibition of DGAT1 activity in a warm-blooded animal, such as a human being, in need of such treatment which comprises administering to said animal an effective amount of a compound of formula (I), or a pharmaceutically-acceptable salt, or a pro-drug thereof as defined hereinbefore.

According to a further feature of the invention there is provided a method of treating diabetes mellitus and/or obesity in a warm-blooded animal, such as a human being, in need of such treatment which comprises administering to said animal an effective amount of a compound of formula (I), or a pharmaceutically-acceptable salt, or a pro-drug thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 0.1-50 mg/kg is employed. In another embodiment a daily dose is in the range of 0.01-50 mg/kg, particularly 0.01-10 mg/kg, 0.01-1 mg/kg or 0.01-0.1 mg/kg. However the daily dose will necessarily be varied depending upon the host treated, the particular route of administration, and the severity of the illness being treated. Accordingly the optimum dosage may be determined by the practitioner who is treating any particular patient.

As stated above compounds defined in the present invention are of interest for their ability to inhibit the activity of DGAT1. A compound of the invention may therefore be useful for the prevention, delay or treatment of a range of disease states including diabetes mellitus, more specifically type 2 diabetes mellitus (T2DM) and complications arising there from (for example retinopathy, neuropathy and nephropathy), impaired glucose tolerance (IGT), conditions of impaired fasting glucose, metabolic acidosis, ketosis, dysmetabolic syndrome, arthritis, osteoporosis, obesity and obesity related disorders, (which include peripheral vascular disease, (including intermittent claudication), cardiac failure and certain cardiac myopathies, myocardial ischaemia, cerebral ischaemia and reperfusion, hyperlipidaemias, atherosclerosis, infertility and polycystic ovary syndrome); the compounds of the invention may also be useful for muscle weakness, diseases of the skin such as acne, various immunomodulatory diseases (such as psoriasis), HIV infection, inflammatory bowel syndrome and inflammatory bowel disease such as Crohn's disease and ulcerative colitis.

In particular, the compounds of the present invention are of interest for the prevention, delay or treatment of diabetes mellitus and/or obesity and/or obesity related disorders. In one aspect, the compounds of the invention are used for prevention, delay or treatment of diabetes mellitus. In another aspect, the compounds of the invention are used for prevention, delay or treatment of obesity. In a further aspect, the compounds of the invention are used for prevention, delay or treatment of obesity related disorders.

The inhibition of DGAT1 activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example such conjoint treatment may be beneficial in the treatment of metabolic syndrome [defined as abdominal obesity (as measured by waist circumference against ethnic and gender specific cut-points) plus any two of the following: hypertriglyceridemia (>150 mg/dl; 1.7 mmol/l); low HDLc (<40 mg/dl or <1.03 mmol/l for men and <50 mg/dl or 1.29 mmol/l for women) or on treatment for low HDL (high density lipoprotein); hypertension (SBP≧130 mmHg DBP≧85 mmHg) or on treatment for hypertension; and hyperglycemia (fasting plasma glucose≧100 mg/dl or 5.6 mmol/l or impaired glucose tolerance or pre-existing diabetes mellitus)—International Diabetes Federation & input from IAS/NCEP].

Such conjoint treatments may include the following main categories:

1) Anti-obesity therapies such as those that cause weight loss by effects on food intake, nutrient absorption or energy expenditure, such as orlistat, sibutramine and the like.
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors, glucokinase activators);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-dyslipidaemia agents such as, HMG-CoA reductase inhibitors (eg statins); PPAR α-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
10) Antihypertensive agents such as β-blockers (eg atenolol, inderal); ACE inhibitors (eg lisinopril); Calcium antagonists (eg. nifedipine); Angiotensin receptor antagonists (eg candesartan), α-antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
12) Agents which antagonise the actions of glucagon; and
13) Anti-inflammatory agents, such as non-steroidal anti-inflammatory drugs (eg. aspirin) and steroidal anti-inflammatory agents (eg. cortisone).

In addition to their use in therapeutic medicine, compounds of formula (I) and their pharmaceutically-acceptable salts are also useful as pharmacological tools in the development and standardisation of in vitro and in vivo test systems for the evaluation of the effects of inhibitors of DGAT1 activity in laboratory animals such as cats, dogs, rabbits, monkeys, rats and mice, as part of the search for new therapeutic agents.

In the above other pharmaceutical composition, process, method, use and medicament manufacture features, the alternative, particular and preferred embodiments of the compounds of the invention described herein also apply. The alternative, particular and preferred embodiments of the invention described herein also apply to a compound of formula (I), or a pharmaceutically-acceptable salt, or a pro-drug thereof.

As indicated above, all of the compounds, and their corresponding pharmaceutically-acceptable salts, are useful in inhibiting DGAT1. The ability of the compounds of formula (I), and their corresponding pharmaceutically-acceptable (acid addition) salts, to inhibit DGAT1 may be demonstrated employing the following enzyme assay:

Human Enzyme Assay

See, for example, International Application WO 2005/044250.

The in vitro assay to identify DGAT1 inhibitors uses human DGAT1 expressed in insect cell membranes as the enzyme source (Proc. Natl. Acad. Sci. 1998, 95, 13018-13023). Briefly, sf9 cells were infected with recombinant baculovirus containing human DGAT1 coding sequences and harvested after 48 h. Cells were lysed by sonication and membranes isolated by centrifuging at 28000 rpm for 1 h at 4°

C. on a 41% sucrose gradient. The membrane fraction at the interphase was collected, washed, and stored in liquid nitrogen.

DGAT1 activity was assayed by a modification of the method described by Coleman (Methods in Enzymology 1992, 209, 98-102). Compound at 0.0000256 µM (or 0.003 µM)-33 µM (final conc.) (typically 10 µM) was incubated with 4 µg/ml (final conc) membrane protein, 5 mM $MgCl_2$, and 100 µM 1,2 dioleoyl-sn-glycerol (dissolved in acetone with a final assay conc. of acetone of 10%) in a total assay volume of 200 µl in a 96 well plate. The reaction was started by adding $^{14}C$ oleoyl coenzyme A (30 µM final concentration) and incubated at room temperature for 30 minutes. The reaction was stopped by adding 200 µl 2-propanol:heptane 7:1. Radioactive triolein product was separated into the organic phase by adding 300 µl heptane and 100 µl 0.1 M carbonate buffer pH 9.5. DGAT1 activity was quantified by counting aliquots of the upper heptane layer by liquid scintillography.

Using this assay the compounds generally show activity with an $IC_{50}$ around or below 10 µM, preferably below 10 µM (i.e. $IC_{50}$<10 µM), preferably <1 µM, more preferably <0.1 µM, particularly, <0.05 µM, and more particularly <0.01 µM. Stated figures are usually a mean of a number of measurements (usually 2 measurements) according to standard practice.

Examples 1 to 10 showed, respectively, an $IC_{50}$=0.0061 µM; 0.0077 µM; 0.017 µM; 0.012 µM; 0.014 µM; 0.018 µM; 0.027 µM; 0.012 µM; 0.018 µM; 0.011 µM.

Examples 11 to 20 showed, respectively, $IC_{50}$=0.017 µM; 0.02 µM; 0.021 µM; 0.0036 µM; 0.011 µM; 0.013 µM; 0.013 µM; 0.016 µM; 0.023 µM; 0.024 µM.

Examples 21 to 30 showed, respectively, $IC_{50}$=0.015 µM; 0.0084 µM; 0.014 µM; 0.013 µM; 0.025 µM; 0.0063 µM; 0.013 µM; 0.017 µM; 0.018 µM; 0.011 µM.

The ability of the compounds of formula (I), and their corresponding pharmaceutically-acceptable (acid) salts, to inhibit DGAT1 may further be demonstrated employing the following whole cell assay.

Measurement of Triglyceride Synthesis in HuTu 80 Cells

HuTu80 cells were cultured to confluency in 6 well plates in minimum essential media containing foetal calf serum. For the experiment, the medium was changed to serum-free medium and the cells pre-incubated with compound solubilised in DMSO (final concentration 0.1%) for 30 minutes. De novo lipogenesis was measured by the addition of 0.12 mM sodium oleate plus 1 µCi/mL $^{14}C$-sodium oleate complexed to 0.03 mM BSA to each well for a further 2 h. The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane: acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (1997). Incorporation of radiolabel into the triglyceride fraction was analysed using a Radiomatic Flo-one Detector (Packard) connected to the HPLC machine.

EXAMPLES

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and generally under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated with flash chromatography purifications run on Biotage SP1 or SP4 instruments using Biotage Silica columns;

(vii) mass spectra were recorded on a Finnigan LCQ Duo ion trap mass spectrometer equipped with an electrospray interface (LC-MS) or LC-MS system consisting of a Waters ZQ using a LC-Agilent 1100 LC system;

(viii) $^1H$ NMR measurements were performed on a Varian Mercury VXR 300 and 400 spectrometer, operating at a 1H frequency of 300 and 400 and Varian UNITY plus 400, 500 and 600 spectrometers, operating at 1H frequencies of 400, 500 and 600 respectively. Chemical shifts are given in ppm with the solvent as internal standard. Protons on heteroatoms such as NH and OH protons are only reported when detected in NMR and can therefore be missing.

(ix) HPLC separations were performed on a Waters YMC-ODS AQS-3 120 Angstrom 3×500 mm or on a Waters Delta Prep Systems using Kromasil C8, 10 µm columns. Acidic HPLC was carried out using gradients of mobilephase A: 100% ACN and mobilephase B: 5% ACN+95% $H_2O$+0.2% FA. Neutral HPLC was carried out using gradients of mobilephase A: 100% ACN and mobilephase B: 5% ACN+95% 0.1 M $NH_4OAc$.

(x) Reactions performed in a microwave oven were run in a Biotage Initiator Instrument.

(xi) Chemical nomenclature software packages, such as Struc=Name/CambridgeSoft ELN, may have been used in the naming of compounds.

List of Abbreviations that May be Used Herein:
ACN Acetonitrile
aq Aqueous
Boc tert-butyloxycarbonyl
Brine Saturated solution of sodium chloride in water
BSA Bovine Serum Albumine
Cbz Benzylozycarbonyl
DCE 1,2-dichloroethane
DCM Dichloromethane
DEE Diethylether
DIPEA N,N-Diisopropylethylamine DMAP Dimethylaminopyridine
DMF N,N-dimethylformamide
DMSO Dimethylsulphoxide
Dppf 1,1'-bis(Diphenylphosphino)ferrocene
EDCI 1-Ethyl-3-(3-dimethylaminopropyl)carbodiimide hydrochloride
EDTA Ethylenediaminetetraacetic acid
EtOAc Ethyl acetate
EtOH Ethanol
FA Formic acid
HOAc Acetic acid
HPLC High-performance liquid chromatography
HWE Horner-Wadsworth-Emmons
Hz Hertz
IPA Isopropylalcohol
iPr isopropyl
LC Liquid chromatography
m-CPBA meta-chloroperoxybenzoicacid
MeOH Methanol
MHz Megahertz
mL Millilitre
MS Mass spectra
NMM N-methylmorpholine
NMP N-methylpiperazine
NMR Nuclear magnetic resonance
OAc acetate
Ph Phenyl
PyBOP Benzotriazol-1-yl-oxytri-pyrrolidinophosphonium hexafluorophosphate
PyBROP Bromo-tris-pyrrolidino-phosphonium Hexafluorophosphate
Ps-Py-SO$_3$ Polymer supported pryridine-SO$_3$ complex
RT Room temperature
sat saturated
TEA Triethylamine
Tf trifluoromethylsulfonyl
TFA Trifluoroacetic acid
THF Tetrahydrofurane
TLC Thin layer chromatography
Ts p-toluenesulfonyl Example 1

2-(4'-(6-Carbamoyl-3,5-dimethylpyrazin-2-yl)-2-chlorobiphenyl-4-yl)-acetic acid

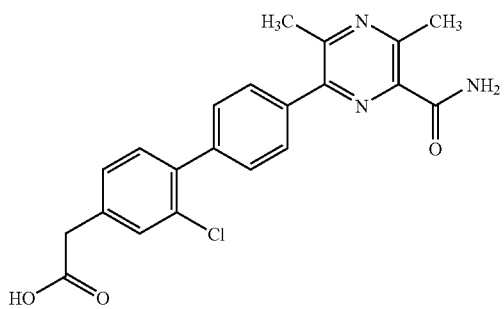

Powdered potassium hydroxide (45.2 mg, 0.81 mmol) was added in one portion to methyl 2-(4'-(6-carbamoyl-3,5-dimethylpyrazin-2-yl)-2-chlorobiphenyl-4-yl)acetate (Intermediate 1-1; 110 mg, 0.27 mmol) in tert-butanol (10 mL) at 45° C. The resulting solution was stirred at 45° C. for 15 minutes, a thick white suspension slowly formed. 2M HCl (2 mL) was added and the mixture was evaporated to remove the organic solvent. The suspension was collected by filtration, washed with water (5 mL) and dried under vacuum to afford 2-(4'-(6-carbamoyl-3,5-dimethylpyrazin-2-yl)-2-chlorobiphenyl-4-yl)acetic acid (82 mg, 77%) as a white solid.
$^1$H NMR (400.132 MHz, DMSO) δ 2.65 (3H, s), 2.76 (3H, s), 3.68 (2H, s), 7.34 (1H, d), 7.43 (1H, d), 7.51 (1H, s), 7.57 (2H, d), 7.61 (1H, s), 7.85 (2H, d), 8.04 (1H, s), 12.45 (1H, s). m/z (ES+) (M+H)+=396

Intermediate 1-1: Methyl 2-(4'-(6-carbamoyl-3,5-dimethylpyrazin-2-yl)-2-chlorobiphenyl-4-yl)acetate

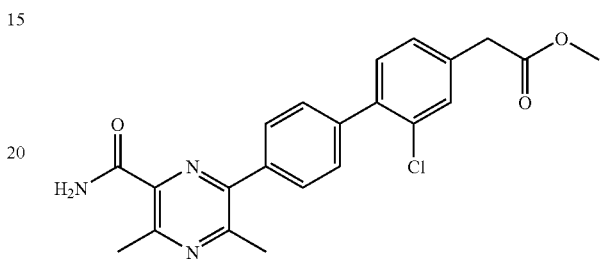

To a degassed solution of 3,5-dimethyl-6-(4-(4,4,5,5-tetramethyl-1,3,2-dioxaborolan-2-yl)phenyl)pyrazine-2-carboxamide (Intermediate 7-6; 196 mg, 0.55 mmol) in DME (6 mL), ethanol (1.5 mL) and water (1.5 mL) was added tripotassium phosphate (141 mg, 0.67 mmol), methyl 2-(3-chloro-4-(trifluoromethylsulfonyloxy)phenyl)acetate (Intermediate 1-2; 185 mg, 0.55 mmol) followed by (1,1'-bis(diphenylphosphino)ferrocene)-dichloropalladium(II) (DCM adduct) (36.5 mg, 0.04 mmol). The resulting mixture was stirred at 80° C. under nitrogen for 4 hours. The reaction mixture was allowed to cool to ambient temperature, evaporated and partitioned between EtOAc (75 mL) and saturated brine (50 mL) then filtered through celite. The organic layer was dried over MgSO$_4$, filtered and evaporated to afford crude product. The crude product was purified by flash silica chromatography, elution gradient 20 to 80% EtOAc in isohexane. Pure fractions were evaporated to dryness to afford methyl 2-(4'-(6-carbamoyl-3,5-dimethylpyrazin-2-yl)-2-chlorobiphenyl-4-yl)acetate (110 mg, 48.4%) as a white solid.
$^1$H NMR (400.132 MHz, DMSO) δ 2.65 (3H, s), 2.76 (3H, s), 3.65 (3H, s), 3.79 (2H, s), 7.35 (1H, d), 7.44 (1H, d), 7.53 (1H, s), 7.57 (2H, d), 7.61 (1H, s), 7.85 (2H, d), 8.03 (1H, s). m/z (ES+) (M+H)+=410

Intermediate 1-2: Methyl 2-(3-chloro-4-(trifluoromethylsulfonyloxy)phenyl)acetate

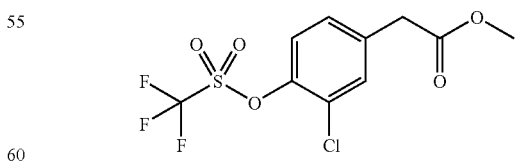

Triethylamine (50.4 mL, 361.88 mmol) was added dropwise to a stirred solution of methyl 2-(3-chloro-4-hydroxyphenyl)acetate (24.2 g, 120.63 mmol) and trifluoromethanesulphonic anhydride (Intermediate 1-3; 29.7 mL, 180.94 mmol) in DCM (500 mL) at 0° C., over a period of 15 minutes under nitrogen. The resulting solution was stirred at 0° C. for 90 minutes. The reaction mixture was washed sequentially with saturated NaHCO$_3$ (300 mL) and saturated brine (300 mL). The organic layer was dried over MgSO$_4$, filtered and evaporated to afford crude product. The crude product was purified by flash silica chromatography, elution gradient 0 to 20% EtOAc in isohexane. Pure fractions were evaporated to dryness to afford methyl 2-(3-chloro-4-(trifluoromethylsulfonyloxy)phenyl)acetate (36.1 g, 90%) as a yellow oil which solidified on standing.

$^1$H NMR (400.132 MHz, CDCl$_3$) δ 3.63 (2H, s), 3.73 (3H, s), 7.25-7.28 (1H, m), 7.31 (1H, d), 7.47 (1H, s). m/z (ES−) (M−H)−=331

Intermediate 1-3: Methyl 2-(3-chloro-4-hydroxyphenyl)acetate

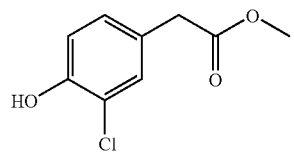

A solution of 3-chloro-4-hydroxyphenylacetic acid (24.55 g, 131.57 mmol) and sulfuric acid (0.701 mL, 13.16 mmol) in methanol (600 mL) was stirred at 75° C. for 3 hours. The reaction mixture was allowed to cool to ambient temperature evaporated to dryness and redissolved in EtOAc (500 mL), and washed with saturated brine (2×300 mL). The organic layer was dried over MgSO$_4$, filtered and evaporated to afford methyl 2-(3-chloro-4-hydroxyphenyl)acetate (24.20 g, 92%) as a pale yellow oil.

$^1$H NMR (400.132 MHz, CDCl$_3$) δ 3.53 (2H, s), 3.70 (3H, s), 5.49 (1H, s), 6.96 (1H, d), 7.07-7.10 (1H, m), 7.26 (1H, s). m/z (ES−) (M−H)−=199

Example 2

2-(4'-(6-Carbamoyl-3,5-dimethylpyrazin-2-yl)-2-chloro-2',6'-difluorobiphenyl-4-yl)acetic acid

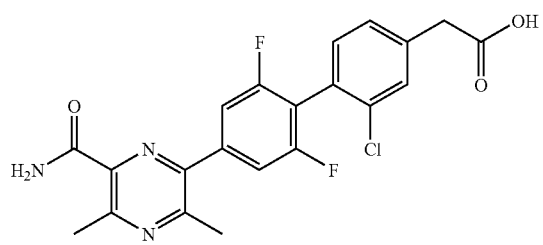

Powdered potassium hydroxide (111 mg, 1.98 mmol) was added in one portion to methyl 2-(4'-(6-carbamoyl-3,5-dimethylpyrazin-2-yl)-2-chloro-2',6'-difluorobiphenyl-4-yl)acetate (Intermediate 2-1; 295 mg, 0.66 mmol) in tert-butanol (10 mL) at 50° C. The resulting solution was stirred at 50° C. for 45 minutes, 2M HCl (2 mL) was added and the mixture was evaporated to remove the organic solvent. The suspension was collected by filtration, washed with water (50 mL) and air dried to afford 2-(4'-(6-carbamoyl-3,5-dimethylpyrazin-2-yl)-2-chloro-2',6'-difluorobiphenyl-4-yl)acetic acid (220 mg, 77%) as a cream solid.

$^1$H NMR (400.132 MHz, DMSO) δ 2.68 (3H, s), 2.78 (3H, s), 3.71 (2H, s), 7.39 (1H, d), 7.48 (1H, d), 7.58 (1H, s), 7.64 (1H, s), 7.71-7.76 (2H, m), 8.16 (1H, s), 12.50 (1H, s). m/z (ES+) (M+H)+=432

Intermediate 2-1: Methyl 2-(4'-(6-carbamoyl-3,5-dimethylpyrazin-2-yl)-2-chloro-2',6'-difluorobiphenyl-4-yl)acetate

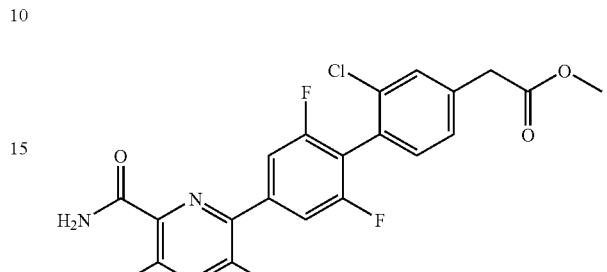

A solution of 6-chloro-3,5-dimethylpyrazine-2-carboxamide (Intermediate A) (228 mg, 1.23 mmol) and methyl 2-(2-chloro-2',6'-difluoro-4'-(4,4,5,5-tetramethyl-1,3,2-dioxaborolan-2-yl)biphenyl-4-yl)acetate (Intermediate 2-2; 521 mg, 1.23 mmol) and potassium phosphate, tri-basic (314 mg, 1.48 mmol) in DME (15 mL), MeOH (3.75 mL) and water (3.75 mL) was thoughroughly degassed. The mixture was treated with PdCl$_2$(dppf)-DCM adduct (50.3 mg, 0.06 mmol), degassed again and the atmosphere replaced with nitrogen before being heated to 80° C. for 17 hours. The reaction mixture was allowed to cool to room temperature and then evaporated. The crude product was partitioned between EtOAc (75 mL), and 2M HCl (50 mL), the aqueous phase was extracted with a further 80 mL of EtOAc. The organic extracts were combined, dried over MgSO$_4$, filtered and evaporated to afford crude product. The crude product was purified by flash silica chromatography, elution gradient 10 to 70% EtOAc in isohexane. Pure fractions were evaporated to dryness to afford methyl 2-(4'-(6-carbamoyl-3,5-dimethylpyrazin-2-yl)-2-chloro-2',6'-difluorobiphenyl-4-yl)acetate (295 mg, 53.7%) as a white solid.

$^1$H NMR (400.132 MHz, DMSO) δ 2.68 (3H, s), 2.78 (3H, s), 3.67 (3H, s), 3.83 (2H, s), 7.38-7.42 (1H, m), 7.49 (1H, d), 7.61 (1H, s), 7.64 (1H, s), 7.71-7.76 (2H, m), 8.16 (1H, s). m/z (ES+) (M+H)+=446

Intermediate 2-2: Methyl 2-(2-chloro-2',6'-difluoro-4'-(4,4,5,5-tetramethyl-1,3,2-dioxaborolan-2-yl)biphenyl-4-yl)acetate

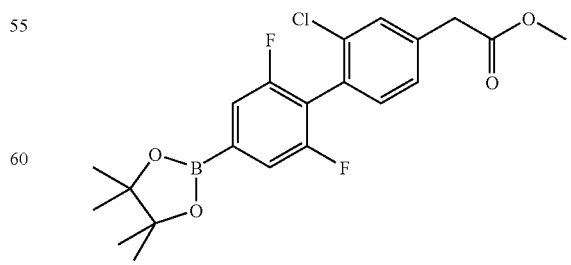

A solution of methyl 2-(2-chloro-2',6'-difluoro-4'-(trifluoromethylsulfonyloxy)biphenyl-4-yl)acetate (Intermediate 2-3; 675 mg, 1.52 mmol) in dioxane (13.8 mL) was degassed with nitrogen for a period of 5 minutes. Potassium acetate (447 mg, 4.55 mmol), 4,4,4',4',5,5,5',5'-octamethyl-2,2'-bi(1,3,2-dioxaborolane) (424 mg, 1.67 mmol), (1,1'-bis(diphenylphosphino)ferrocene)-dichloropalladium(II) (74.9 mg, 0.09 mmol) and 1,1'-bis(diphenylphosphino)ferrocene (51.0 mg, 0.09 mmol) were added and sealed into a microwave tube. The reaction was heated to 140° C. for 25 minutes in the microwave reactor and cooled to RT. The reaction mixture was concentrated and diluted with EtOAc (15 mL), and then mixture was filtered through silica. The filtrate was evaporated to afford crude product. The crude product was purified by flash silica chromatography, elution gradient 0 to 20% EtOAc in isohexane. Pure fractions were evaporated to dryness to afford methyl 2-(2-chloro-2',6'-difluoro-4'-(4,4,5,5-tetramethyl-1,3,2-dioxaborolan-2-yl)biphenyl-4-yl)acetate (521 mg, 81%) as a colourless gum.

$^1$H NMR (400.132 MHz, CDCl$_3$) δ 1.36 (12H, s), 3.65 (2H, s), 3.73 (3H, s), 7.26-7.34 (2H, m), 7.37-7.42 (2H, m), 7.46 (1H, s)

Intermediate 2-3: Methyl 2-(2-chloro-2',6'-difluoro-4'-(trifluoromethylsulfonyloxy)biphenyl-4-yl)acetate

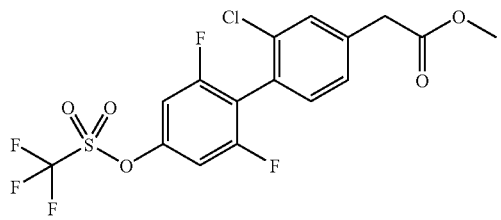

Methyl 2-(2-chloro-2',6'-difluoro-4'-hydroxybiphenyl-4-yl)acetate (Intermediate 2-4; 964 mg, 3.08 mmol), 1,1,1-trifluoro-N-phenyl-N-(trifluoromethylsulfonyl)methanesulfonamide (1.101 g, 3.08 mmol) and potassium carbonate (1.278 g, 9.25 mmol) were suspended in THF (15 mL) and sealed into a microwave tube. The reaction was heated to 120° C. for 8 minutes in the microwave reactor and cooled to RT. The suspension was filtered, the solid was washed with EtOAc (20 mL) and the filtrate was evaporated to afford crude product. The crude product was purified by flash silica chromatography, elution gradient 0 to 10% EtOAc in isohexane. Pure fractions were evaporated to dryness to afford methyl 2-(2-chloro-2',6'-difluoro-4'-(trifluoromethylsulfonyloxy)biphenyl-4-yl)acetate (675 mg, 49.2%) as a pale yellow oil.

$^1$H NMR (400.132 MHz, CDCl$_3$) δ 3.67 (2H, s), 3.74 (3H, s), 6.97-7.03 (2H, m), 7.28-7.30 (1H, m), 7.37-7.40 (1H, m), 7.48 (1H, s). m/z (ES-) (M-H)-=443

Intermediate 2-4: Methyl 2-(2-chloro-2',6'-difluoro-4'-hydroxybiphenyl-4-yl)acetate

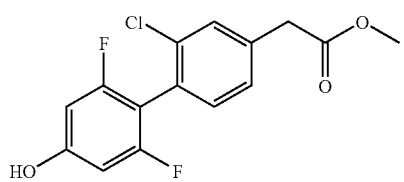

Boron tribromide (1.494 mL, 15.80 mmol) was added dropwise to 2-(2-chloro-2',6'-difluoro-4'-methoxybiphenyl-4-yl)acetic acid (Intermediate 2-5; 822 mg, 2.63 mmol) in dichloromethane (30 mL) at ambient temperature under nitrogen. The resulting solution was stirred at ambient temperature for 90 minutes. The reaction mixture was cautiously added to ice water cooled methanol (50 mL) and the mixture was stirred for a further 20 minutes. The reaction mixture was evaporated to dryness and redissolved in EtOAc (150 mL), and washed sequentially with 2M HCl (50 mL) and saturated brine (50 mL). The organic layer was dried over MgSO$_4$, filtered and evaporated to afford methyl 2-(2-chloro-2',6'-difluoro-4'-hydroxybiphenyl-4-yl)acetate (822 mg, 100%) as a yellow gum.

$^1$H NMR (400.132 MHz, CDCl$_3$) δ 3.65 (2H, s), 3.74 (3H, s), 6.46-6.51 (2H, m), 7.15-7.19 (1H, m), 7.26-7.30 (2H, m). m/z (ES-) (M-H)-=311

Intermediate 2-5: 2-(2-Chloro-2',6'-difluoro-4'-methoxybiphenyl-4-yl)acetic acid

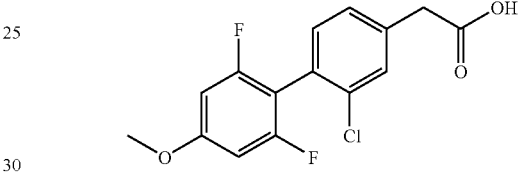

A solution of 4-bromo-3,5-difluoroanisole (645 mg, 2.89 mmol) and 2-chloro-4-(2-methoxy-2-oxoethyl)phenylboronic acid (Intermediate 2-6; 859 mg, 3.76 mmol) and sodium carbonate (2.89 mL, 5.78 mmol), tetrakis(triphenylphosphine)palladium(0) (207 mg, 0.18 mmol) in DME (20 mL) was degassed and then stirred at 85° C. for 17 hours. The reaction mixture was allowed to cool, evaporated and partitioned between EtOAc (75 mL), water (40 mL) and saturated brine (15 mL). The aqueous phase was acidified with 2M HCl and extracted into EtOAc (2×125 mL). The organic layer was dried over MgSO$_4$, filtered and evaporated to afford 2-(2-chloro-2',6'-difluoro-4'-methoxybiphenyl-4-yl)acetic acid (654 mg, 72.4%) as a white solid, which was used without further purification.

$^1$H NMR (400.132 MHz, CDCl$_3$) δ 3.67 (2H, s), 3.83 (3H, s), 6.52-6.56 (2H, m), 7.15-7.20 (1H, m), 7.28-7.30 (1H, m), 7.46 (1H, s). m/z GCMS (ES-) (M-H)-=311

Intermediate 2-6: 2-Chloro-4-(2-methoxy-2-oxoethyl)phenylboronic acid

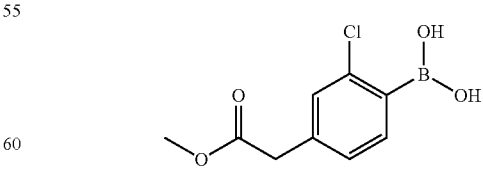

Sodium periodate (1.967 g, 9.20 mmol) and ammonium acetate (0.709 g, 9.20 mmol) were added to a stirred solution of methyl 2-(3-chloro-4-(4,4,5,5-tetramethyl-1,3,2-dioxaborolan-2-yl)phenyl)acetate (Intermediate 2-7; 0.952 g, 3.07 mmol) in acetone (20 mL) and water (10 mL). The resulting suspension was stirred at ambient temperature for 17 hours. The reaction mixture was diluted with water (50 mL) and extracted with EtOAc (3×250 mL). The organic extracts were combined washed with saturated brine (100 mL), dried over MgSO₄, filtered and evaporated to afford 2-chloro-4-(2-methoxy-2-oxoethyl)phenylboronic acid (0.656 g, 94%) as a cream oil which solidified on standing, and was used without further purification.

¹H NMR (400.132 MHz, DMSO) δ 3.61 (3H, s), 3.68 (2H, s), 7.14-7.17 (1H, m), 7.26 (1H, s), 7.35 (1H, d), 8.24 (2H, s)

Intermediate 2-7: Methyl 2-(3-chloro-4-(4,4,5,5-tetramethyl-1,3,2-dioxaborolan-2-yl)phenyl)acetate

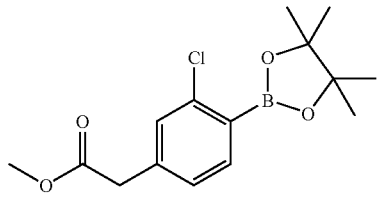

To a degassed solution of methyl 2-(3-chloro-4-(trifluoromethylsulfonyloxy)phenyl)acetate (Intermediate 1-2; 6.56 g, 19.72 mmol) in dioxane (150 mL) was added potassium acetate (6.00 g, 61.13 mmol), bis(pinacolato)diboron (7.51 g, 29.58 mmol), 1,1'-bis(diphenylphosphino)ferrocene (0.663 g, 1.18 mmol) and PdCl₂(dppf)-CH₂Cl₂ adduct (0.966 g, 1.18 mmol). The suspension was degassed and then heated, under nitrogen, to 100° C. overnight. The reaction was incomplete and further PdCl₂(dppf)-CH₂Cl₂ adduct (0.966 g, 1.18 mmol) was added and the mixture was stirred at 100° C. for a further 4 hours. The reaction mixture was allowed to cool, concentrated and diluted with EtOAc (300 mL), and washed with saturated brine (300 mL). The organic layer was dried over MgSO₄, filtered and evaporated to afford crude product which was filtered through a pad of silica (1"×3"), washing through with EtOAc. The crude product was purified by flash silica chromatography, elution gradient 0 to 20% EtOAc in isohexane. Pure fractions were evaporated to dryness to afford methyl 2-(3-chloro-4-(4,4,5,5-tetramethyl-1,3,2-dioxaborolan-2-yl)phenyl)acetate (6.11 g, 100%) as a colourless oil which solidified on standing.

¹H NMR (400.132 MHz, CDCl₃) δ 1.36 (12H, s), 3.59 (2H, s), 3.68 (3H, s), 7.14-7.16 (1H, m), 7.28 (1H, s), 7.65 (1H, d).

Intermediate A:
6-Chloro-3,5-dimethylpyrazine-2-carboxamide

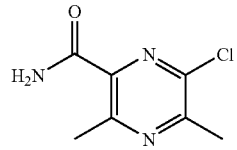

Intermediate A-1 (227 g, 1057.54 mmol) was stirred in ammonia (7N in MeOH) (1957 mL, 89633.59 mmol) at ambient temperature overnight. The mixture was evaporated to dryness and the residue was triturated with ether and the suspension was filtered and at 40° C. under vacuum to afford the title compound (181 g, 92%) as a light brown solid.

¹H NMR (400 MHz, DMSO) δ 2.59 (3H, s), 2.67 (3H, s), 7.70 (1H, s), 7.99 (1H, s) m/z 186 (M+H)⁺.

Intermediate A-1: Ethyl 6-chloro-3,5-dimethylpyrazine-2-carboxylate

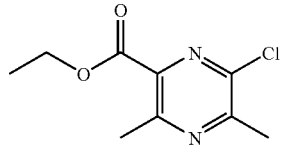

To a suspension of Intermediate A-2 (0.23 g, 1.17 mmol) in butyronitrile (4 mL) was added POCl₃ (0.27 mL, 2.93 mmol). The reaction was heated to 150° C. for 10 min in the microwave oven and cooled to RT. To the reaction mixture was added water (2 mL) and the phases were separated. The organic layer was concentrated under reduced pressure.

The crude product was purified by flash chromatography using 0.5% HOAc in DCM as eluent to afford the title compound (0.18 g, 73%).

¹H NMR (500 MHz, CDCl₃) δ 1.43 (t, 3H), 2.68 (s, 3H), 2.78 (s, 3H), 4.46 (q, 2H); m/z 215 (M+H)⁺.

Intermediate A-2: Ethyl 3,5-dimethyl-6-oxo-1,6-dihydropyrazine-2-carboxylate

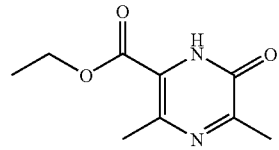

To a solution of Intermediate A-3 (800 mg, 2.53 mmol) in dry DCE (40 mL) was added TFA (1.95 mL, 25.3 mmol). The reaction mixture was heated to reflux for 4 h. The solvent was evaporated and the crude product was purified by flash chromatography using EtOAc (20-80%) in heptane as eluent. Concentration of pure fractions gave title compound (160 mg, 32%) as white-yellow powder. The crude from this reaction can optionally be used directly in the next step without purification.

¹H NMR (400 Mhz, CDCl₃) δ 4.42 (q, 2H), 2.61 (s, 3H), 2.52 (s, 3H), 1.41 (t, 3H); m/z 197 (M+H)⁺.

Intermediate A-3: Ethyl 2-{[N-(tert-butoxycarbonyl)-L-alanyl]amino}-3-oxobutanoate

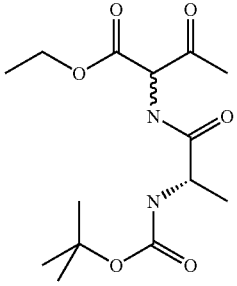

Intermediate A-4 (500 mg, 3.2 mmol) and BOC-Ala-NH₂ (843.8 mg, 4.5 mmol, CAS 85642-13-3) were added to a round bottomed flask, sealed and backfilled with argon. Dry toluene (30 mL) was added via syringe and the resulting heterogeneous mixture was stirred at 90° C. for 10 min to get a homogeneous solution. Meanwhile, the rhodium (II) octanoate dimer (62.3 mg, 0.080 mmol, CAS 73482-96-9) was dissolved in toluene (5 mL) and put on an ultrasound bath for 5 min, to get a fine Rh-dispersion. This dispersion was then added dropwise to the reaction mixture at 80° C. (a violent $N_2$ effervescence was observed).

After stirring another 20 min at elevated temperature the reaction mixture was concentrated under reduced pressure to give a black pasty solid. The N—H insertion product could here be purified or taken directly to the next step. The crude was purified by flash chromatography using EtOAc (20-80%) in heptane to afford the title compound (850 mg, 84%) (diastereomeric mixture) as a yellow oil. m/z 317 (M+H)$^+$.

Intermediate A-4: Ethyl 2-diazo-3-oxobutanoate

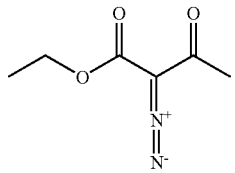

Polymer-bound tosylazide (11 g, 15.4 mmol) (typical loading 1.4 mmol/g, prepared according to Merz et al *J. Org. Chem.* 2001, 66, 2509-2511) was swollen in dry DCM (40 mL). Ethyl acetoacetate (1.0 g, 7.7 mmol, CAS 141-97-9) and TEA (3.2 mL, 23.1 mmol) were dissolved in DCM (10 mL) and added to the polymer containing solution. The resulting mixture was then shaken at RT under nitrogen until the reaction was judged completed by TLC, typically 6 h. The supernatant was filtered off, then the resin was washed with DCM (3×30 mL) to rinse out residual product. The reaction mixture was then evaporated to dryness to afford the title compound (1.1 g, 92%) as yellow oil.

$^1$H NMR (400 MHz, CDCl$_3$) δ 4.28 (q, 2H), 2.45 (s, 3H), 1.33 (t, 3H).

Typically these intermediates were not characterized due to their high-energetic properties (Clark et al, *Thermochimica Acta*, 386, 2002, 73-79), but carried through to the next step as crude products.

Alternative Preparations

Intermediate A-1: Ethyl 6-chloro-3,5-dimethylpyrazine-2-carboxylate

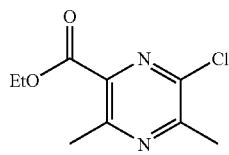

A suspension of Intermediate A-2 (268 g, 1365.93 mmol) in phosphorus oxychloride (1273 mL, 13659.31 mmol) was heated at 90° C. under nitrogen for 1 hour then cooled to ambient temperature. The reaction was cautiously added to water (6 L) with vigorous stirring keeping the temperature between 17° C. and 20° C. The mixture was then extracted with DCM (5×2.5 L), washed with water, saturated brine and dried over MgSO$_4$ and evaporated to afford crude product. The crude product was purified by flash silica chromatography, elution gradient 0 to 25% EtOAc in isohexane. Pure fractions were evaporated to dryness to afford the title compound (227 g, 77%) as a yellow oil which solidified on standing.

$^1$H NMR (400 MHz, CDCl$_3$) δ 1.43 (3H, t), 2.68 (3H, s), 2.77 (3H, s), 4.46 (2H, q); m/z 215 (M+H)$^+$.

Intermediate A-2: Ethyl 6-hydroxy-3,5-dimethylpyrazine-2-carboxylate

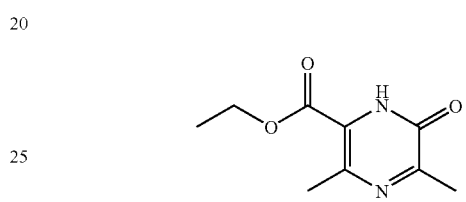

A solution of 2M Hydrochloric acid in 1,4-dioxane (1177 mL, 4709.97 mmol) was added to Intermediate A-3 (745 g, 2354.99 mmol) and stirred at room temperature for 15 minutes then warmed to 40° C. for a further 40 minutes. Pyridine (6500 mL) was then slowly added and then the reaction was heated to 80° C. for 2 hours in the presence of air. The reaction was then allowed to cool to ambient temperature and evaporated to dryness to afford a viscous oil. This was suspended in DCM (2.5 L) and washed water (1.5 L). The DCM was then dried over MgSO$_4$, filtered and concentrated to afford an orange semi-solid, which was triturated with 1:1 EtOAc/iso-hexane (250 mL) to afford ethyl 6-hydroxy-3,5-dimethyl-1,4-dihydropyrazine-2-carboxylate (127 g, 27.1%) as a cream solid. The mother liqours were then purified by flash silica chromatography (gradient from 20% ethyl acetate/iso-hexane to 80% ethyl acetate/iso-hexane). Fractions containing the desired product were concentrated and the residue was triturated with a small volume of 1:1 EtOAc/iso-hexane to afford the title compound (9.00 g, 1.948%).

Manganese dioxide (150 g) was added to a suspension of ethyl 6-hydroxy-3,5-dimethyl-4,5-dihydropyrazine-2-carboxylate (121 g, 610.44 mmol) in DCM (1.8 L) at ambient temperature giving rise to a 2° C. exotherm. The reaction was stirred for 10 minutes then warmed to 35° C. for 1 hour. The reaction was incomplete so an additional 115 g of Manganese dioxide was added and the reaction stirred for 1 hour at 35° C. then stirred to cool to ambient temperature. The reaction was filtered through a short bed of silica and washed through with 2 L of 1:1 EtOAc/iso-hexane and finally 2×2 L EtOAc. The fractions were then combined and reduce in-vacuo to give an orange solid, which was slurried in 300 mL of 1:1 EtOAc/iso-hexane, filtered and washed with iso-hexane to afford the title compound (87 g, 72.6%) as an orange solid.

$^1$H NMR (400 MHz, DMSO) δ 1.31 (3H, t), 2.35 (3H, s), 2.50 (3H, s), 4.31 (2H, q), 11.93 (1H, s); m/z 197 (M+H)$^+$

Intermediate A-3 can also be prepared by the following procedure:

Intermediate A-3: Ethyl 2-(2-(tert-butoxycarbonylamino)propanamido)-3-oxobutanoate

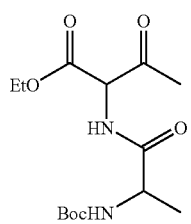

A solution of 4-methylmorpholine (900 g) in THF (15 L) was added to 2-(tert-butoxycarbonylamino)propanoic acid (1690 g, 8933.17 mmol). The mixture was cooled to −25° C. and isobutyl chloroformate (1.164 L, 8933.17 mmol) was added. After 20 minutes the second equivalent of 4-methylmorpholine (900 g) was added followed by ethyl 2-amino-3-oxobutanoate Tosylate salt (see J-P. Genet et al, *Eur. J. Org. Chem.*, 2004, 3017-3026) (2700 g, 8507.78 mmol) suspended in THF (2.5 L). The mixture was stirred at −25° C. for 30 minutes and then left to warm to ambient temperature overnight. The reaction was quenched with water (15 L), extracted with EtOAc (3×5 L) and the combined extracts washed with 50% saturated brine (5 L). The organic layer was dried over MgSO$_4$, filtered and evaporated to afford crude product. The crude product was purified by flash silica chromatography, elution gradient 50 to 80% EtOAc in isohexane. Pure fractions were evaporated to dryness to afford ethyl 2-(2-(tert-butoxycarbonylamino)propanamido)-3-oxobutanoate (1850 g, 68.7%).

Example 3

2-(4'-(6-Carbamoyl-3,5-dimethylpyrazin-2-yl)-2-chloro-5-methylbiphenyl-4-yl)acetic acid

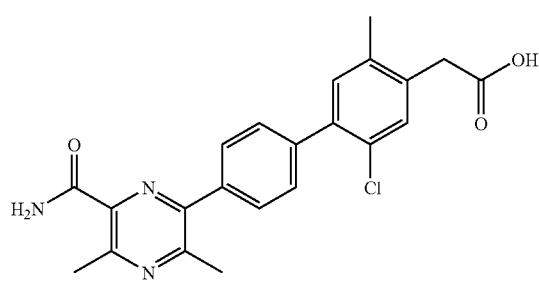

Powdered potassium hydroxide (88 mg, 1.56 mmol) was added in one portion to ethyl 2-(4'-(6-carbamoyl-3,5-dimethylpyrazin-2-yl)-2-chloro-5-methylbiphenyl-4-yl)acetate (Intermediate 3-1; 228 mg, 0.52 mmol) in tert-butanol (15 mL) at 55° C. The resulting mixture was stirred at 55° C. for 45 minutes, 2M HCl (~1 mL) was added and the mixture was evaporated to remove the organic solvent. The suspension was collected by filtration, washed with water (20 mL) and air dried to afford crude product as a pale yellow solid, which contained a minor impurity. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 2-(4'-(6-carbamoyl-3,5-dimethylpyrazin-2-yl)-2-chloro-5-methylbiphenyl-4-yl)acetic acid (193 mg, 90%) as a cream solid.

$^1$H NMR (400.132 MHz, DMSO) δ 2.27 (3H, s), 2.64 (3H, s), 2.76 (3H, s), 3.67 (2H, s), 7.30 (1H, s), 7.43 (1H, s), 7.57 (2H, d), 7.61 (1H, s), 7.84 (2H, d), 8.04 (1H, s), 12.46 (1H, s). m/z (ES+) (M+H)+=410

Intermediate 3-1: Ethyl 2-(4'-(6-carbamoyl-3,5-dimethylpyrazin-2-yl)-2-chloro-5-methylbiphenyl-4-yl)acetate

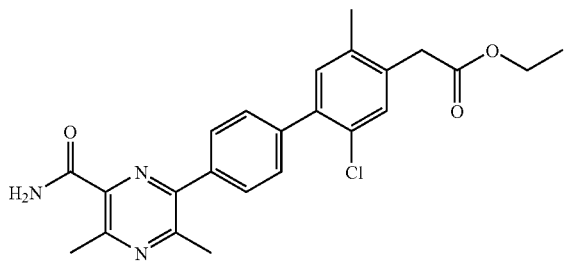

A solution of 4-(6-carbamoyl-3,5-dimethylpyrazin-2-yl)phenylboronic acid (Intermediate 5-1; 284 mg, 1.05 mmol) and ethyl 2-(5-chloro-2-methyl-4-(trifluoromethylsulfonyloxy)phenyl)acetate (Intermediate 3-2; 336 mg, 0.93 mmol) and 2M sodium carbonate (0.757 mL, 1.51 mmol), tetrakis(triphenylphosphine)palladium(0) (66.7 mg, 0.06 mmol) and lithium chloride (69.1 mg, 1.63 mmol) in DME (20 mL) and ethanol (5 mL) was degassed and then stirred at 85° C. After 4 hours further tetrakis(triphenylphosphine)palladium(0) (100 mg) and 2M sodium carbonate (0.5 mL) were added and heating was continued for a further 17 hours (overnight). The reaction mixture was allowed to cool, evaporated and partitioned between EtOAc (100 mL), water (50 mL) and 2M HCl (10 mL). The aqueous phase was re-extracted with EtOAc (100 mL), the combined organic extracts were dried over MgSO$_4$, filtered and evaporated to afford crude product. The crude product was purified by flash silica chromatography, elution gradient 0 to 50% EtOAc in isohexane. Pure fractions were evaporated to dryness to afford ethyl 2-(4'-(6-carbamoyl-3,5-dimethylpyrazin-2-yl)-2-chloro-5-methylbiphenyl-4-yl)acetate (288 mg, 70.6%) as a yellow solid.

$^1$H NMR (400.132 MHz, DMSO) δ 1.21 (3H, t), 2.26 (3H, s), 2.65 (3H, s), 2.76 (3H, s), 3.76 (2H, s), 4.12 (2H, q), 7.32

(1H, s), 7.45 (1H, s), 7.57 (2H, d), 7.61 (1H, s), 7.84 (2H, d), 8.04 (1H, s). m/z (ES+) (M+H)+=438

Intermediate 3-2: Ethyl 2-(5-chloro-2-methyl-4-(trifluoromethylsulfonyloxy)phenyl)acetate

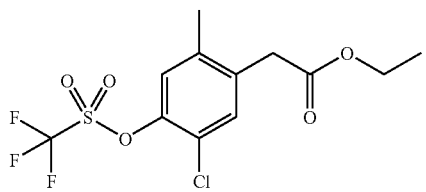

Ethyl 2-(5-chloro-4-hydroxy-2-methylphenyl)acetate (Intermediate 3-3; 310 mg, 1.36 mmol), 1,1,1-trifluoro-N-phenyl-N-(trifluoromethylsulfonyl)methanesulfonamide (484 mg, 1.36 mmol) and potassium carbonate (562 mg, 4.07 mmol) were suspended in THF (10 mL) and sealed into a microwave tube. The reaction was heated to 120° C. for 8 minutes in the microwave reactor and cooled to RT. The suspension was filtered, the solid was washed with EtOAc (20 mL) and the filtrate was evaporated to afford crude product. The crude product was purified by flash silica chromatography, elution gradient 0 to 20% EtOAc in isohexane. Pure fractions were evaporated to dryness to afford ethyl 2-(5-chloro-2-methyl-4-(trifluoromethylsulfonyloxy)phenyl)acetate (336 mg, 68.7%) as a white solid.

$^1$H NMR (400.132 MHz, CDCl$_3$) δ 1.27 (3H, t), 2.32 (3H, s), 3.60 (2H, s), 4.17 (2H, q), 7.16 (1H, s), 7.36 (1H, s). m/z (ES−) (M−H)−=359

Intermediate 3-3: Ethyl 2-(5-chloro-4-hydroxy-2-methylphenyl)acetate

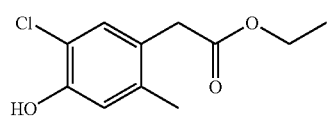

Boron tribromide (1.068 mL, 11.30 mmol) was added dropwise to ethyl 2-(5-chloro-4-methoxy-2-methylphenyl)acetate (Intermediate 3-4; 456 mg, 1.88 mmol) in dichloromethane (10 mL) at ambient temperature under nitrogen. The resulting orange red solution was stirred at 0° C. for 45 minutes. The reaction mixture was carefully quenched with water (25 mL), extracted with EtOAc (2×100 mL), the organic layer was dried over MgSO$_4$, filtered and evaporated to afford crude product as a yellow gum. The crude product was purified by flash silica chromatography, elution gradient 0 to 20% EtOAc in isohexane. Pure fractions were evaporated to dryness to afford ethyl 2-(5-chloro-4-hydroxy-2-methylphenyl)acetate (310 mg, 72.2%) as a colourless oil which solidified on standing.

$^1$H NMR (400.132 MHz, CDCl$_3$) δ 1.25 (3H, t), 2.24 (3H, s), 3.51 (2H, s), 4.15 (2H, q), 5.40 (1H, s), 6.84 (1H, s), 7.15 (1H, s). m/z (ES−) (M−H)−=227

Intermediate 3-4: Ethyl 2-(5-chloro-4-methoxy-2-methylphenyl)acetate

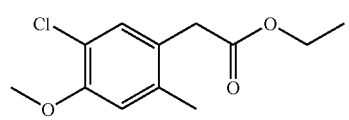

Iron powder (193 mg, 3.46 mmol) was added to a stirred solution of ethyl 2-chloro-2-(5-chloro-4-methoxy-2-methylphenyl)acetate (Intermediate 3-5; 480 mg, 1.73 mmol) in AcOH (2 mL) under nitrogen, and the resulting mixture was stirred at 60° C. for 17 hours. The reaction mixture was allowed to cool to ambient temperature, diluted with EtOAc (50 mL), filtered through celite and washed with saturated brine (3×25 mL). The organic layer was dried over MgSO$_4$, filtered and evaporated to afford crude product. The crude product was purified by flash silica chromatography, elution gradient 0 to 20% EtOAc in isohexane. Pure fractions were evaporated to dryness to afford ethyl 2-(5-chloro-4-methoxy-2-methylphenyl)acetate (190 mg, 45.2%) as a colourless gum.

$^1$H NMR (400.132 MHz, CDCl$_3$) δ 1.25 (3H, t), 2.28 (3H, s), 3.52 (2H, s), 3.88 (3H, s), 4.15 (2H, q), 6.74 (1H, s), 7.19 (1H, s). m/z GCMS (EI+) M+=242

Intermediate 3-5: Ethyl 2-chloro-2-(5-chloro-4-methoxy-2-methylphenyl)acetate

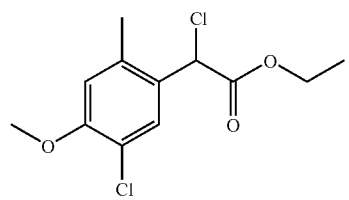

A solution of ethyl 2-(5-chloro-4-methoxy-2-methylphenyl)-2-hydroxyacetate (Intermediate 3-6; 1.1 g, 4.25 mmol) in thionyl chloride (3.42 mL, 46.89 mmol) under nitrogen was stirred at 80° C. for 30 minutes. The reaction mixture was allowed to cool concentrated and diluted with water (20 mL), extracted with EtOAc (2×20 mL), the organic layer was dried over MgSO$_4$, filtered and evaporated to afford ethyl 2-chloro-2-(5-chloro-4-methoxy-2-methylphenyl)acetate (1.170 g, 99%) as a yellow gum.

¹H NMR (400.132 MHz, CDCl₃) δ 1.27 (3H, t), 2.40 (3H, s), 3.89 (3H, s), 4.20-4.30 (2H, m), 5.50 (1H, s), 6.73 (1H, s), 7.52 (1H, s)

Intermediate 3-6: Ethyl 2-(5-chloro-4-methoxy-2-methylphenyl)-2-hydroxyacetate

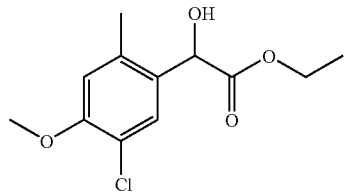

A solution of ethyl 2-(5-chloro-4-methoxy-2-methylphenyl)-2-oxoacetate (Intermediate 3-7; 6.12 g, 23.84 mmol) in warm AcOH (60 mL) was added to a stirred suspension of zinc dust (7.80 g, 119.21 mmol) in AcOH (20 mL) and the resulting suspension was stirred at ambient temperature for 16 hours. The reaction mixture was filtered, the filtrate diluted with EtOAc (200 mL), and washed with saturated brine (3×125 mL). The organic layer was dried over MgSO₄, filtered and evaporated to afford ethyl 2-(5-chloro-4-methoxy-2-methylphenyl)-2-hydroxyacetate (5.70 g, 92%) as a pale yellow oil which solidified on standing, which was used without further purification.

¹H NMR (400.132 MHz, CDCl₃) δ 1.23 (3H, t), 2.40 (3H, s), 3.89 (3H, s), 4.15-4.31 (2H, m), 5.25 (1H, s), 6.73 (1H, s), 7.30 (1H, s); OH not seen.

Intermediate 3-7: Ethyl 2-(5-chloro-4-methoxy-2-methylphenyl)-2-oxoacetate

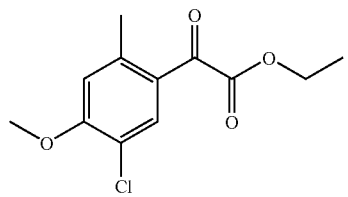

Ethyl 2-chloro-2-oxoacetate (6.43 mL, 57.47 mmol) was added dropwise to a stirred suspension of aluminum trichloride (7.66 g, 57.47 mmol) in DCM (60 mL) at 0° C., over a period of 5 minutes under nitrogen. The resulting suspension was stirred at 0° C. for 15 minutes. A solution of 1-chloro-2-methoxy-4-methylbenzene (5 g, 31.93 mmol) in DCM (50 mL) was added dropwise over a period of 5 minutes and the resulting mixture was stirred at 0° C. for 90 minutes. The reaction mixture was cautiously quenched with water (300 mL) at 0° C., extracted with EtOAc (2×200 mL), the organic layers were combined, dried over MgSO₄, filtered and evaporated to afford cream solid. The crude solid was triturated with DCM to give a solid which was collected by filtration and dried under vacuum to give ethyl 2-(5-chloro-4-methoxy-2-methylphenyl)-2-oxoacetate (4.27 g) as a white solid. The residue was purified by flash silica chromatography, elution gradient 0 to 20% EtOAc in isohexane. Pure fractions were evaporated to dryness to afford ethyl 2-(5-chloro-4-methoxy-2-methylphenyl)-2-oxoacetate (1.85 g,) as a white solid. Total yield of ethyl 2-(5-chloro-4-methoxy-2-methylphenyl)-2-oxoacetate (6.12 g, 74.7%).

¹H NMR (400.132 MHz, DMSO) δ 1.30 (3H, t), 2.53 (3H, s), 3.97 (3H, s), 4.38 (2H, q), 7.22 (1H, s), 7.76 (1H, s)

Example 4

2-(4'-(6-Carbamoyl-3,5-dimethylpyrazin-2-yl)-2,5-dichlorobiphenyl-4-yl)acetic acid

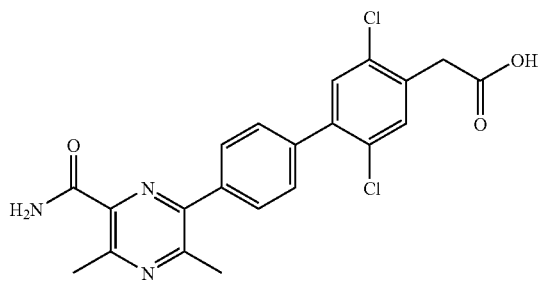

Powdered potassium hydroxide (56.1 mg, 1.00 mmol) was added in one portion to methyl 2-(4'-(6-carbamoyl-3,5-dimethylpyrazin-2-yl)-2,5-dichlorobiphenyl-4-yl)acetate (Intermediate 4-1; 148 mg, 0.33 mmol) in tert-butanol (10 mL) at 55° C. The resulting solution was stirred at 55° C. for 45 minutes, 2M HCl (2 mL) was added and the mixture was evaporated to remove the organic solvent. The suspension was collected by filtration, washed with water (50 mL) and air dried to afford crude product as a pale yellow solid, which contained a minor impurity. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 2-(4'-(6-carbamoyl-3,5-dimethylpyrazin-2-yl)-2,5-dichlorobiphenyl-4-yl)acetic acid (79 mg, 55.2%) as a white solid.

¹H NMR (400.132 MHz, DMSO) δ 2.65 (3H, s), 2.76 (3H, s), 3.80 (2H, s), 7.57-7.62 (4H, m), 7.70 (1H, s), 7.87 (2H, d), 8.04 (1H, s), 12.62 (1H, s). m/z (ES+) (M+H)+=430

Intermediate 4-1: Methyl 2-(4'-(6-carbamoyl-3,5-dimethylpyrazin-2-yl)-2,5-dichlorobiphenyl-4-yl)acetate

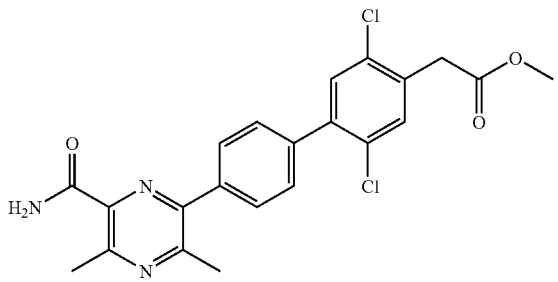

A solution of 4-(6-carbamoyl-3,5-dimethylpyrazin-2-yl)phenylboronic acid (Intermediate 5-1; 312 mg, 1.15 mmol) and methyl 2-(2,5-dichloro-4-(trifluoromethylsulfonyloxy)

phenyl)acetate (Intermediate 4-2; 375 mg, 1.02 mmol) and 2M sodium carbonate (0.830 mL, 1.66 mmol), tetrakis(triphenylphosphine)palladium(0) (73.2 mg, 0.06 mmol) and lithium chloride (76 mg, 1.79 mmol) in DME (10 mL) was degassed and then stirred at 85° C. for 17 hours. The reaction mixture was concentrated and diluted with EtOAc (75 mL), and washed sequentially with 2M HCl (25 mL) and saturated brine (25 mL). The organic layer was dried over MgSO$_4$, filtered and evaporated to afford crude product. The crude product was purified by flash silica chromatography, elution gradient 0 to 50% EtOAc in isohexane. Pure fractions were evaporated to dryness to afford methyl 2-(4'-(6-carbamoyl-3,5-dimethylpyrazin-2-yl)-2,5-dichlorobiphenyl-4-yl)acetate (148 mg, 32.6%) as a yellow solid.

$^1$H NMR (400.132 MHz, DMSO) δ 2.64 (3H, s), 2.76 (3H, s), 3.67 (3H, s), 3.91 (2H, s), 7.59-7.63 (4H, m), 7.73 (1H, s), 7.87 (2H, d), 8.03 (1H, s). m/z (ES+) (M+H)+=444

Intermediate 4-2: Methyl 2-(2,5-dichloro-4-(trifluoromethylsulfonyloxy)phenyl)acetate

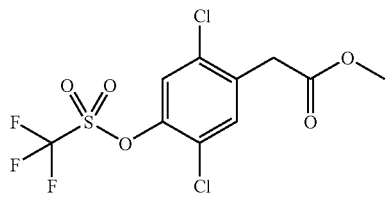

Methyl 2-(2,5-dichloro-4-hydroxyphenyl)acetate (Intermediate 4-3; 258 mg, 1.10 mmol), 1,1,1-trifluoro-N-phenyl-N-(trifluoromethylsulfonyl)methanesulfonamide (392 mg, 1.10 mmol) and potassium carbonate (455 mg, 3.29 mmol) were suspended in THF (10 mL) and sealed into a microwave tube. The reaction was heated to 120° C. for 8 minutes in the microwave reactor and cooled to RT. The suspension was filtered, the solid was washed with EtOAc (20 mL) and the filtrate was evaporated to afford crude product. The crude product was purified by flash silica chromatography, elution gradient 0 to 20% EtOAc in isohexane. Pure fractions were evaporated to dryness to afford methyl 2-(2,5-dichloro-4-(trifluoromethylsulfonyloxy)phenyl)acetate (375 mg, 93%) as a pale yellow oil.

$^1$H NMR (400.132 MHz, CDCl$_3$) δ 3.75 (3H, s), 3.77 (2H, s), 7.42 (1H, s), 7.50 (1H, m/z (ES−) (M−H)−=365

Intermediate 4-3: Methyl 2-(2,5-dichloro-4-hydroxyphenyl)acetate

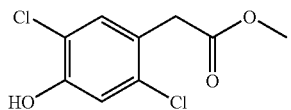

Boron tribromide (1.581 mL, 16.72 mmol) was added dropwise to 2-(2,5-dichloro-4-methoxyphenyl)acetic acid (Intermediate 4-4; 655 mg, 2.79 mmol) in dichloromethane (20 mL) at ambient temperature under nitrogen. The resulting solution was stirred at ambient temperature for 60 minutes. The reaction mixture was cautiously added to methanol (100 mL) (—care reaction is vigorous and exothermic—mixture became reasonably warm during the addition) and the mixture was stirred for a further 2 hours at ambient temperature. The reaction mixture was evaporated to dryness and redissolved in DCM (100 mL), and washed sequentially with 2M HCl (50 mL) and saturated brine (50 mL). The organic layer was dried over MgSO4, filtered and evaporated to afford crude product. The crude product was purified by flash silica chromatography, elution gradient 0 to 20% EtOAc in isohexane. Pure fractions were evaporated to dryness to afford methyl 2-(2,5-dichloro-4-hydroxyphenyl)acetate (258 mg, 39.4%) as a pale yellow solid.

$^1$H NMR (400.132 MHz, CDCl$_3$) δ 3.67 (2H, s), 3.72 (3H, s), 5.62 (1H, s), 7.07 (1H, s), 7.26 (1H, s). m/z (ES−) (M−H)−=233

Intermediate 4-4: 2-(2,5-Dichloro-4-methoxyphenyl)acetic acid

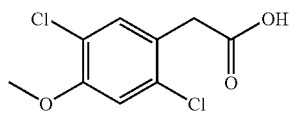

A solution of diethyl 2-(2,5-dichloro-4-methoxyphenyl)malonate (Intermediate 4-5; 1.88 g, 5.61 mmol) in THF (55 mL) and EtOH (5 mL) was treated with 2M sodium hydroxide (11.22 mL, 22.44 mmol) in one portion and the resulting solution was stirred at 60° C. for 17 hours. The reaction mixture was evaporated and the aqueous residue was acidified with 2M HCl. The precipitate was collected by filtration, washed with water (25 mL) and dried under vacuum to afford 2-(2,5-dichloro-4-methoxyphenyl)acetic acid (0.800 g, 60.7%) as a grey solid, which was used without further purification.

$^1$H NMR (400.132 MHz, DMSO) δ 3.64 (2H, s), 3.87 (3H, s), 7.23 (1H, s), 7.49 (1H, s), 12.43 (1H, s). m/z (ES−) (M−H)−=233

Intermediate 4-5: Diethyl 2-(2,5-dichloro-4-methoxyphenyl)malonate

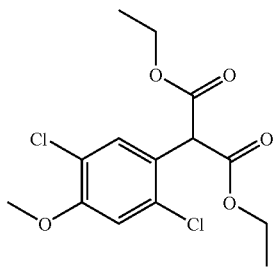

A solution of 1-bromo-2,5-dichloro-4-methoxybenzene (Intermediate 4-6; 3.82 g, 14.93 mmol), cesium carbonate (14.59 g, 44.78 mmol) and dicyclohexyl(2',4',6'-triisopropylbiphenyl-2-yl)phosphine (0.427 g, 0.90 mmol) in toluene (220 mL) was thoughroughly degassed. The mixture was treated with diacetoxypalladium (0.101 g, 0.45 mmol) and diethyl malonate (2.505 mL, 16.42 mmol) and the resulting solution stirred under a nitrogen atmosphere at 100° C. for 18 hours. The reaction mixture was allowed to cool to ambient temperature, evaporated to dryness and partitioned between EtOAc (150 mL) and water (100 mL). The mixture was filtered and the aqueous layer was separated and re extracted with EtOAc (150 mL). The organic extracts were combined, dried over MgSO₄, filtered and evaporated to afford crude product. The crude product was purified by flash silica chromatography, elution gradient 0 to 20% EtOAc in isohexane. Pure fractions were evaporated to dryness to afford diethyl 2-(2,5-dichloro-4-methoxyphenyl)malonate (1.880 g, 37.6%) as a yellow oil.

$^1$H NMR (400.132 MHz, CDCl₃) δ 1.28 (6H, t), 3.89 (3H, s), 4.21 (4H, q), 5.09 (1H, s), 6.96 (1H, s), 7.53 (1H, s). m/z (ES−) (M−H)−=335

Intermediate 4-6:
1-Bromo-2,5-dichloro-4-methoxybenzene

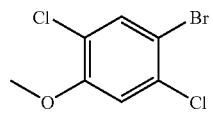

Methyl iodide (1.861 mL, 29.76 mmol) was added to a stirred suspension of 4-bromo-2,5-dichlorophenol (4.8 g, 19.84 mmol) and potassium carbonate (8.23 g, 59.53 mmol) in DMF (20 mL) at ambient temperature under air. The resulting suspension was stirred at 50° C. for 90 minutes. The reaction mixture was allowed to cool and diluted with EtOAc (200 mL), and washed sequentially with saturated brine (2×150 mL) and water (100 mL). The organic layer was dried over MgSO₄, filtered and evaporated to afford crude product. The crude product was purified by flash silica chromatography, elution gradient 0 to 20% EtOAc in isohexane. Pure fractions were evaporated to dryness to afford 1-bromo-2,5-dichloro-4-methoxybenzene (3.82 g, 75%) as a brown solid.

$^1$H NMR (400.132 MHz, CDCl₃) δ 3.89 (3H, s), 7.02 (1H, s), 7.59 (1H, s)

Example 5

2-(4'-(6-Carbamoyl-3,5-dimethylpyrazin-2-yl)-2-(trifluoromethyl)biphenyl-4-yl)acetic acid

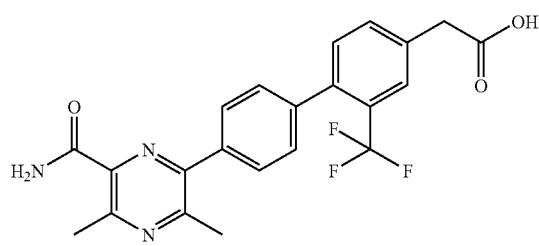

A solution of 4-(6-carbamoyl-3,5-dimethylpyrazin-2-yl)phenylboronic acid (Intermediate 5-1; 278 mg, 1.02 mmol) and methyl 2-(3-(trifluoromethyl)-4-(trifluoromethylsulfonyloxy)phenyl)acetate (Intermediate 5-2; 300 mg, 0.82 mmol) and sodium carbonate (0.666 mL, 1.33 mmol), tetrakis(triphenylphosphine)palladium(0) (58.7 mg, 0.05 mmol) and lithium chloride (60.8 mg, 1.43 mmol) in DME (20 mL) was degassed and then stirred at 85° C. for 17 hours. The reaction mixture was The reaction mixture was acidified with 2M HCl and evaporated. The precipitate was collected by filtration, washed with water (20 mL) and dried under vacuum to afford 2-(4'-(6-carbamoyl-3,5-dimethylpyrazin-2-yl)-2-(trifluoromethyl)biphenyl-4-yl)acetic acid (197 mg, 55.9%) as a brown solid, which was purified by flash silica chromatography, elution gradient 0 to 6% MeOH in DCM. Failed to purify material so was further purified by preparative HPLC (Waters XBridge Prep C18 OBD column, 5μ silica, 50 mm diameter, 150 mm length), using decreasingly polar mixtures of water (containing 1% formic acid) and MeCN as eluents. Fractions containing the desired compound were evaporated to dryness to afford 2-(4'-(6-carbamoyl-3,5-dimethylpyrazin-2-yl)-2-(trifluoromethyl)biphenyl-4-yl)acetic acid (197 mg, 55.9%) as a white solid.

$^1$H NMR (400.132 MHz, DMSO) δ 2.64 (3H, s), 2.75 (3H, s), 3.79 (2H, s), 7.41-7.46 (3H, m), 7.62-7.64 (2H, m), 7.77 (1H, s), 7.83 (2H, d), 8.04 (1H, s), 12.51 (1H, s). m/z (ES+) (M+H)+=430

Intermediate 5-1: 4-(6-Carbamoyl-3,5-dimethylpyrazin-2-yl)phenylboronic acid

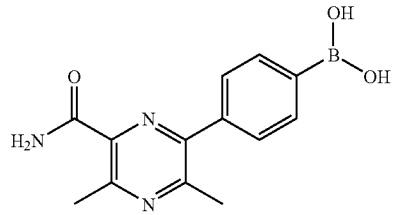

Sodium periodate (19.64 g, 91.81 mmol) was added in one portion to 3,5-dimethyl-6-(4-(4,4,5,5-tetramethyl-1,3,2-dioxaborolan-2-yl)phenyl)pyrazine-2-carboxamide (Intermediate 7-6; 10.81 g, 30.60 mmol) in THF (320 mL) and water (80 mL) and the resulting cloudy suspension was stirred at ambient temperature for 30 minutes. 1M hydrochloric acid (21.42 mL, 21.42 mmol) was added and the resulting suspension was stirred at ambient temperature for 17 hours. The reaction mixture was evaporated and diluted with water (100 mL) and the precipitate was collected by filtration, washed with water (400 mL) and dried under vacuum at 65° C. over 4 hours to afford 4-(6-carbamoyl-3,5-dimethylpyrazin-2-yl)phenylboronic acid (7.13 g, 86%) as a white solid, which was used without further purification.

$^1$H NMR (400.132 MHz, DMSO) δ 2.58 (3H, s), 2.74 (3H, s), 7.60 (1H, s), 7.69 (2H, d), 7.91 (2H, d), 7.98 (1H, s), 8.13 (2H, s). m/z (ES+) (M+H)+=272

Intermediate 5-2: Methyl 2-(3-(trifluoromethyl)-4-(trifluoromethylsulfonyloxy)phenyl)acetate

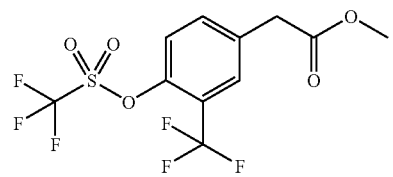

Triethylamine (1.964 mL, 14.09 mmol) was added dropwise to a stirred solution of methyl 2-(4-hydroxy-3-(trifluoromethyl)phenyl)acetate (Intermediate 5-3; 1.10 g, 4.70 mmol) and trifluoromethanesulphonic anhydride (1.156 mL, 7.05 mmol) in DCM (20 mL) at 0° C., over a period of 3 minutes under nitrogen. The resulting solution was stirred at 0° C. for 90 minutes. The reaction mixture was diluted with DCM (100 mL), and washed sequentially with saturated NaHCO₃ (75 mL) and saturated brine (75 mL). The organic layer was dried over MgSO₄, filtered and evaporated to afford crude product. The crude product was purified by flash silica chromatography, elution gradient 0 to 20% EtOAc in isohexane. Pure fractions were evaporated to dryness to afford methyl 2-(3-(trifluoromethyl)-4-(trifluoromethylsulfonyloxy)phenyl)acetate (1.410 g, 82%) as a yellow oil which solidified on standing.

¹H NMR (400.132 MHz, CDCl₃) δ 3.71 (2H, s), 3.74 (3H, s), 7.47 (1H, d), 7.57-7.60 (1H, m), 7.67 (1H, s). m/z (ES−) (M−H)−=365

Intermediate 5-3: Methyl 2-(4-hydroxy-3-(trifluoromethyl)phenyl)acetate

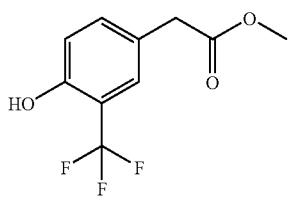

Boron tribromide (8.02 mL, 84.87 mmol) was added dropwise to 2-(4-methoxy-3-(trifluoromethyl)phenyl)acetic acid (3.31 g, 14.13 mmol) in dichloromethane (250 mL) while maintaining the temperature below 10° C. After complete addition the reaction mixture was removed from the ice bath and allowed to stir at ambient temperature under nitrogen for 90 minutes. The reaction mixture was added dropwise to ice cold methanol (150 mL) and the mixture was stirred at ambient temperature for a further 40 minutes. The reaction mixture was evaporated to afford to afford crude product. The crude product was purified by flash silica chromatography, elution gradient 0 to 20% EtOAc in isohexane. Pure fractions were evaporated to dryness to afford methyl 2-(4-hydroxy-3-(trifluoromethyl)phenyl)acetate (1.100 g, 33.2%) as a pale yellow oil.

¹H NMR (400.132 MHz, CDCl₃) δ 3.59 (2H, s), 3.71 (3H, s), 5.71 (1H, s), 6.88 (1H, d), 7.30-7.34 (1H, m), 7.40-7.41 (1H, m). m/z (ES−) (M−H)−=233

Example 6

2-(4'-(6-Carbamoyl-3,5-dimethylpyrazin-2-yl)-2,2'-difluorobiphenyl-4-yl)acetic acid

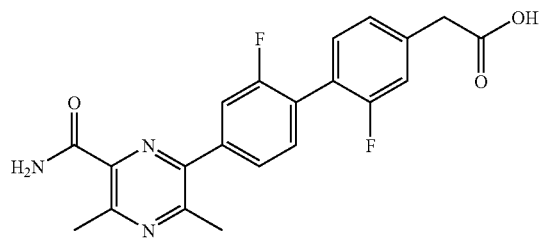

Powdered potassium hydroxide (96 mg, 1.71 mmol) was added in one portion to methyl 2-(4'-(6-carbamoyl-3,5-dimethylpyrazin-2-yl)-2,2'-difluorobiphenyl-4-yl)acetate (Intermediate 6-1; 234 mg, 0.57 mmol) in tert-butanol (10 mL) at 45° C. The resulting solution was stirred at 45° C. for 30 minutes, 2M HCl (2 mL) was added and the mixture was evaporated to remove the organic solvent. The suspension was collected by filtration, washed with water (5 mL) and dried under vacuum to afford crude product. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 2-(4'-(6-carbamoyl-3,5-dimethylpyrazin-2-yl)-2,2'-difluorobiphenyl-4-yl)acetic acid (132 mg, 58.5%) as a white solid.

¹H NMR (400.132 MHz, DMSO) δ 2.66 (3H, s), 2.77 (3H, s), 3.69 (2H, s), 7.23-7.29 (2H, m), 7.46 (1H, t), 7.58 (1H, t), 7.62 (1H, s), 7.71 (1H, d), 7.80 (1H, d), 8.10 (1H, s), 12.49 (1H, s). m/z (ES+) (M+H)+=398

Intermediate 6-1: Methyl 2-(4'-(6-carbamoyl-3,5-dimethylpyrazin-2-yl)-2,2'-difluorobiphenyl-4-yl)acetate

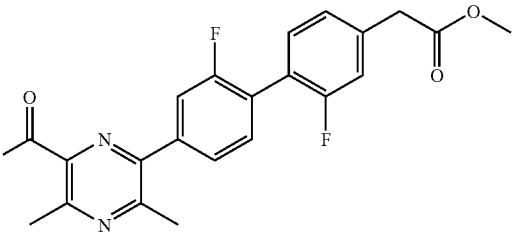

A solution of 4-(6-carbamoyl-3,5-dimethylpyrazin-2-yl)-2-fluorophenyl trifluoromethanesulfonate (Intermediate 6-4; 302 mg, 0.77 mmol) and methyl 2-(3-fluoro-4-(4,4,5,5-tetramethyl-1,3,2-dioxaborolan-2-yl)phenyl)acetate (Intermediate 6-2; 226 mg, 0.77 mmol) and potassium phosphate, tri-basic (196 mg, 0.92 mmol) in DME (10 mL), methanol (5 mL) and water (2.5 mL) was thoughroughly degassed. The mixture was treated with PdCl₂(dppf)-DCM adduct (31.4 mg, 0.04 mmol), degassed again and the atmosphere replaced with nitrogen before being heated to 90° C. for 4 hours. The reaction mixture was allowed to cool to room temperature and then evaporated. The crude product was partitioned between EtOAc (75 mL), and saturated brine (75 mL). The organic layer was dried over MgSO₄, filtered and evaporated to afford crude product. The crude product was purified by flash silica chromatography, elution gradient 0 to 70% EtOAc in isohexane. Pure fractions were evaporated to dryness to afford methyl 2-(4'-(6-carbamoyl-3,5-dimethylpyrazin-2-yl)-2,2'-difluorobiphenyl-4-yl)acetate (240 mg, 76%) as a cream solid.

¹H NMR (400.132 MHz, DMSO) δ 2.66 (3H, s), 2.77 (3H, s), 3.66 (3H, s), 3.81 (2H, s), 7.24-7.31 (2H, m), 7.48 (1H, t), 7.58 (1H, t), 7.62 (1H, s), 7.71 (1H, d), 7.80 (1H, d), 8.10 (1H, s). m/z (ES+) (M+H)+=412

Intermediate 6-2: Methyl 2-(3-fluoro-4-(4,4,5,5-tetramethyl-1,3,2-dioxaborolan-2-yl)phenyl)acetate

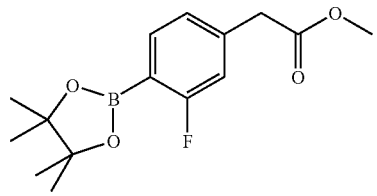

To a degassed solution of methyl 2-(3-fluoro-4-(trifluoromethylsulfonyloxy)phenyl)acetate (Intermediate 6-3; 1.82 g, 5.76 mmol) in dioxane (35 mL) was added potassium acetate (1.751 g, 17.84 mmol), bis(pinacolato)diboron (2.192 g, 8.63 mmol), 1,1'-bis(diphenylphosphino)ferrocene (0.194 g, 0.35 mmol) and PdCl$_2$(dppf)-CH$_2$Cl$_2$ adduct (0.282 g, 0.35 mmol). The suspension was degassed and then heated, under nitrogen, to 80° C. overnight. The reaction mixture was allowed to cool, evaporated and the residue suspended in EtOAc. This was passed through a silica pad (3" diameter×1" deep) washing with EtOAc. The filtrate was evaporated to afford crude product. The crude product was purified by flash silica chromatography, elution gradient 0 to 20% EtOAc in isohexane. Pure fractions were evaporated to dryness to afford methyl 2-(3-fluoro-4-(4,4,5,5-tetramethyl-1,3,2-dioxaborolan-2-yl)phenyl)acetate (1.340 g, 79%) as a colourless oil.
¹H NMR (400.132 MHz, CDCl$_3$) δ 1.35 (12H, s), 3.62 (2H, s), 3.69 (3H, s), 6.98 (1H, d), 7.05 (1H, d), 7.69 (1H, t). m/z GCMS (EI+) M+=294

Intermediate 6-3: Methyl 2-(3-fluoro-4-(trifluoromethylsulfonyloxy)phenyl)acetate

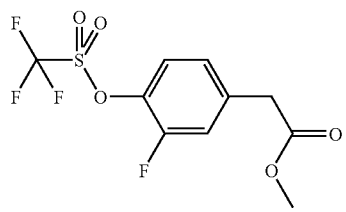

Trifluoromethanesulphonic anhydride (2.67 mL, 16.29 mmol) was added dropwise to a stirred solution of methyl 2-(3-fluoro-4-hydroxyphenyl)acetate (2 g, 10.86 mmol) in DCM (47.1 mL) cooled to 0° C., over a period of 5 minutes under nitrogen. Triethylamine (4.54 mL, 32.58 mmol) was added dropwise over 5 minutes and the resulting solution stirred at rambient temperature for 4 hours under nitrogen. The reaction mixture was diluted with DCM (100 mL), and washed sequentially with water (100 mL), saturated NaHCO$_3$ (100 mL), and water (100 mL). The organic layer was dried by passing through a phase seperating cartridge and evaporated to afford crude product. The crude product was purified by flash silica chromatography, elution gradient 0 to 20% EtOAc in isohexane. Pure fractions were evaporated to dryness to afford methyl 2-(3-fluoro-4-(trifluoromethylsulfonyloxy)phenyl)acetate (2.250 g, 65.5%) as a straw yellow oil.
¹H NMR (400.13 MHz, CDCl$_3$) δ 3.64 (2H, s), 3.73 (3H, s), 7.11-7.14 (1H, m), 7.22-7.31 (2H, m). m/z (ES-) (M-H)-=315.19

Intermediate 6-4: 4-(6-Carbamoyl-3,5-dimethylpyrazin-2-yl)-2-fluorophenyl trifluoromethanesulfonate

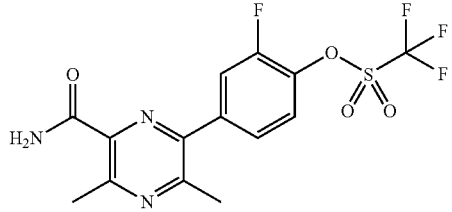

6-(3-Fluoro-4-hydroxyphenyl)-3,5-dimethylpyrazine-2-carboxamide (Intermediate 6-5; 450 mg, 1.72 mmol), 1,1,1-trifluoro-N-phenyl-N-(trifluoromethylsulfonyl)methanesulfonamide (615 mg, 1.72 mmol) and potassium carbonate (714 mg, 5.17 mmol) were suspended in THF (15 mL) and sealed into a microwave tube. The reaction was heated to 120° C. for 8 minutes in the microwave reactor and cooled to RT. The suspension was filtered, the solid was washed with EtOAc (20 mL) and the filtrate was evaporated to afford crude product. The crude product was purified by flash silica chromatography, elution gradient 10 to 60% EtOAc in isohexane. Pure fractions were evaporated to dryness to afford 4-(6-carbamoyl-3,5-dimethylpyrazin-2-yl)-2-fluorophenyl trifluoromethanesulfonate (508 mg, 75.0%) as a white solid.
¹H NMR (400.132 MHz, DMSO) δ 2.62 (3H, s), 2.76 (3H, s), 7.63 (1H, s), 7.77-7.85 (2H, m), 8.09 (1H, d), 8.12 (1H, s). m/z (ES+) (M+H)+=394

Intermediate 6-5: 6-(3-Fluoro-4-hydroxyphenyl)-3,5-dimethylpyrazine-2-carboxamide

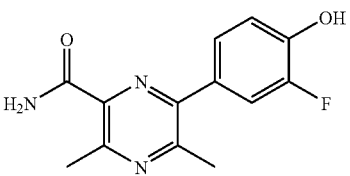

A solution of 6-chloro-3,5-dimethylpyrazine-2-carboxamide (Intermediate A) (492 mg, 2.65 mmol) and 2-fluoro-4-(4,4,5,5-tetramethyl-1,3,2-dioxaborolan-2-yl)phenol (Intermediate 6-6; 630 mg, 2.65 mmol) and potassium phosphate, tri-basic (674 mg, 3.18 mmol) in DME (10 mL), ethanol (5 mL) and water (2.5 mL) was thoughroughly degassed. The mixture was treated with PdCl$_2$(dppf)-DCM adduct (108 mg, 0.13 mmol), degassed again and the atmosphere replaced with nitrogen before being heated to 80° C. for 4 hours. The reaction mixture was allowed to cool to room temperature and then evaporated. The crude product was partitioned between EtOAc (75 mL), and 1N citric acid (25 mL) and the precipitate was collected by filtration, washed with water (10 mL) and air dried to afford 6-(3-fluoro-4-hydroxyphenyl)-3,5- dimethylpyrazine-2-carboxamide (481 mg, 69.6%) as a beige solid, which was used without further purification.

¹H NMR (400.132 MHz, DMSO) δ 2.66 (3H, s), 2.78 (3H, s), 7.11 (1H, t), 7.47 (1H, d), 7.65 (1H, s), 7.70 (1H, d), 8.09 (1H, s), 10.24 (1H, s). m/z (ES+) (M+H)+=262

Intermediate 6-6: 2-Fluoro-4-(4,4,5,5-tetramethyl-1,3,2-dioxaborolan-2-yl)phenol

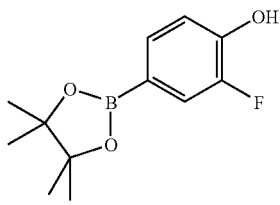

A solution of 4-bromo-2-fluorophenol (1.032 mL, 9.42 mmol) in dioxane (60.2 mL) was degassed with nitrogen for a period of 10 minutes. Potassium acetate (3.70 g, 37.70 mmol), 4,4,4',4',5,5,5',5'-octamethyl-2,2'-bi(1,3,2-dioxaborolane) (3.59 g, 14.14 mmol), (1,1'-bis(diphenylphosphino)ferrocene)-dichloropalladium(II) (0.465 g, 0.57 mmol) and 1,1'-bis(diphenylphosphino)ferrocene (0.317 g, 0.57 mmol) were added. The resulting mixture was stirred at 85° C. under nitrogen for 17 hours (overnight). The reaction mixture was concentrated and diluted with EtOAc (100 mL), and the mixture was acidified with 1N citric acid (75 mL) and the mixture was filtered through celite. The aqueous phase was separated and extracted with EtOAc (150 mL) and organic extracts were combined, washed with saturated brine (150 mL), dried over MgSO₄, filtered and evaporated to afford crude product which was filtered through a pad of silica, washing through with EtOAc. The filtrate was evaporated to afford crude product. The crude product was purified by flash silica chromatography, elution gradient 0 to 20% EtOAc in isohexane. Pure fractions were evaporated to dryness to afford 2-fluoro-4-(4,4,5,5-tetramethyl-1,3,2-dioxaborolan-2-yl)phenol (2.020 g, 90%) as a pale brown oil which solidified on standing.

¹H NMR (400.132 MHz, CDCl₃) δ 1.33 (12H, s), 5.38 (1H, s), 6.98 (1H, t), 7.47-7.51 (2H, m). m/z (ES−) (M−H)−=237

Example 7

1-(4'-(6-Carbamoyl-3,5-dimethylpyrazin-2-yl)-2-chlorobiphenyl-4-yl)cyclobutanecarboxylic acid

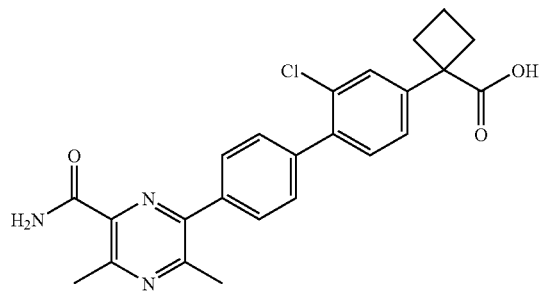

Powdered potassium hydroxide (56.9 mg, 1.01 mmol) was added in one portion to methyl 1-(4'-(6-carbamoyl-3,5-dimethylpyrazin-2-yl)-2-chlorobiphenyl-4-yl)cyclobutanecarboxylate (Intermediate 7-1; 152 mg, 0.34 mmol)/in tert-butanol (10 mL) at 40° C. under nitrogen. The resulting suspension was stirred at 40° C. for 1 hour LCMS showed the reaction was complete. The reaction mixture was quenched with HCl (2.027 mL, 2.03 mmol) in ethanol (10 mL) and the resulting solution stirred for a further 20 minutes before being evaporated to dryness. The resulting solid was washed with water (50 mL) and dried in a dessicator to afford 1-(4'-(6-carbamoyl-3,5-dimethylpyrazin-2-yl)-2-chlorobiphenyl-4-yl)cyclobutanecarboxylic acid (68.0 mg, 46.2%) as a cream solid.

¹H NMR (400 MHz, CDCl₃) 1.91-2.01 (1H, m), 2.11-2.20 (1H, m), 2.55-2.63 (2H, m), 2.73 (3H, s), 2.89-2.96 (2H, m), 3.00 (3H, s), 5.84 (1H, s), 7.31-7.33 (1H, m), 7.38 (1H d, J=8.0 Hz), 7.48 (1H d, J=1.8 Hz), 7.57-7.59 (2H, m), 7.65-7.67 (2H, m), 7.84 (1H, s). m/z (ES+) (M+H)+=436.16

Intermediate 7-1: Methyl 1-(4'-(6-carbamoyl-3,5-dimethylpyrazin-2-yl)-2-chlorobiphenyl-4-yl)cyclobutanecarboxylate

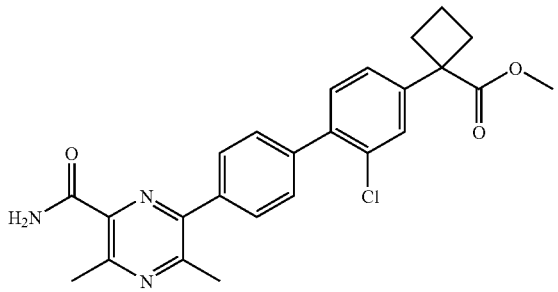

A solution of 4-(6-carbamoyl-3,5-dimethylpyrazin-2-yl) phenyl trifluoromethanesulfonate (Intermediate 7-4; 289 mg, 0.77 mmol) and methyl 1-(3-chloro-4-(4,4,5,5-tetramethyl-1,3,2-dioxaborolan-2-yl)phenyl)cyclobutanecarboxylate (Intermediate 7-2; 270 mg, 0.77 mmol) and potassium phosphate, tri-basic (196 mg, 0.92 mmol) in DME (10 mL), MeOH (5 mL) and water (2.5 mL) was thoughroughly degassed. The mixture was treated with PdCl₂(dppf)-DCM adduct (31.4 mg, 0.04 mmol), degassed again and the atmosphere replaced with nitrogen before being heated to 90° C. for 4 hours. The reaction mixture was allowed to cool, diluted with EtOAc (40 mL) and water (20 mL). This was passed through a silica pad washing with EtOAc. The filtrate was separated and washed with brine (20 mL) then evaporated to afford crude product. The crude product was purified by flash silica chromatography, elution gradient 0 to 70% EtOAc in isohexane. Pure fractions were evaporated to dryness to afford methyl 1-(4'-(6-carbamoyl-3,5-dimethylpyrazin-2-yl)-2-chlorobiphenyl-4-yl)cyclobutanecarboxylate (239 mg, 69.0%) as a colourless gum.

¹H NMR (400 MHz, CDCl₃) δ 1.90-1.98 (1H, m), 2.06-2.14 (1H, m), 2.51-2.58 (2H, m), 2.73 (3H, s), 2.85-2.91 (2H, m), 3.00 (3H s), 3.71 (3H, s), 5.45 (1H, s), 7.27-7.29 (1H, m), 7.36 (1H d, J=8.0 Hz), 7.44 (1H d, J=1.8 Hz), 7.57-7.59 (2H, m), 7.65-7.67 (2H, m), 7.81 (1H, s). m/z (ES+) (M+H)+=450.14

Intermediate 7-2: Methyl 1-(3-chloro-4-(4,4,5,5-tetramethyl-1,3,2-dioxaborolan-2-yl)phenyl)cyclobutanecarboxylate

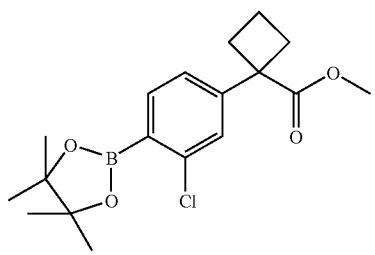

Lithium bis(trimethylsilyl)amide (0.872 mL, 0.87 mmol) was added dropwise to methyl 5-bromo-2-(3-chloro-4-(4,4,5,5-tetramethyl-1,3,2-dioxaborolan-2-yl)phenyl)pentanoate (Intermediate 7-3; 342 mg, 0.79 mmol) in THF (10 mL) cooled to 0° C. under nitrogen the reaction and was stirred at 0° C. for 12 hours. The reaction mixture was quenched with saturated NH4Cl (50 mL) and was diluted with EtOAc (75 mL). The organic layer was separated and re-extracted with EtOAc (75 mL). The combined organics were washed with saturated brine (50 mL), dried (MgSO₄), filtered and concentrated to afford crude product. The crude product was purified by flash silica chromatography, elution gradient 0 to 30% EtOAc in isohexane. Pure fractions were evaporated to dryness to afford methyl 1-(3-chloro-4-(4,4,5,5-tetramethyl-1,3,2-dioxaborolan-2-yl)phenyl)cyclobutanecarboxylate (273 mg, 98%) as a colourless gum.

$^1$H NMR (400 MHz, CDCl$_3$) δ 1.20 (12H, s), 1.69-1.73 (1H, m), 1.85-1.91 (1H, m), 2.28-2.35 (2H, m), 2.62-2.68 (2H, m), 3.47 (3H, s), 6.98-7.00 (1H, m), 7.11 (1H d, J=11.9 Hz), 7.49 (1H d, J=7.8 Hz)

Intermediate 7-3: Methyl 5-bromo-2-(3-chloro-4-(4,4,5,5-tetramethyl-1,3,2-dioxaborolan-2-yl)phenyl) pentanoate

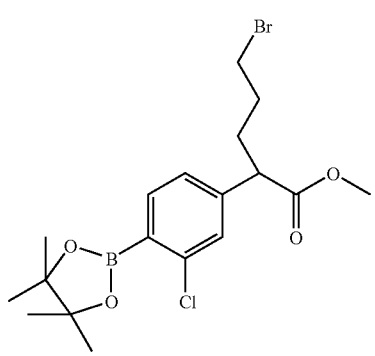

Sodium hydride (0.153 g, 3.83 mmol) was added in one portion to methyl 2-(3-chloro-4-(4,4,5,5-tetramethyl-1,3,2-dioxaborolan-2-yl)phenyl)acetate (Intermediate 2-7; 1.08 g, 3.48 mmol) in DMF (20 mL) cooled to 0° C. under nitrogen. The resulting solution was stirred at 0° C. for 10 minutes. 1,3-Dibromopropane (0.392 mL, 3.83 mmol) was added to the reaction and was stirred at 0° C. for 5 minutes. Sodium hydride (0.153 g, 3.83 mmol) was added in one portion to the reaction and stir at 0° C. for 1 hour. The reaction mixture was quenched with saturated NH₄Cl (50 mL). The reaction mixture was diluted with EtOAc (75 mL), and washed sequentially with water (4×50 mL) and saturated brine (50 mL). dried over MgSO₄ The organic layer was evaporated to afford crude product. The crude product was purified by flash silica chromatography, elution gradient 0 to 30% EtOAc in isohexane. Pure fractions were evaporated to dryness to afford methyl 5-bromo-2-(3-chloro-4-(4,4,5,5-tetramethyl-1,3,2-dioxaborolan-2-yl)phenyl)pentanoate (0.362 g, 24.12%) as a colourless gum.

$^1$H NMR (400 MHz, CDCl$_3$) 1.36 (12H, s), 1.71-1.86 (2H, m), 1.87-2.00 (1H, m), 2.14-2.23 (1H, m), 3.36 (2H t, J=6.7 Hz), 3.52 (1H t, J=7.7 Hz), 3.64 (3H, s), 7.13-7.17 (1H, m), 7.29 (1H q, J=1.7 Hz), 7.65 (1H d, J=7.7 Hz)

Intermediate 7-4: 4-(6-Carbamoyl-3,5-dimethylpyrazin-2-yl)phenyl trifluoromethanesulfonate

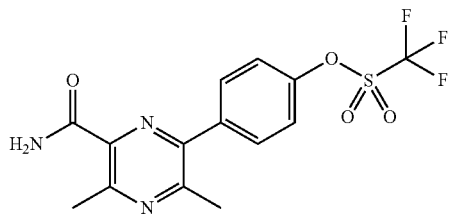

6-(4-Hydroxyphenyl)-3,5-dimethylpyrazine-2-carboxamide (Intermediate 7-5; 22 g, 90.44 mmol), 1,1,1-trifluoro-N-phenyl-N-(trifluoromethylsulfonyl)methanesulfonamide (32.3 g, 90.44 mmol) and potassium carbonate (37.5 g, 271.31 mmol) were suspended in THF (611 mL) and stirred for 16 hours. The suspension was filtered, the solid was washed with EtOAc (250 mL) and the filtrate was evaporated to afford crude product. The crude product was purified by flash silica chromatography, elution gradient 0 to 80% EtOAc in isohexane. Pure fractions were evaporated to dryness to afford 4-(6-carbamoyl-3,5-dimethylpyrazin-2-yl)phenyl trifluoromethanesulfonate (34.5 g, 102%) as a cream solid.

$^1$H NMR (400 MHz, DMSO-d6) 2.59 (3H, s), 2.75 (3H, s), 7.62-7.64 (3H, m), 7.93-7.97 (2H, m), 8.05 (1H, s). m/z (ES+) (M+H)+=376.03

Intermediate 7-5: 6-(4-Hydroxyphenyl)-3,5-dimethylpyrazine-2-carboxamide

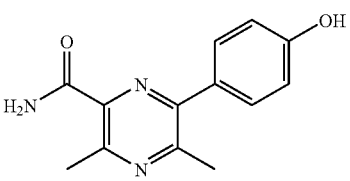

A solution of 6-chloro-3,5-dimethylpyrazine-2-carboxamide (Intermediate A) (20.17 g, 108.67 mmol), 4-(4,4,5,5-tetramethyl-1,3,2-dioxaborolan-2-yl)phenol (26.3 g, 119.53 mmol) and tripotassium phosphate (34.6 g, 163.00 mmol) in DME (500 mL), MeOH (250 mL) and water (125 mL) was degassed before addition of (1,1'-bis(diphenylphosphino)ferrocene)-dichloropalladium(II) (DCM adduct) (4.47 g, 5.43 mmol). The reaction mixture was heated to 80° C., under nitrogen, and left to stir for 1 hour. The reaction mixture was allowed to cool to room temperature and then evaporated. The residue was partitioned between water (1 L), 2M HCl aq. (1 L) and EtOAc (1 L). The aqueous was re-extracted with EtOAc (2 L) and the combined organics washed with brine (1 L), dried (MgSO$_4$) and evaporated to give crude product. The aqueous was filtered and the solid was washed with water (2 L) to give pure product. The crude product from the organic layer was purified by flash silica chromatography, elution gradient 20 to 80% EtOAc in isohexane. Pure fractions were evaporated to dryness to afford 6-(4-hydroxyphenyl)-3,5-dimethylpyrazine-2-carboxamide (22.00 g, 83%) as a cream solid.

$^1$H NMR (400 MHz, DMSO-d6) 2.58 (3H, s), 2.71 (3H, s), 6.85-6.89 (2H, m), 7.56-7.60 (3H, m), 7.95 (1H, s), 9.72 (1H, s). m/z (ES+) (M+H)+=244.19

Intermediate 7-6: 3,5-Dimethyl-6-(4-(4,4,5,5-tetramethyl-1,3,2-dioxaborolan-2-yl)phenyl)pyrazine-2-carboxamide

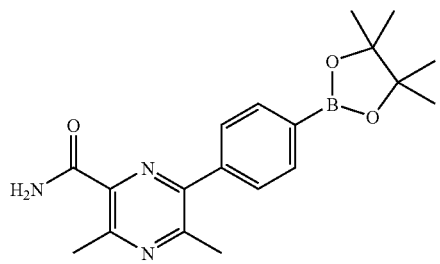

[1,1'-Bis(diphenylphosphino)ferrocene]dichloropalladium(ii), complex with dichloromethane (1:1) (2.59 g, 3.20 mmol) was added to 4-(6-carbamoyl-3,5-dimethylpyrazin-2-yl)phenyl trifluoromethanesulfonate (Intermediate 7-4; 20 g, 53.29 mmol), 4,4,4',4',5,5,5',5'-octamethyl-2,2'-bi(1,3,2-dioxaborolane) (14.88 g, 58.62 mmol), potassium acetate (15.69 g, 159.86 mmol) and 1,1'-bis(diphenylphosphino)ferrocene (1.747 g, 3.20 mmol) in dioxane (239 mL) at RT over a period of 5 minutes under nitrogen. The resulting suspension was degassed and refilled with nitrogen then stirred at 80° C. for 17 hours. The reaction mixture was cooled to RT, diluted with EtOAc and Water, The organic layer was collected, washed with brine and evaporated to a brown oil which solidified on standing. The crude product was purified by flash silica chromatography, elution gradient 20 to 80% EtOAc in isohexane. Pure fractions were evaporated to dryness to afford 3,5-dimethyl-6-(4-(4,4,5,5-tetramethyl-1,3,2-dioxaborolan-2-yl)phenyl)pyrazine-2-carboxamide (17.20 g, 91%) as a cream solid.

$^1$H NMR (400 MHz, CDCl$_3$) 1.38 (12H, s), 2.65 (3H, s), 2.99 (3H, s), 5.45 (1H, s), 7.56-7.59 (2H, m), 7.78 (1H, s), 7.93-7.95 (2H, m). m/z (ES+) (M+H)+=354.22

Example 8

(S)-2-(4'-(6-Carbamoyl-3,5-dimethylpyrazin-2-yl)-2-chlorobiphenyl-4-yl)propanoic acid and

Example 9

(R)-2-(4'-(6-Carbamoyl-3,5-dimethylpyrazin-2-yl)-2-chlorobiphenyl-4-yl)propanoic acid

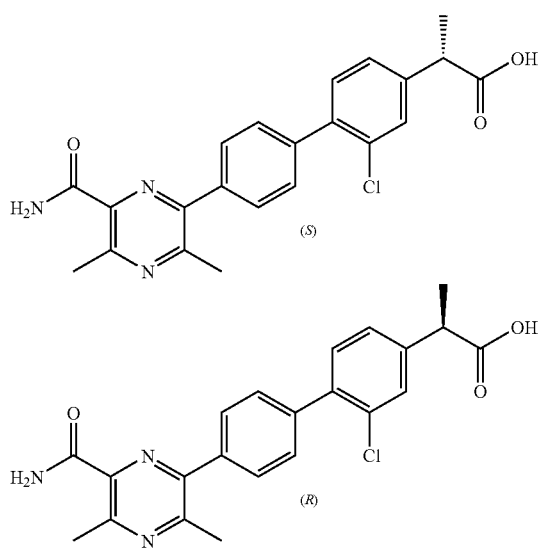

Powdered potassium hydroxide (331 mg, 5.90 mmol) was added in one portion to methyl 2-(4'-(6-carbamoyl-3,5-dimethylpyrazin-2-yl)-2-chlorobiphenyl-4-yl)propanoate (Intermediate 8-1; 834 mg, 1.97 mmol) in tert-butanol (20 mL) at 45° C. The resulting solution was stirred at 45° C. for 30 minutes. 2M HCl (6 mL) was added and the mixture was evaporated to remove the organic solvent. The suspension was collected by filtration, washed with water and dried under vacuum to afford crude product. The crude product was purified by flash silica chromatography, elution gradient 0 to 10% MeOH in DCM. Fractions containing the desired compound were evaporated to dryness to afford racemic 2-(4'-(6-carbamoyl-3,5-dimethylpyrazin-2-yl)-2-chlorobiphenyl-4-yl)propanoic acid (603 mg, 74.8%) as a white solid. This was purified by preparative chiral-HPLC on a OJ column, eluting isocratically with 30% EtOH in isohexane (acidified with AcOH) as eluent. The fractions containing the desired compound were evaporated to dryness to afford:

(R)-2-(4'-(6-carbamoyl-3,5-dimethylpyrazin-2-yl)-2-chlorobiphenyl-4-yl)propanoic acid (first eluted, 0.531 g, 40.8%) as a white solid $^1$H NMR (400 MHz, CDCl$_3$) δ 1.59 (3H, d, J=7.2 Hz), 2.73 (3H, s), 3.00 (3H, s), 3.81 (1H q, J=7.2 Hz), 5.84 (1H, s), 7.32-7.39 (2H, m), 7.50 (1H, s), 7.57 (2H d, J=8.3 Hz), 7.66 (2H d, J=8.3 Hz), 7.84 (1H, s). LCMS: m/z (ES+) (M+H)+=410 and (S)-2-(4'-(6-carbamoyl-3,5-dimethylpyrazin-2-yl)-2-chlorobiphenyl-4-yl)propanoic acid (second eluted, 0.537 g, 41.3%).

¹H NMR (400 MHz, CDCl₃) δ 1.60 (3H, d,), 2.73 (3H, s), 3.00 (3H, s), 3.78-3.82 (1H, m), 5.80 (1H, s), 7.32-7.39 (2H, m), 7.50 (1H, s), 7.57 (2H d, J=8.3 Hz), 7.66 (2H d, J=8.3 Hz), 7.83 (1H, s). LCMS: m/z (ES+) (M+H)+=410

The R-enantiomer (150 mg, 0.37 mmol) was purified by crystallisation from EtOH to afford (R)-2-(4'-(6-carbamoyl-3,5-dimethylpyrazin-2-yl)-2-chlorobiphenyl-4-yl)propanoic acid (56.0 mg, 37.3%) as a pale yellow crystalline solid.

m/z (ES+) (M+H)+=410.

The absolute configuration of the R-enantiomer was deduced by single crystal X-ray crystallography based on the anomalous scattering contribution to the measured diffraction intensities.

Intermediate 8-1: Methyl 2-(4'-(6-carbamoyl-3,5-dimethylpyrazin-2-yl)-2-chlorobiphenyl-4-yl)propanoate

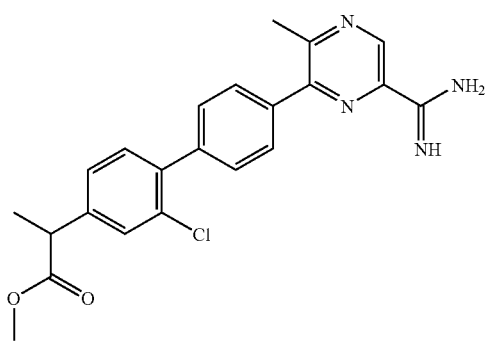

A solution of 4-(6-carbamoyl-3,5-dimethylpyrazin-2-yl)phenyl trifluoromethanesulfonate (Intermediate 7-4; 1.249 g, 3.33 mmol) and methyl 2-(3-chloro-4-(4,4,5,5-tetramethyl-1,3,2-dioxaborolan-2-yl)phenyl)propanoate (Intermediate 8-2; 1.08 g, 3.33 mmol) and potassium phosphate, tri-basic (0.847 g, 3.99 mmol) in DME (16 mL), methanol (8.00 mL) and water (4.00 mL) was thoughroughly degassed. The mixture was treated with PdCl₂(dppf)-DCM adduct (0.136 g, 0.17 mmol), degassed again and the atmosphere replaced with nitrogen before being heated to 90° C. for 4 hours in the microwave. The reaction mixture was allowed to cool to room temperature and then evaporated. The crude product was partitioned between EtOAc (75 mL), and saturated brine (75 mL). The organic layer was dried over MgSO₄, filtered and evaporated to afford crude product. The crude product was purified by flash silica chromatography, elution gradient 0 to 70% EtOAc in isohexane. Pure fractions were evaporated to dryness to afford methyl 2-(4'-(6-carbamoyl-3,5-dimethylpyrazin-2-yl)-2-chlorobiphenyl-4-yl)propanoate (0.841 g, 59.6%) as a beige solid.

¹H NMR (400 MHz, CDCl₃) 1.56 (3H d, J=7.2 Hz), 2.73 (3H, s), 3.00 (3H, s), 3.72 (3H, s), 3.77 (1H q, J=7.2 Hz), 5.47 (1H, s), 7.28-7.31 (1H, m), 7.46 (1H d, J=1.8 Hz), 7.35-7.81 (2H, m), 7.56-7.59 (2H, m), 7.65-7.68 (2H, m). m/z (ES+) (M+H)+=424

Intermediate 8-2: methyl 2-(3-chloro-4-(4,4,5,5-tetramethyl-1,3,2-dioxaborolan-2-yl)phenyl)propanoate

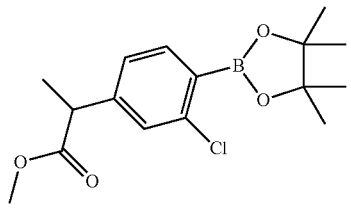

Lithium bis(trimethylsilyl)amide (7.79 mL, 7.79 mmol) was added to methyl 2-(3-chloro-4-(4,4,5,5-tetramethyl-1,3,2-dioxaborolan-2-yl)phenyl)acetate (Intermediate 2-7; 2.2 g, 7.08 mmol) in THF (50 mL) cooled to 0° C. under nitrogen. The resulting solution was stirred at 0° C. for 30 minutes. Next methyl iodide (0.530 mL, 8.50 mmol) was added and the reaction stirred for 30 minutes Ammonium chloride (satd) (50 mL) was added with vigorous stirring, ethyl acetate (100 mL) and water (50 mL) were added and the organic phase separated, washed with water (50 mL) and saturated brine (50 mL). The organic layer was dried over MgSO₄, filtered and evaporated to afford crude product. The crude product was purified by flash silica chromatography, elution gradient 0 to 40% EtOAc in isohexane. Pure fractions were evaporated to dryness to afford methyl 2-(3-chloro-4-(4,4,5,5-tetramethyl-1,3,2-dioxaborolan-2-yl)phenyl)propanoate (1.290 g, 56.1%) as a colourless oil.

¹H NMR (400 MHz, CDCl₃) 1.36 (12H, s), 1.48 (3H d, J=7.2 Hz), 3.65 (3H, s), 3.65-3.69 (1H, m), 7.15-7.17 (1H, m), 7.29 (1H d, J=1.7 Hz), 7.65 (1H d, J=7.7 Hz)

Example 10

1-(4'-(6-Carbamoyl-3,5-dimethylpyrazin-2-yl)-2-chlorobiphenyl-4-yl)cyclopropanecarboxylic acid

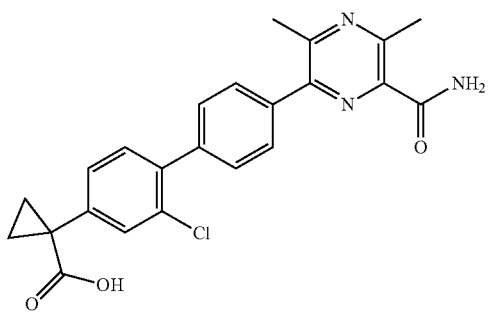

Powdered potassium hydroxide (52.1 mg, 0.93 mmol) was added in one portion to methyl 1-(4'-(6-carbamoyl-3,5-dimethylpyrazin-2-yl)-2-chlorobiphenyl-4-yl)cyclopropanecarboxylate (Intermediate 10-1; 135 mg, 0.31 mmol) in tert-butanol (5 mL) at 45° C. The resulting solution was stirred at 45° C. for 30 minutes. 2N HCl (1 mL) was added and the mixture was evaporated to remove the organic solvent. The suspension was collected by filtration, washed with water and dried under vacuum to afford crude product. The crude product was purified by preparative HPLC (Waters XBridge Prep C18 OBD column, 5μ silica, 50 mm diameter, 150 mm length), using decreasingly polar mixtures of water (containing 0.1% TFA) and MeCN as eluents. Fractions containing the desired compound were evaporated to dryness to afford 1-(4'-(6-carbamoyl-3,5-dimethylpyrazin-2-yl)-2-chlorobiphenyl-4-yl)cyclopropanecarboxylic acid (30.0 mg, 22.96%) as a white solid.

$^1$H NMR (400 MHz, DMSO-d6) 1.23-1.25 (2H, m), 1.48-1.51 (2H, m), 2.65 (3H, s), 2.76 (3H, s), 7.41 (2H t, J=7.6 Hz), 7.53-7.58 (3H, m), 7.61 (1H, s), 7.84-7.86 (2H, m), 8.04 (1H, s), 12.47 (1H, s). m/z (ES+) (M+H)+=422

Intermediate 10-1: Methyl 1-(4'-(6-carbamoyl-3,5-dimethylpyrazin-2-yl)-2-chlorobiphenyl-4-yl)cyclopropanecarboxylate

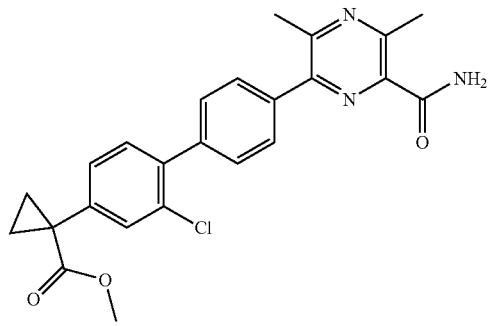

A solution of 4-(6-carbamoyl-3,5-dimethylpyrazin-2-yl) phenyl trifluoromethanesulfonate (Intermediate 7-4; 245 mg, 0.65 mmol) and methyl 1-(3-chloro-4-(4,4,5,5-tetramethyl-1,3,2-dioxaborolan-2-yl)phenyl)cyclopropanecarboxylate (Intermediate 10-2; 220 mg, 0.65 mmol) and potassium phosphate, tri-basic (166 mg, 0.78 mmol) in DME (4 mL), methanol (2 mL) and water (1 mL) was thoughroughly degassed. The mixture was treated with PdCl$_2$(dppf)-DCM adduct (26.7 mg, 0.03 mmol), degassed again and the atmosphere replaced with nitrogen before being heated to 90° C. for 4 hours in the microwave. The reaction mixture was allowed to cool to room temperature and then evaporated. The crude product was partitioned between EtOAc (75 mL), and saturated brine (75 mL). The organic layer was dried over MgSO$_4$, filtered and evaporated to afford crude product. The crude product was purified by flash silica chromatography, elution gradient 0 to 70% EtOAc in isohexane. Pure fractions were evaporated to dryness to afford methyl 1-(4'-(6-carbamoyl-3,5-dimethylpyrazin-2-yl)-2-chlorobiphenyl-4-yl)cyclopropanecarboxylate (141 mg, 49.5%) as a colourless gum.

$^1$H NMR (400 MHz, CDCl$_3$) 1.24-1.27 (2H, m), 1.66-1.69 (2H, m), 2.73 (3H, s), 3.00 (3H, s), 3.69 (3H, s), 5.52 (1H, s), 7.34-7.68 (7H, m), 7.82 (1H, s). m/z (ES+) (M+H)+=436

Intermediate 10-2: Methyl 1-(3-chloro-4-(4,4,5,5-tetramethyl-1,3,2-dioxaborolan-2-yl)phenyl)cyclopropanecarboxylate

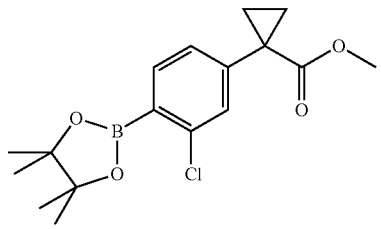

Lithium bis(trimethylsilyl)amide (7.08 mL, 7.08 mmol) was added dropwise to methyl 2-(3-chloro-4-(4,4,5,5-tetramethyl-1,3,2-dioxaborolan-2-yl)phenyl)acetate (1 g, 3.22 mmol) in THF (20 mL) cooled to 0° C. under nitrogen. The resulting solution was stirred at 0° C. for 30 minutes and then 1,2-dibromoethane (0.305 mL, 3.54 mmol) was added to the reaction and was stirred at 0° C. for 5 minutes. The reaction mixture was quenched with saturated NH$_4$Cl (50 mL) and was diluted with EtOAc (75 mL). The organic layer was separated and re-extracted with EtOAc (75 mL). The combined organics were washed with saturated brine (50 mL), dried (MgSO$_4$), filtered and concentrated to afford crude product. The crude product was purified by flash silica chromatography, elution gradient 0 to 30% EtOAc in isohexane. Pure fractions were evaporated to dryness to afford methyl 1-(3-chloro-4-(4,4,5,5-tetramethyl-1,3,2-dioxaborolan-2-yl)phenyl)cyclopropanecarboxylate (0.182 g, 16.79%) as a colourless gum.

$^1$H NMR (400 MHz, CDCl$_3$) δ 1.15-1.18 (2H, m), 1.36 (12H, s), 1.58-1.61 (2H, m), 3.61-3.61 (3H, m), 7.19-7.22 (1H, m), 7.33 (1H d, J=1.6 Hz), 7.64 (1H d, J=7.7 Hz)

Example 11

2-(4'-(6-Carbamoyl-3,5-dimethylpyrazin-2-yl)-2-chlorobiphenyl-4-yl)butanoic acid

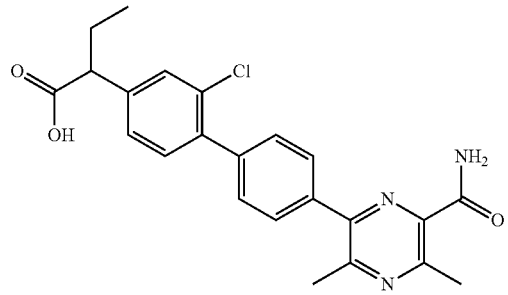

A solution of 4-(6-carbamoyl-3,5-dimethylpyrazin-2-yl) phenyl trifluoromethanesulfonate (Intermediate 11-1; 760 mg, 2.03 mmol) and methyl 2-(3-chloro-4-(4,4,5,5-tetramethyl-1,3,2-dioxaborolan-2-yl)phenyl)butanoate (686 mg, 2.03 mmol) and potassium phosphate, tri-basic (516 mg, 2.43 mmol) in DME (10 mL), ethanol (5 mL) and water (2.5 mL) was thoughroughly degassed. The mixture was treated with PdCl$_2$(dppf)-DCM adduct (83 mg, 0.10 mmol), degassed again and the atmosphere replaced with nitrogen before being heated to 90° C. for 4 hours. The reaction mixture was allowed to cool, diluted with EtOAc (40 mL) and water (20 mL). This was passed through a silica pad washing with EtOAc. The filtrate was separated and washed with brine (20 mL) then evaporated to afford crude product. The crude product was purified by flash silica chromatography, elution gradient 0 to 70% EtOAc in isohexane. Pure fractions were evaporated to dryness to afford a colourless gum, powdered potassium hydroxide (597 mg, 10.63 mmol) was added in one portion to this in tert-butanol (25 mL) at 45° C. under nitrogen. The resulting solution was stirred at 45° C. for 1 hour. The mixture was treated with acetic acid (0.812 mL, 14.18 mmol) in ethanol (20 mL) and stirred at room temperature for 10 minutes. The mixture was then evaporated under vacuum to give an off white solid. This was triturated with water (20 mL), filtered off and washed with water (10 mL), before drying under vacuum to give crude solid. The crude product was purified by flash silica chromatography, elution gradient 0 to 10% MeOH in DCM. Fractions containing the desired compound were evaporated to dryness to afford 2-(4'-(6-carbamoyl-3,5-dimethylpyrazin-2-yl)-2-chlorobiphenyl-4-yl)butanoic acid (42.0 mg, 5.59%) as a white foam.

$^1$H NMR (400.13 MHz, CDCl$_3$) δ 0.93 (3H, t), 1.82 (1H, dt), 2.12 (1H, dt), 2.66 (3H, s), 2.92 (3H, s), 3.48 (1H, t), 6.22 (1H, d), 7.28 (2H, dd), 7.44 (1H, d), 7.51 (2H, dt), 7.58 (2H, dt), 7.79 (1H, d). m/z (ES+) (M+H)+=424.38

Intermediate 11-1: Methyl 2-(3-chloro-4-(4,4,5,5-tetramethyl-1,3,2-dioxaborolan-2-yl)phenyl)butanoate

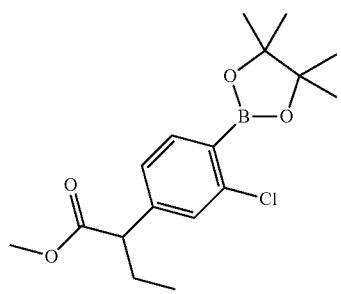

Lithium bis(trimethylsilyl)amide (3.86 mL, 3.86 mmol) was added to methyl 2-(3-chloro-4-(4,4,5,5-tetramethyl-1,3,2-dioxaborolan-2-yl)phenyl)acetate (Intermediate 2-7; 1 g, 3.22 mmol) in THF (10 mL) cooled to 0° C. under nitrogen. The resulting solution was stirred at 0° C. for 30 minutes. Iodoethane, stabilized with silver (0.258 mL, 3.22 mmol), was added and the reaction stirred for 30 minutes. Ammonium chloride (satd) (25 mL) added with vigorous stirring, ethyl acetate (50 mL) added and the organic phase separated, washed with water (25 mL) and saturated brine (25 mL). The organic layer was dried over MgSO$_4$, filtered and evaporated to afford crude product. The crude product was purified by flash silica chromatography, elution gradient 0 to 10% EtOAc in isohexane. Pure fractions were evaporated to dryness to afford methyl 2-(3-chloro-4-(4,4,5,5-tetramethyl-1,3,2-dioxaborolan-2-yl)phenyl)butanoate (0.686 g, 62.9%) as a colourless oil.

$^1$H NMR (400.13 MHz, CDCl$_3$) δ 0.80 (2H, t), 1.29 (12H, s), 1.86-2.06 (2H, m), 3.34 (1H, t), 3.57 (3H, s), 7.04 (1H, d), 7.19 (2H, d), 7.58 (1H, d).

m/z (EI+) (M+H)+=338

Example 12

2-(4'-(6-Carbamoyl-3,5-dimethylpyrazin-2-yl)-2-methylbiphenyl-4-yl)acetic acid

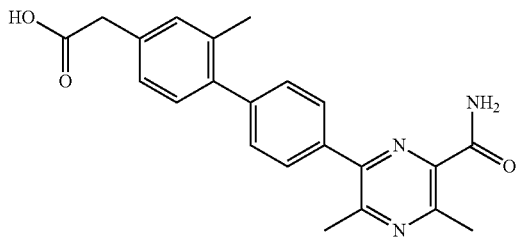

Powdered potassium hydroxide (65.9 mg, 1.17 mmol) was added in one portion to ethyl 2-(4'-(6-carbamoyl-3,5-dimethylpyrazin-2-yl)-2-methylbiphenyl-4-yl)acetate (Intermediate 12-1; 79 mg, 0.20 mmol) in tert-butanol (2 mL) at 45° C. under nitrogen. The resulting solution was stirred at 45° C. for 1 hour. The mixture was treated with acetic acid (0.090 mL, 1.57 mmol) in ethanol (1 mL) and stirred at room temperature for 10 minutes. The mixture was then evaporated under vacuum to give an off white solid. This was triturated with water (10 mL), filtered off and washed with water (10 mL), before drying under vacuum to give desired product.

$^1$H NMR (400.13 MHz, DMSO-d6) δ 2.28 (3H, s), 2.65 (3H, s), 2.76 (3H, s), 3.58 (2H, s), 7.19 (3H, dd), 7.47 (2H, dd), 7.61 (1H, s), 7.82 (2H, dt), 8.03 (1H, s), 12.30 (1H, s). m/z (ES+) (M+H)+=376.37

Intermediate 12-1: Ethyl 2-(4'-(6-carbamoyl-3,5-dimethylpyrazin-2-yl)-2-methylbiphenyl-4-yl)acetate

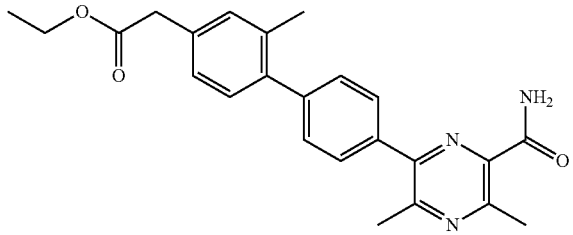

A solution of 4-(6-carbamoyl-3,5-dimethylpyrazin-2-yl)phenylboronic acid (138 mg, 0.51 mmol), methyl 2-(3-methyl-4-(trifluoromethylsulfonyloxy)phenyl)acetate (Intermediate 12-2; 159 mg, 0.51 mmol) and tripotassium phosphate (162 mg, 0.76 mmol) in DME (3 mL), ethanol (1.5 mL) and water (0.5 mL) was degassed before addition of (1,1'-bis(diphenylphosphino)ferrocene)-dichloropalladium(II) (DCM adduct) (33.5 mg, 0.04 mmol). The reaction mixture was heated to 80° C., under nitrogen, and left to stir overnight for 16 hrs. The reaction mixture was allowed to cool to room temperature and then evaporated. The residue was partitioned between water (20 mL) and EtOAc (50 mL). The aqueous was re-extracted with EtOAc (2×10 mL) and the combined organics washed with brine (20 mL), dried (MgSO$_4$) and evaporated to give crude product. The crude product was purified by flash silica chromatography, elution gradient 10 to 100% EtOAc in isohexane on 12 g silicycle column. Pure fractions were evaporated to dryness to afford ethyl 2-(4'-(6-carbamoyl-3,5-dimethylpyrazin-2-yl)-2-methylbiphenyl-4-yl)acetate (79 mg, 38.4%) as a colourless oil which crystallised on standing.

$^1$H NMR (400.132 MHz, DMSO) δ 1.17 (3H, t), 2.28 (3H, s), 2.65 (3H, s), 2.76 (3H, s), 3.67 (2H, s), 4.08-4.13 (2H, m), 7.17-7.24 (3H, m), 7.47 (2H, d), 7.61 (1H, s), 7.82 (2H, d), 8.02 (1H, s). m/z (ES+) (M+H)+=404

Intermediate 12-2: Methyl 2-(3-methyl-4-(trifluoromethylsulfonyloxy)phenyl)acetate

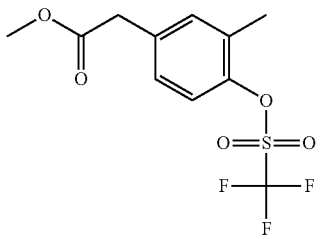

Trifluoromethane sulfonic anhydride (0.217 mL, 1.32 mmol) was added dropwise to methyl 2-(4-hydroxy-3-methylphenyl)acetate (159 mg, 0.88 mmol), in DCM (4 mL) at 0° C. under nitrogen. The resulting solution was then treated with triethylamine (0.369 mL, 2.65 mmol) and allowed to warm to and stir at 18° C. for 16 hours. The mixture was diluted with DCM (20 mL) and water (20 mL) and the organics separated. The organics were washed with saturated NaHCO$_3$ (aq, 50 mL), brine (10 mL) dried (MgSO$_4$) and evaporated to crude material. The crude product was purified by flash silica chromatography, elution gradient 0 to 30% EtOAc in isohexane. Pure fractions were evaporated to dryness to afford methyl 2-(3-methyl-4-(trifluoromethylsulfonyloxy)phenyl)acetate (169 mg, 61.3%) as a colourless oil.

$^1$H NMR (400.132 MHz, DMSO) δ 2.30 (3H, s), 3.62 (3H, s), 3.72 (2H, s), 7.26-7.29 (1H, m), 7.33 (1H, d), 7.35-7.36 (1H, m). m/z (ES−) (M−H)−=311

Example 13

2-(4'-(6-Carbamoyl-3,5-dimethylpyrazin-2-yl)-2-chlorobiphenyl-4-yl)-2-methylpropanoic acid

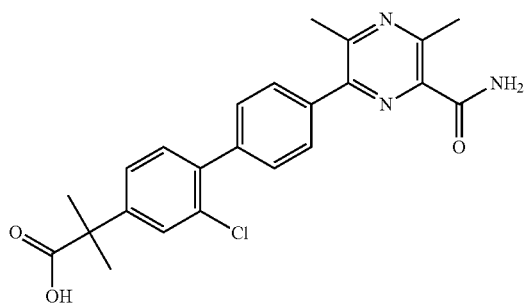

Lithium bis(trimethylsilyl)amide (9.66 mL, 9.66 mmol) was added to methyl 2-(3-chloro-4-(4,4,5,5-tetramethyl-1,3,2-dioxaborolan-2-yl)phenyl)acetate (Intermediate 2-7; 2.5 g, 8.05 mmol) in THF (25 mL) cooled to 0° C. under nitrogen. The resulting solution was stirred at 0° C. for 30 minutes. Methyl iodide (0.752 mL, 12.07 mmol) was added and the reaction stirred for 30 minutes Ammonium chloride (satd) (25 mL) added with vigorous stirring, ethyl acetate (50 mL) added and the organic phase separated, washed with water (25 mL) and saturated brine (25 mL). The organic layer was dried over MgSO$_4$, filtered and evaporated to afford crude product (5.67 g). The crude product was purified by flash silica chromatography, elution gradient 0 to 10% EtOAc in isohexane. Pure fractions were evaporated to dryness to afford a colourless oil. To this was added a solution of 4-(6-carbamoyl-3,5-dimethylpyrazin-2-yl)phenyl trifluoromethanesulfonate (Intermediate 7-4; 809 mg, 2.16 mmol) and potassium phosphate, tri-basic (549 mg, 2.59 mmol) in DME (10 mL), methanol (5.00 mL) and water (2.500 mL) was thoughroughly degassed. The mixture was treated with PdCl$_2$(dppf)-DCM adduct (88 mg, 0.11 mmol), degassed again and the atmosphere replaced with nitrogen before being heated to 90° C. for 4 hours. The reaction mixture was allowed to cool, diluted with EtOAc (40 mL) and water (20 mL). This was passed through a silica pad washing with EtOAc. The filtrate was separated and washed with brine (20 mL) then evaporated to afford crude product. The crude product was purified by flash silica chromatography, elution gradient 0 to 70% EtOAc in isohexane. Pure fractions were evaporated to dryness to afford a cream solid, powdered potassium hydroxide (476 mg, 8.49 mmol) was added in one portion to this in tert-butanol (25 mL) at 45° C. under nitrogen. The resulting solution was stirred at 100° C. for 16 hours. The mixture was treated with acetic acid (0.648 mL, 11.32 mmol) in ethanol (20 mL) and stirred at room temperature for 10 minutes. The mixture was then evaporated under vacuum to give an off white solid. This was triturated with water (20 mL), filtered off and washed with water (10 mL), before drying under vacuum to give crude solid. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 2-(4'-(6-carbamoyl-3,5-dimethylpyrazin-2-yl)-2-chlorobiphenyl-4-yl)-2-methylpropanoic acid (53.0 mg, 8.83%) as a white foam.

$^1$H NMR (400.13 MHz, DMSO-d6) δ 1.53 (6H, s), 2.65 (3H, s), 2.76 (3H, s), 7.43 (2H, dd), 7.50 (1H, d), 7.58 (2H, dt), 7.61 (1H, s), 7.85 (2H, dt), 8.04 (1H, s), 12.57 (1H, s). m/z (ES+) (M+H)+=424.37

Example 14

2-(2-(4'-(6-Carbamoyl-3,5-dimethylpyrazin-2-yl)-2-chlorobiphenyl-4-yl)acetamido)-2-methylpropanoic acid

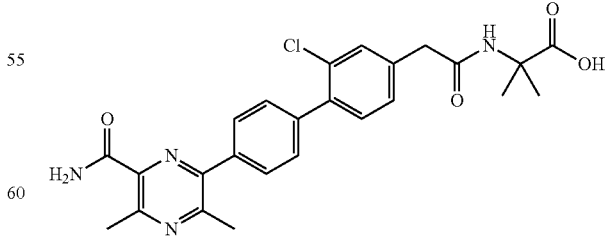

Potassium hydroxide (109 mg, 1.94 mmol) was added in one portion to methyl 2-(2-(4'-(6-carbamoyl-3,5-dimethylpyrazin-2-yl)-2-chlorobiphenyl-4-yl)acetamido)-2-methylpropanoate (Intermediate 14-1; 319.5 mg, 0.65 mmol) in t-BuOH (4164 µL) at room temperature. The resulting solution was stirred at 45° C. for 5 hours and a precipitate formed. The reaction mixture was quenched with 2M HCl (5 mL), The reaction mixture was evaporated to dryness and redissolved in water (10 mL), and filtered through nylon, washed with water and dried under vacuum. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were evaporated to dryness to afford 2-(2-(4'-(6-carbamoyl-3,5-dimethylpyrazin-2-yl)-2-chlorobiphenyl-4-yl)acetamido)-2-methylpropanoic acid (18.20 mg, 5.86%) as a white solid.

$^1$H NMR (400.132 MHz, MeOD) δ 1.50 (6H, s), 2.69 (3H, s), 2.87 (3H, s), 3.57 (2H, s), 7.37 (2H, d), 7.49 (1H, s), 7.57 (2H, d), 7.75 (2H, d). m/z (ES+), (M+H)+=481

Intermediate 14-1: Methyl 2-(2-(4'-(6-carbamoyl-3,5-dimethylpyrazin-2-yl)-2-chlorobiphenyl-4-yl)acetamido)-2-methylpropanoate

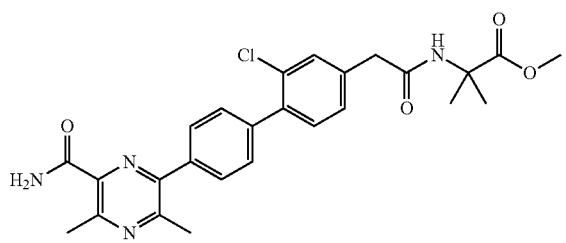

A mixture of methyl 2-amino-2-methylpropanoate hydrochloride (88 mg, 0.57 mmol) and N-ethyl-N-isopropylpropan-2-amine (99 µL, 0.57 mmol) in DMF (342 µL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 µL, 0.57 mmol) in DMF (2049 µL) at RT. The resulting solution was stirred at RT for 20 hours. The reaction mixture was evaporated to dryness and redissolved in DCM (5 mL), and washed with water (5 mL). The organic layer was evaporated to afford methyl 2-(2-(4'-(6-carbamoyl-3,5-dimethylpyrazin-2-yl)-2-chlorobiphenyl-4-yl)acetamido)-2-methylpropanoate (320 mg, 125%) which was used without further purification.

$^1$H NMR (400.13 MHz, CDCl$_3$) δ 1.25-1.27 (3H, m), 1.51 (4H, s), 2.59 (1H, s), 2.66 (3H, s), 2.81 (14H, s), 2.89-2.93 (16H, m), 2.92 (1H, s), 3.50 (1H, s), 3.69 (2H, s), 5.23 (21H, s), 7.19 (4H, s), 7.30 (1H, s), 7.51 (2H, d), 7.59 (2H, d), 7.95 (5H, s)

m/z (ES+), (M+H)+=495

Example 15

(S)-2-(2-(4'-(6-Carbamoyl-3,5-dimethylpyrazin-2-yl)-2-chlorobiphenyl-4-yl)acetamido)-4-methylpentanoic acid

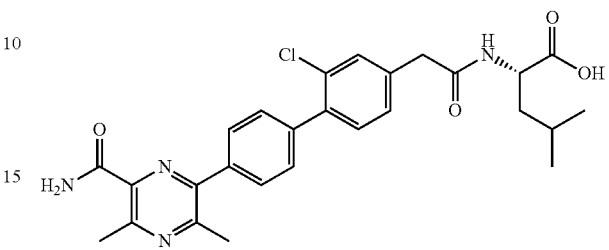

Potassium hydroxide (70.3 mg, 1.25 mmol) was added in one portion to (S)-ethyl 2-(2-(4'-(6-carbamoyl-3,5-dimethylpyrazin-2-yl)-2-chlorobiphenyl-4-yl)acetamido)-4-methylpentanoate (Intermediate 15-1; 224.4 mg, 0.42 mmol) in t-BuOH (2696 µL) at RT. The resulting solution was stirred at 45° C. for 5 hours a precipitate formed. The reaction mixture was quenched with 2M HCl (5 mL), The reaction mixture was evaporated to dryness and redissolved in water (10 mL), and filtered through nylon, washed with water and dried under vacuum. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were evaporated to dryness to afford (S)-2-(2-(4'-(6-carbamoyl-3,5-dimethylpyrazin-2-yl)-2-chlorobiphenyl-4-yl)acetamido)-4-methylpentanoic acid (20.40 mg, 9.59%) as a white solid.

$^1$H NMR (400.132 MHz, MeOD) d0.92 (3H, d), 0.97 (3H, d), 1.44 (1H, s), 1.60-1.77 (3H, m), 2.69 (3H, s), 2.87 (3H, s), 3.63 (2H, s), 4.43-4.50 (1H, m), 7.33-7.40 (2H, m), 7.52 (2H, s), 7.56 (1H, s), 7.57 (2H, d), 7.76 (2H, d). m/z (ES+), (M+H)+=509

Intermediate 15-1: (S)-Ethyl 2-(2-(4'-(6-carbamoyl-3,5-dimethylpyrazin-2-yl)-2-chlorobiphenyl-4-yl)acetamido)-4-methylpentanoate

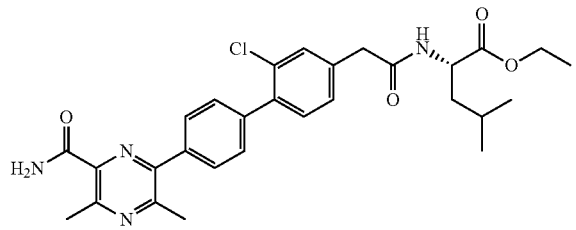

A mixture of (S)-ethyl 2-amino-4-methylpentanoate hydrochloride (111 mg, 0.57 mmol) and N-ethyl-N-isopropylpropan-2-amine (99 µL, 0.57 mmol) in DMF (342 µL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 µL, 0.57 mmol) in DMF (2049 µL) at RT. The resulting solution was stirred at RT for 20 hours. The reaction was incomplete so the temperature was increased to 50° C. and the reaction mixture was stirred for a further 3 hours. The reaction mixture was diluted with EtOAc (20 mL), and washed sequentially with water (50 mL), saturated brine (50 mL), and water (100 mL). The organic layer was dried over $MgSO_4$, filtered and evaporated to afford (S)-ethyl 2-(2-(4'-(6-carbamoyl-3,5-dimethylpyrazin-2-yl)-2-chlorobiphenyl-4-yl)acetamido)-4-methylpentanoate (224 mg, 81%) which was used without further purification.

m/z (ES+), (M+H)+=537

Example 16

3-(2-(4'-(6-Carbamoyl-3,5-dimethylpyrazin-2-yl)-2-chlorobiphenyl-4-yl)acetamido)propanoic acid

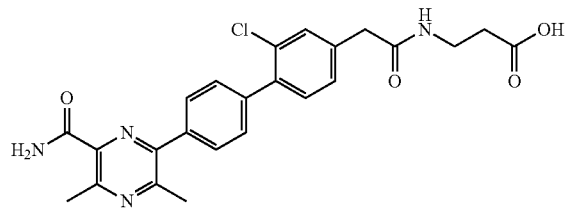

Potassium hydroxide (131 mg, 2.34 mmol) was added in one portion to ethyl 3-(2-(4'-(6-carbamoyl-3,5-dimethylpyrazin-2-yl)-2-chlorobiphenyl-4-yl)acetamido)propanoate (Intermediate 16-1; 386.5 mg, 0.78 mmol) in t-BuOH (5038 µL) at RT. The resulting solution was stirred at 45° C. for 5 hours a precipitate formed. The reaction mixture was quenched with 2M HCl (5 mL), The reaction mixture was evaporated to dryness and redissolved in water (10 mL), and filtered through nylon, washed with water and dried under vacuum. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were evaporated to dryness to afford 3-(2-(4'-(6-carbamoyl-3,5-dimethylpyrazin-2-yl)-2-chlorobiphenyl-4-yl)acetamido)propanoic acid (56.4 mg, 15.47%) as a white solid.

$^1$H NMR (400.132 MHz, DMSO) δ 2.47 (2H, t), 2.71 (3H, s), 2.83 (3H, s), 3.35 (2H, s), 3.55 (2H, s), 7.38 (1H, d), 7.48 (1H, d), 7.54 (1H, d), 7.63 (2H, d), 7.68 (1H, s), 7.91 (2H, d), 8.11 (1H, s), 8.26 (1H, t), 1.2.27 (1H, s). m/z (ES+), (M+H)+=467

Intermediate 16-1: Ethyl 3-(2-(4'-(6-carbamoyl-3,5-dimethylpyrazin-2-yl)-2-chlorobiphenyl-4-yl)acetamido)propanoate

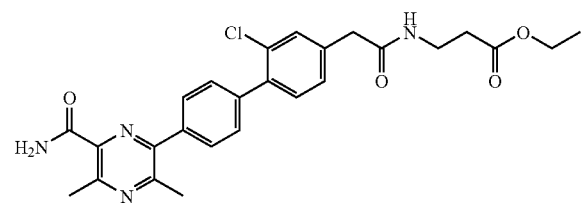

A mixture of ethyl 3-aminopropanoate hydrochloride (88 mg, 0.57 mmol) and N-ethyl-N-isopropylpropan-2-amine (99 µL, 0.57 mmol) in DMF (342 µL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-Dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 µL, 0.57 mmol) in DMF (2049 µL) at RT. The resulting solution was stirred at RT for 20 hours. The reaction mixture was evaporated to dryness and redissolved in DCM (5 mL), and washed with water (5 mL). The organic layer was evaporated to afford ethyl 3-(2-(4'-(6-carbamoyl-3,5-dimethylpyrazin-2-yl)-2-chlorobiphenyl-4-yl)acetamido)propanoate (387 mg, 151%) which was used without further purification.

$^1$H NMR (400.13 MHz, CDCl$_3$) δ 1.18 (3H, t), 1.28 (3H, d), 2.48 (2H, t), 2.66 (3H, s), 2.81 (7H, s), 2.89-2.93 (10H, m), 3.48 (3H, t), 4.07 (2H, t), 5.23 (5H, s), 7.19 (4H, s), 7.20 (1H, s), 7.29-7.31 (1H, m), 7.35 (1H, d), 7.49-7.51 (2H, m), 7.58-7.61 (2H, m), 7.95 (2H, s). m/z (ES+), (M+H)+=495

Example 17

(S)-2-(2-(4'-(6-Carbamoyl-3,5-dimethylpyrazin-2-yl)-2-chlorobiphenyl-4-yl)acetamido)-3-methylbutanoic acid

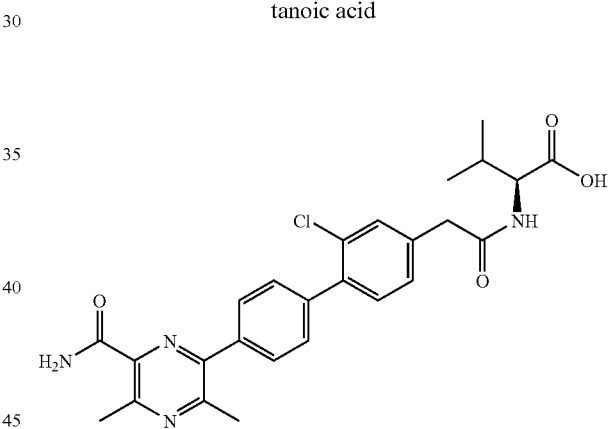

Potassium hydroxide (108 mg, 1.93 mmol) was added in one portion to (S)-methyl 2-(2-(4'-(6-carbamoyl-3,5-dimethylpyrazin-2-yl)-2-chlorobiphenyl-4-yl)acetamido)-3-methylbutanoate (Intermediate 17-1; 327.4 mg, 0.64 mmol) in t-BuOH (4150 µL) at RT. The resulting solution was stirred at 45° C. for 5 hours a precipitate formed. The reaction mixture was quenched with 2M HCl (5 mL), The reaction mixture was evaporated to dryness and redissolved in water (10 mL), and filtered through nylon, washed with water and dried under vacuum. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were evaporated to dryness to afford (S)-2-(2-(4'-(6-carbamoyl-3,5-dimethylpyrazin-2-yl)-2-chlorobiphenyl-4-yl)acetamido)-3-methylbutanoic acid (93 mg, 29.1%) as a white solid.

$^1$H NMR (400.132 MHz, MeOD) δ 0.98 (3H, d), 0.99 (3H, d), 2.15-2.26 (1H, m), 2.69 (3H, s), 2.88 (3H, s), 3.67 (2H, s), 4.33-4.39 (1H, m), 7.52 (1H, s), 7.57 (2H, d), 7.63 (1H, d), 7.76 (2H, d), 7.80 (1H, d). m/z (ES+), (M+H)+=495

Intermediate 17-1: (S)-Methyl 2-(2-(4'-(6-carbamoyl-3,5-dimethylpyrazin-2-yl)-2-chlorobiphenyl-4-yl)acetamido)-3-methylbutanoate

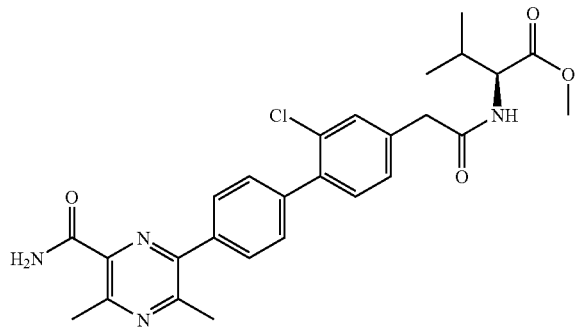

A mixture of (S)-methyl 2-amino-3-methylbutanoate hydrochloride (95 mg, 0.57 mmol) and N-ethyl-N-isopropylpropan-2-amine (99 µL, 0.57 mmol) in DMF (342 µL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-Dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 µL, 0.57 mmol) in DMF (2049 µL) at RT. The resulting solution was stirred at RT for 20 hours. The reaction mixture was evaporated to dryness and redissolved in DCM (5 mL), and washed with water (5 mL). The organic layer was evaporated to afford (S)-methyl 2-(2-(4'-(6-carbamoyl-3,5-dimethylpyrazin-2-yl)-2-chlorobiphenyl-4-yl)acetamido)-3-methylbutanoate (327 mg, 124%) which was used without further purification.

$^1$H NMR (400.13 MHz, CDCl$_3$) δ −0.07 (2H, s), 0.81 (3H, d), 0.86-0.87 (3H, m), 1.26 (2H, d), 2.59 (1H, s), 2.66 (3H, s), 2.81 (9H, s), 2.88-2.93 (12H, m), 3.57 (2H, s), 3.68 (3H, s), 4.51-4.54 (1H, m), 5.23 (10H, s), 7.19-7.24 (4H, m), 7.32 (2H, d), 7.39 (1H, d), 7.50-7.52 (2H, m), 7.58-7.60 (2H, m), 7.95 (3H, s).

m/z (ES+), (M+H)+=509

Example 18

2-(2-(4'-(6-Carbamoyl-3,5-dimethylpyrazin-2-yl)-2-chlorobiphenyl-4-yl)-N-methylacetamido)-2-methylpropanoic acid

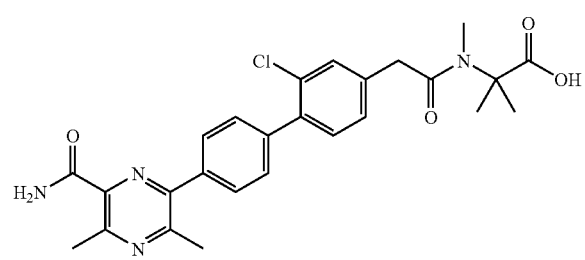

A solution of benzyl 2-(2-(4'-(6-carbamoyl-3,5-dimethylpyrazin-2-yl)-2-1; chlorobiphenyl-4-yl)-N-methylacetamido)-2-methylpropanoate (Intermediate 18-1 2.46 g, 0.78 mmol) in EtOAc (13.3 mL) and MeOH (2.2 mL) were hydrogenated in the H-Cube hydrogenation cell using a 55 mm 10% palladium on carbon cartridge, at RT and 50 bar at a flow rate of 1 mL/minute. The resulting solution was evaporated to give crude product. The crude product was purified by preparative HPLC (Waters XBridge Prep C18 OBD column, 5µ silica, 50 mm diameter, 150 mm length), using decreasingly polar mixtures of water (containing 0.1% formic acid) and 3:1 MeOH/MeCN as eluents. Fractions containing the desired compound were evaporated to dryness to afford 2-(2-(4'-(6-carbamoyl-3,5-dimethylpyrazin-2-yl)-2-chlorobiphenyl-4-yl)-N-methylacetamido)-2-methylpropanoic acid (21.60 mg, 5.61%) as a white solid.

$^1$H NMR (400.132 MHz, CDCl$_3$) d1.18 (1H, s), 1.46 (3H, s), 2.64 (3H, s), 2.92 (3H, s), 2.99 (3H, s), 3.42 (3H, s), 3.71 (2H, s), 6.37 (1H, s), 7.16 (1H, d), 7.25 (1H, d), 7.34 (1H, s), 7.46 (2H, d), 7.55 (2H, d), 7.77 (1H, s). m/z (ES+), (M+H)+=495

Intermediate 18-1: Benzyl 2-(2-(4'-(6-carbamoyl-3,5-dimethylpyrazin-2-yl)-2-chlorobiphenyl-4-yl)-N-methylacetamido)-2-methylpropanoate

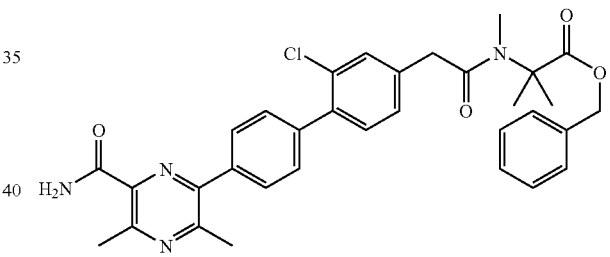

A mixture of benzyl 2-methyl-2-(methylamino)propanoate (118 mg, 0.57 mmol) and N-ethyl-N-isopropylpropan-2-amine (99 µL, 0.57 mmol) in DMF (342 µL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-Dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 µL, 0.57 mmol) in DMF (2049 µL) at RT. The resulting solution was stirred at RT for 20 hours. The reaction mixture was evaporated to dryness and redissolved in DCM (5 mL), and washed with water (5 mL). The organic layer was evaporated to afford crude product which was used without further purification.

$^1$H NMR (400.13 MHz, CDCl$_3$) δ 1.41 (6H, s), 2.59 (1H, s), 2.66 (3H, s), 2.81 (11H, s), 2.88 (11H, s), 2.93 (3H, d), 2.94 (3H, s), 3.67 (2H, s), 4.63 (3H, s), 5.08 (2H, s), 7.20 (5H, d), 7.23 (1H, s), 7.24 (1H, s), 7.25-7.26 (2H, m), 7.29 (1H, s), 7.28-7.30 (8H, m), 7.49 (2H, d), 7.59 (2H, d), 7.94 (4H, s). m/z (ES+), (M+H)+=585

Example 19

1-(2-(4'-(6-Carbamoyl-3,5-dimethylpyrazin-2-yl)-2-chlorobiphenyl-4-yl)acetyl)piperidine-4-carboxylic acid

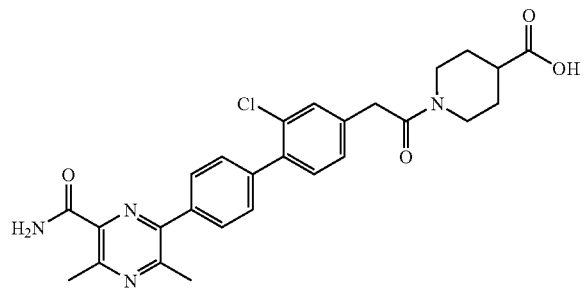

Potassium hydroxide (91 mg, 1.63 mmol) was added in one portion to ethyl 1-(2-(4'-(6-carbamoyl-3,5-dimethylpyrazin-2-yl)-2-chlorobiphenyl-4-yl)acetyl)piperidine-4-carboxylate (Intermediate 19-1; 290.7 mg, 0.54 mmol) in t-BuOH (3505 μL) at RT. The resulting solution was stirred at 45° C. for 5 hours a precipitate formed. The reaction mixture was quenched with 2M HCl (5 mL), The reaction mixture was evaporated to dryness and redissolved in water (10 mL), and filtered through nylon, washed with water and dried under vacuum. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 1-(2-(4'-(6-carbamoyl-3,5-dimethylpyrazin-2-yl)-2-chlorobiphenyl-4-yl)acetyl)piperidine-4-carboxylic acid (59.8 mg, 21.71%) as a white solid.

$^1$H NMR (400.132 MHz, CDCl$_3$) d1.55-1.68 (1H, m), 1.82-1.98 (2H, m), 2.50-2.59 (1H, m), 2.66 (3H, s), 2.89 (1H, s), 2.92 (3H, s), 3.14 (1H, t), 3.42 (2H, s), 3.70 (2H, s), 3.82 (1H, d), 4.38 (1H, d), 5.90 (1H, s), 7.17 (1H, s), 7.29 (1H, d), 7.34 (1H, s), 7.51 (2H, d), 7.59 (2H, d), 7.78 (1H, s). m/z (ES+), M+=507

Intermediate 19-1: Ethyl 1-(2-(4'-(6-carbamoyl-3,5-dimethylpyrazin-2-yl)-2-chlorobiphenyl-4-yl)acetyl)piperidine-4-carboxylate

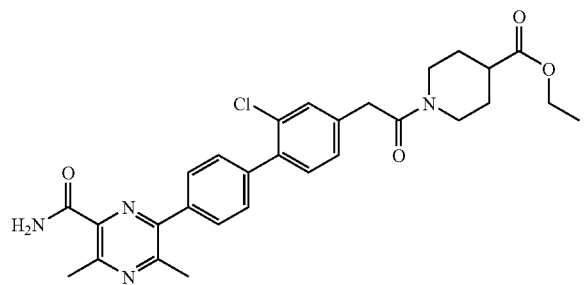

A mixture of ethyl piperidine-4-carboxylate (90 mg, 0.57 mmol) and N-ethyl-N-isopropylpropan-2-amine (99 μL, 0.57 mmol) in DMF (342 μL) were treated with a solution of 2-(4'-(6-carbamoyl-3,5-dimethylpyrazin-2-yl)-2-chlorobiphenyl-4-yl)acetic acid (Example 1; 205 mg, 0.52 mmol), 1-(3-Dimethylaminopropyl)-3-ethylcarbodiimide hydrochloride (124 mg, 0.65 mmol), 1H-benzo[d][1,2,3]triazol-1-ol (70.0 mg, 0.52 mmol) and N-ethyl-N-isopropylpropan-2-amine (99 μL, 0.57 mmol) in DMF (2049 μL) at RT. The resulting solution was stirred at RT for 20 hours. The reaction mixture was evaporated to dryness and redissolved in DCM (5 mL), and washed with water (5 mL). The organic layer was evaporated to afford ethyl 1-(2-(4'-(6-carbamoyl-3,5-dimethylpyrazin-2-yl)-2-chlorobiphenyl-4-yl)acetyl)piperidine-4-carboxylate (291 mg, 105%) which was used without further purification.

$^1$H NMR (400.13 MHz, CDCl$_3$) δ 1.19 (3H, t), 2.59 (1H, s), 2.66 (3H, s), 2.81-2.81 (5H, m), 2.88-2.93 (8H, m), 3.68 (2H, s), 4.08 (2H, t), 5.23 (4H, s), 7.18 (1H, s), 7.19 (3H, s), 7.28 (1H, s), 7.33 (1H, d), 7.50-7.52 (2H, m), 7.58-7.60 (2H, m), 7.95 (2H, s). m/z (ES+), (M+H)+=535

Example 20

2-(2-(4'-(6-Carbamoyl-3,5-dimethylpyrazin-2-yl)-2-chlorobiphenyl-4-yl)acetamido)acetic acid

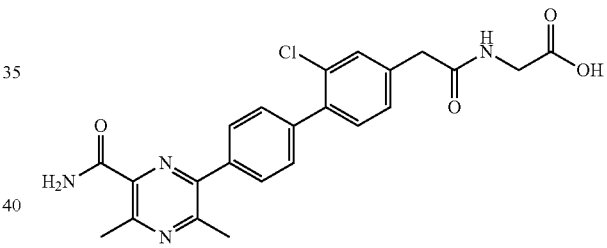

Powdered potassium hydroxide (106 mg, 1.89 mmol) was added in one portion to methyl 2-(2-(4'-(6-carbamoyl-3,5-dimethylpyrazin-2-yl)-2-chlorobiphenyl-4-yl)acetamido)acetate (Intermediate 20-1; 294 mg, 0.63 mmol) in tert-butanol (4062 μL) at 45° C. The resulting solution was stirred at 45° C. for 150 minutes, a thick white suspension slowly precipitate formed. 2M HCl (5 mL) was added and the mixture was evaporated to remove the organic solvent. The reaction mixture was diluted with EtOAc and water, the organic layer was collected, dried with MgSO$_4$ and evaporated to afford crude product. This was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford 2-(2-(4'-(6-carbamoyl-3,5-dimethylpyrazin-2-yl)-2-chlorobiphenyl-4-yl)acetamido)acetic acid (56.8 mg, 19.92%) as a white solid.

$^1$H NMR (400.132 MHz, DMSO) δ 2.72 (3H, s), 2.83 (3H, s), 3.64 (2H, s), 3.85 (2H, d), 7.13 (1H, s), 7.41 (1H, d), 7.49 (1H, d), 7.63 (2H, d), 7.68 (1H, s), 7.91 (2H, d), 8.10 (1H, s), 8.52 (1H, t). m/z (ES-), M-=451

Intermediate 20-1: methyl 2-(2-(4'-(6-Carbamoyl-3,5-dimethylpyrazin-2-yl)-2-chlorobiphenyl-4-yl)acetamido)acetate

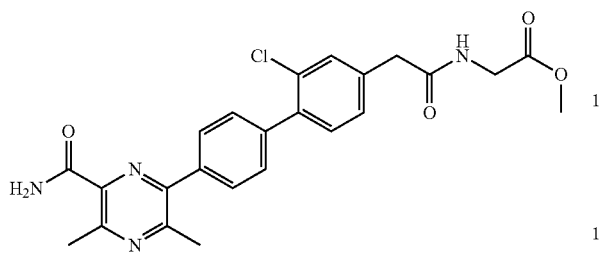

A solution of 2-(4'-(6-carbamoyl-3,5-dimethylpyrazin-2-yl)-2-chlorobiphenyl-4-yl)acetic acid (Example 1; 250 mg, 0.63 mmol), 1-(3-dimethylaminopropyl)-3-ethylcarbodiimide hydrochloride (151 mg, 0.79 mmol), 1H-benzo[d][1,2,3]triazol-1-ol (85 mg, 0.63 mmol) and N-ethyl-N-isopropylpropan-2-amine (242 μL, 1.39 mmol) in DMF (2499 μL) was treated with a solution of methyl 2-aminoacetate hydrochloride (87 mg, 0.69 mmol) in DMF (417 μL) at 23° C. The resulting solution was stirred at RT for 4 hours. The reaction mixture was evaporated to dryness and redissolved in EtOAc (25 mL), and washed sequentially with saturated brine (50 mL) and water (50 mL). The organic layer was dried over MgSO$_4$, filtered and evaporated to afford methyl 2-(2-(4'-(6-carbamoyl-3,5-dimethylpyrazin-2-yl)-2-chlorobiphenyl-4-yl)acetamido)acetate (266 mg, 90%) which was used without further purification.

$^1$H NMR (400.13 MHz, DMSO-d6) δ 1.18 (2H, t), 2.00 (2H, s), 2.60 (1H, s), 2.67 (4H, d), 2.67-2.67 (1H, m), 2.76 (5H, t), 3.59 (2H, s), 3.65 (3H, s), 3.89-3.90 (2H, m), 4.04 (1H, d), 7.36 (1H, d), 7.43-7.45 (1H, m), 7.53 (1H, s), 7.57-7.59 (2H, m), 7.72 (1H, d), 7.85-7.87 (2H, m), 7.99 (1H, d). m/z (ES+), (M+H)+=467

Example 21

2-(4'-(6-Carbamoyl-3,5-dimethylpyrazin-2-yl)-2,6-difluorobiphenyl-4-yl)propanoic acid

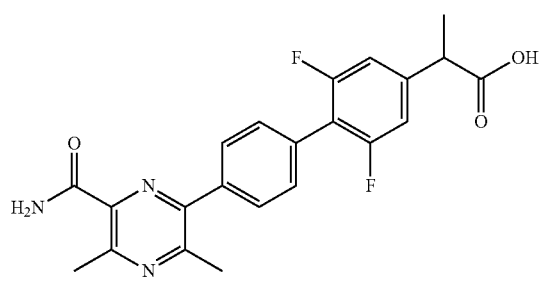

Potassium hydroxide (0.396 g, 7.05 mmol) was added in one portion to methyl 2-(4'-(6-carbamoyl-3,5-dimethylpyrazin-2-yl)-2,6-difluorobiphenyl-4-yl)propanoate (Intermediate 21-1; 1 g, 2.35 mmol) in t-BuOH (15.16 mL) at room temperature. The resulting solution was stirred at 45° C. for 5 hours, a precipitate formed. The reaction mixture was quenched with 2M HCl (5 mL), evaporated to dryness and redissolved in water (10 mL), filtered through nylon, washed with water and dried under vacuum to afford product as a white solid. The product was purified by preparative HPLC (Waters XBridge Prep C18 OBD column, 5μ silica, 50 mm diameter, 150 mm length), using decreasingly polar mixtures of water (containing 0.1% formic acid) and MeCN/MeOH as eluents. Fractions containing the desired compound were evaporated to dryness to afford 2-(4'-(6-carbamoyl-3,5-dimethylpyrazin-2-yl)-2,6-difluorobiphenyl-4-yl)propanoic acid (0.530 g, 54.8%) as a white powder.

$^1$H NMR (400.132 MHz, DMSO) δ 1.50 (3H, d), 2.71 (3H, s), 2.83 (3H, s), 3.86-3.94 (1H, m), 7.27 (2H, d), 7.66 (2H, d), 7.68 (1H, s), 7.95 (2H, d), 8.12 (1H, s), 12.65 (1H, s). m/z (ES+), (M+H)+=412

Intermediate 21-1: methyl 2-(4'-(6-Carbamoyl-3,5-dimethylpyrazin-2-yl)-2,6-difluorobiphenyl-4-yl)propanoate

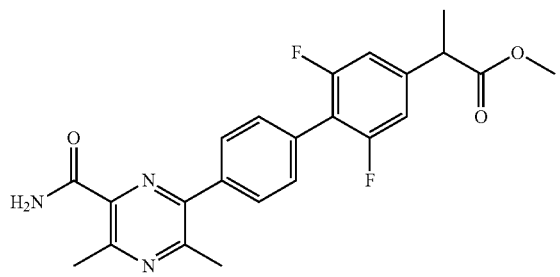

A solution of 4-(6-carbamoyl-3,5-dimethylpyrazin-2-yl)phenylboronic acid (175 mg, 0.65 mmol) and methyl 2-(3,5-difluoro-4-(trifluoromethylsulfonyloxy)phenyl)propanoate (Intermediate 21-2; 200 mg, 0.57 mmol) and Sodium carbonate (0.467 mL, 0.93 mmol), tetrakis(triphenylphosphine)palladium(0) (41.1 mg, 0.04 mmol) and lithium chloride (42.6 mg, 1.01 mmol) in DME (14.300 mL) was degassed and then stirred at 85° C. for 17 hours. The reaction mixture was partitioned between EtOAc (10 mL) and saturated brine (15 mL). The organic layer was dried over MgSO$_4$, filtered and evaporated to afford crude product. The crude product was purified by flash silica chromatography, elution gradient 0 to 50% EtOAc in isohexane. Pure fractions were evaporated to dryness to afford methyl 2-(4'-(6-carbamoyl-3,5-dimethylpyrazin-2-yl)-2,6-difluorobiphenyl-4-yl)propanoate (164 mg, 67.1%) as a white solid.

$^1$H NMR (400.132 MHz, CDCl$_3$) d1.53-1.57 (3H, m), 2.72 (3H, s), 3.00 (3H, s), 3.73 (3H, s), 3.76 (1H, q), 5.46 (1H, s), 7.00 (2H, d), 7.59 (2H, d), 7.68 (2H, d), 7.80 (1H, s).
m/z (ES+), (M+H)+=426

Intermediate 21-2: Methyl 2-(3,5-difluoro-4-(trifluoromethylsulfonyloxy)phenyl)propanoate

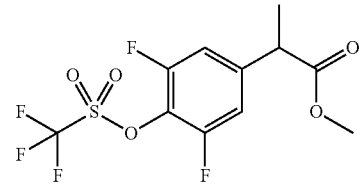

Triethylamine (4.82 mL, 34.55 mmol) was added dropwise to methyl 2-(3,5-difluoro-4-hydroxyphenyl)propanoate (Intermediate 21-3; 2.49 g, 11.52 mmol) and trifluoromethanesulfonic anhydride (2.91 mL, 17.28 mmol) in DCM (49.9 mL) at 0° C. under nitrogen. The resulting solution was stirred at 0° C. for 2 hours. The reaction mixture was diluted with water (50 mL), and washed sequentially with saturated NaHCO$_3$ (100 mL) and saturated brine (100 mL). The organic layer was dried over MgSO$_4$, filtered and evaporated to afford crude product. The crude product was purified by flash silica chromatography, elution gradient 0 to 60% EtOAc in isohexane. Pure fractions were evaporated to dryness to afford methyl 2-(3,5-difluoro-4-(trifluoromethylsulfonyloxy)phenyl)propanoate (3.13 g, 78%) as an orange oil.

$^1$H NMR (400.132 MHz, CDCl$_3$) d1.44 (3H, d), 3.64 (3H, s), 3.64 (1H, q), 6.98 (2H, d)

Intermediate 21-3: Methyl 2-(3,5-difluoro-4-hydroxyphenyl)propanoate

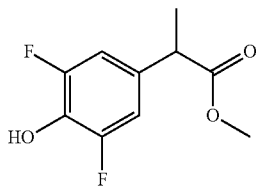

tribromoborane (7.37 mL, 77.99 mmol) was added dropwise to 2-(3,5-difluoro-4-methoxyphenyl)propanoic acid (Intermediate 21-4; 2.81 g, 13.00 mmol) in dichloromethane (96 mL) at 0° C. under nitrogen. The resulting solution was stirred at 0° C. for 1 hour. The reaction mixture was added dropwise to methanol (26.3 mL, 649.92 mmol) (—care reaction is vigorous and exothermic—MeOH kept in ice bath) and the mixture was stirred for a further 20 minutes. The reaction mixture was evaporated to dryness and redissolved in DCM (50 mL), and washed sequentially with saturated NaHCO$_3$ (50 mL) and water (50 mL). The organic layer was dried with MgSO$_4$ and evaporated to afford desired product methyl 2-(3, 5-difluoro-4-hydroxyphenyl)propanoate (2.490 g, 89%).

$^1$H NMR (400.132 MHz, CDCl$_3$) δ 1.46 (3H, d), 3.62 (1H, q), 3.68 (3H, s), 5.10 (1H, s), 6.87 (2H, d). m/z (ES−), (M−H)−=215

Intermediate 21-4: 2-(3,5-Difluoro-4-methoxyphenyl)propanoic acid

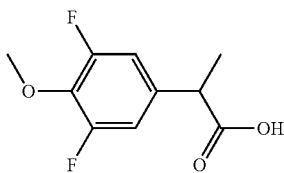

Lithium bis(trimethylsilyl)amide (25.4 mL, 25.35 mmol) was added to 2-(3,5-difluoro-4-methoxyphenyl)acetic acid (2.5 g, 12.37 mmol) in THF (60.8 mL) cooled to 0° C. under nitrogen. The resulting solution was stirred at 0° C. for 30 minutes. Next Methyl iodide (0.925 mL, 14.84 mmol) was added and the reaction stirred for 30 minutes Ammonium chloride (satd) (50 mL) added with vigorous stirring, ethyl acetate (100 mL) and water (50 mL) were added and the organic phase separated, washed with water (50 mL) and saturated brine (50 mL). The aq layer was acidified with 2M HCl (50 mL) and extracted with ethyl acetate. The organic layers were combined and dried over MgSO$_4$, filtered and evaporated to afford 2-(3,5-difluoro-4-methoxyphenyl)propanoic acid (2.81 g, 105%) which was used without further purification.

$^1$H NMR (400.132 MHz, CDCl$_3$) d1.33 (3H, d), 3.49 (1H, q), 3.82 (3H, s), 6.72 (2H, d). m/z (ES−), (M−H)−=215

Example 22

2-(4'-(6-Carbamoyl-3,5-dimethylpyrazin-2-yl)-2,2'-dichlorobiphenyl-4-yl)acetic acid

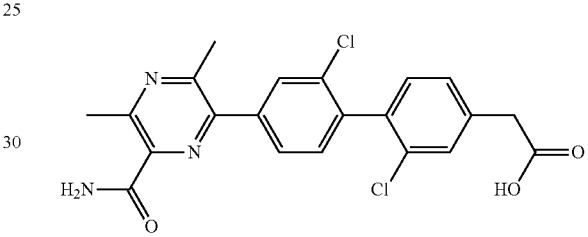

Powdered potassium hydroxide (0.045 g, 0.81 mmol) was added in one portion to methyl 2-(4'-(6-carbamoyl-3,5-dimethylpyrazin-2-yl)-2,2'-dichlorobiphenyl-4-yl)acetate (Intermediate 22-1; 0.12 g, 0.27 mmol) in tert-butanol (2.00 mL) at 40° C. under nitrogen. The resulting suspension was stirred at 40° C. for 20 minutes. A thick precipitate formed so the reaction was quenched with HCl (1.620 mL, 1.62 mmol) in ethanol (20.0 mL) and the resulting solution stirred for a further 20 minutes before being evaporated to dryness. The resulting solid was partitioned between water (5 mL) and EtOAc (15 mL). The aqueous layer showed a pH=4~5. The organic layer was separated and the aqueous re-extracted with EtOAc (2×5 mL). The combined organics were washed with brine (15 mL), dried over MgSO$_4$ and evaporated in vacuo to give product. This was washed with ether (5 mL) and dried under vacuum at room temperature to give an off white solid. The crude product was purified by preparative HPLC (Waters—Xbridge Prep C18 5 μm), using decreasingly polar mixtures of water (containing 0.1% ammonia) and {MeOH (3):MeCN(1)} as eluents. Fractions containing the desired compound were evaporated to dryness to afford 2-(4'-(6-carbamoyl-3,5-dimethylpyrazin-2-yl)-2,2'-dichlorobiphenyl-4-yl)acetic acid (0.063 g, 51.7%) as a colourless solid.

$^1$H NMR (400.13 MHz, DMSO-d6) δ 0.88-2.53 (1H, m), 2.65 (3H, s), 2.76 (3H, s), 3.55 (2H, s) assumed to be this—masked by a broad peak which is assumed to be due to water etc, 7.29-7.34 (2H, m), 7.45-7.49 (2H, m), 7.62-7.67 (1H, m), 7.78-7.81 (1H, m), 7.99 (1H, d), 8.12 (1H, s). m/z (ES+) (M+H)+=430.07

Intermediate 22-1: Methyl 2-(4'-(6-carbamoyl-3,5-dimethylpyrazin-2-yl)-2,2'-dichlorobiphenyl-4-yl)acetate

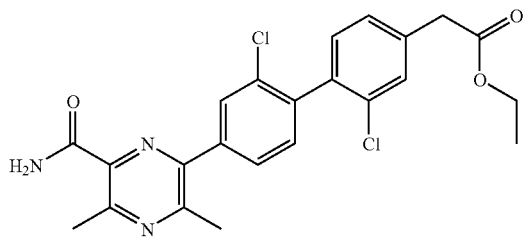

A solution of 4-(6-carbamoyl-3,5-dimethylpyrazin-2-yl)-2-chlorophenylboronic acid (Intermediate 5-1; 450 mg, 1.47 mmol), methyl 2-(3-chloro-4-(trifluoromethylsulfonyloxy)phenyl)acetate (Intermediate 1-2; 490 mg, 1.47 mmol) and tripotassium phosphate (469 mg, 2.21 mmol) in DME (6 mL), ethanol (3 mL) and water (1.5 mL) was put under vacuum and refilled with nitrogen before addition of (1,1'-bis(diphenylphosphino)ferrocene)-dichloropalladium(II) (DCM adduct) (97 mg, 0.12 mmol). The reaction mixture was heated to and left to stir overnight for 16 hrs. The reaction mixture was allowed to cool to room temperature and then evaporated. The residue was partitioned between water (20 mL) and EtOAc (50 mL). The aqueous was re-extracted with EtOAc (2×10 mL) and the combined organics washed with brine (20 mL), dried (MgSO₄) and evaporated to give crude product. The crude product was purified by flash silica chromatography, elution gradient 0 to 50% EtOAc in isohexane on 40 g silicycle column (eluted of at 50%). Pure fractions were evaporated to dryness to afford ethyl 2-(4'-(6-carbamoyl-3,5-dimethylpyrazin-2-yl)-2,2'-dichlorobiphenyl-4-yl)acetate (130 mg, 19.26%) as a white solid. Trans esterification occurred during the reaction giving the product as an ethyl rather than methyl ester.

¹H NMR (400.13 MHz, CDCl₃) δ 1.30 (3H, t), 2.73 (3H, s), 3.01 (3H, s), 3.67 (2H, m), 4.21 (2H, q), 5.58 (1H, s), 7.29 (2H, s), 7.40 (1H, d), 7.46 (1H, t), 7.53-7.56 (1H, m), 7.72 (1H, d), 7.78 (1H, s). m/z (ES+) (M+H)+=458

Example 23

6-(2'-Chloro-4'-((5-oxo-4,5-dihydro-1,2,4-oxadiazol-3-yl)methyl)biphenyl-4-yl)-3,5-dimethylpyrazine-2-carboxamide

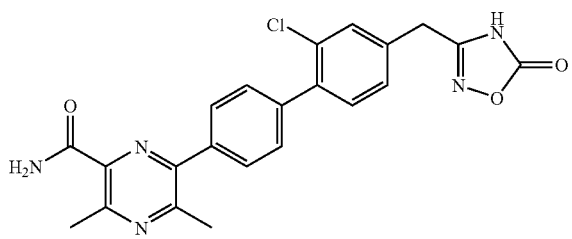

To a degassed solution of 4-(6-carbamoyl-3,5-dimethylpyrazin-2-yl)phenylboronic acid (Intermediate 5-1; 562 mg, 2.07 mmol) in DME (60 mL), methanol (15 mL) and water (15 mL) was added tripotassium phosphate (660 mg, 3.11 mmol), 3-(4-bromo-3-chlorobenzyl)-1,2,4-oxadiazol-5(4H)-one (Intermediate 23-1; 600 mg, 2.07 mmol) followed by (1,1'-bis(diphenylphosphino)ferrocene)-dichloropalladium(II) (DCM adduct) (341 mg, 0.41 mmol). The resulting mixture was stirred at 80° C. under nitrogen for 90 minutes. The reaction mixture was allowed to cool to ambient temperature evaporated and partitioned between DCM (100 mL) and 0.5M HCl (100 mL), the suspension was filtered (difficult as most of the material was a sticky gum) and the resultant material retained. Organic phase separated off, dried by passing through a phase seperating cartridge. Removal of the solvent under reduced pressure gave crude product which was combined with previously filtered material for chromatography. The crude product was purified by preparative HPLC (Waters—Xbridge Prep C18 5 µm), using decreasingly polar mixtures of water (containing 0.1% formic acid) and {MeOH (3):MeCN(1)} as eluents. Fractions containing the desired compound were evaporated to dryness to afford 6-(2'-chloro-4'-((5-oxo-4,5-dihydro-1,2,4-oxadiazol-3-yl)methyl)biphenyl-4-yl)-3,5-dimethylpyrazine-2-carboxamide (269 mg, 29.8%) as a colourless solid.

¹H NMR (400.13 MHz, DMSO-d6) δ 2.65 (3H, s), 2.76 (3H, s), 3.99 (2H, s), 7.38-7.40 (1H, m), 7.48 (1H, d), 7.56-7.62 (5H, m), 7.84-7.87 (2H, m), 8.04 (1H, s) m/z (ES−) (M−H)−=434.57

Intermediate 23-1: 3-(4-Bromo-3-chlorobenzyl)-1,2,4-oxadiazol-5(4H)-one

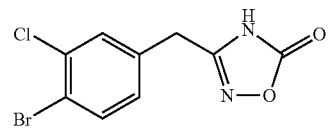

(Z)-Phenyl 2-(4-bromo-3-chlorophenyl)-1-(hydroxyimino)ethylcarbamate (Intermediate 23-2; 2 g, 5.21 mmol) was dissolved in anhydrous toluene (65.2 mL). The resulting solution was stirred at reflux for 16 hours. The cooled reaction mixture was evaporated to dryness and redissolved in DCM (50 mL) and extracted with saturated NaHCO₃ (50 mL). The aqueous layer was acidified with 2M HCl and extracted with EtOAc (3×50 mL). The organic layers were combined and dried over MgSO₄, filtered and evaporated to afford crude product. The crude product was purified by flash silica chromatography {CombiFlash Companion—Presearch Ltd}, column size=120 g, flow rate=85 mL/min, elution gradient 0 to 10% MeOH in DCM}. Pure fractions were evaporated to dryness to afford 3-(4-bromo-3-chlorobenzyl)-1,2,4-oxadiazol-5(4H)-one (1.240 g, 82%) as a colourless solid.

¹H NMR (400.132 MHz, DMSO) δ 3.91 (2H, s), 7.20-7.24 (1H, m), 7.61 (1H, d), 7.74 (1H, d), 12.00-12.50 (1H, broad singlet). m/z (ES−) (M−H)−=287.36

Intermediate 23-2: (Z)-Phenyl 2-(4-bromo-3-chlorophenyl)-1-(hydroxyimino)ethylcarbamate

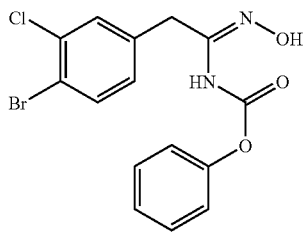

Triethylamine (0.889 mL, 6.38 mmol) was added to (Z)-2-(4-bromo-3-chlorophenyl)-N'-hydroxyacetimidamide (Intermediate 23-3; 1.4 g, 5.31 mmol) in dry dichloromethane (131 mL) at 0° C. The resulting yellow solution was stirred at 0° C. for 1 hour. Phenyl chloroformate (0.815 mL, 6.38 mmol) was added and the reaction mixture stirred at 0° C. for a further 1 hour. The solution was washed sequentially with saturated Na₂CO₃ (50 mL) and water (50 mL×2). The organic layer was dried over MgSO₄, filtered and evaporated to afford crude product ~(Z)-phenyl 2-(4-bromo-3-chlorophenyl)-1-(hydroxyimino)ethylcarbamate (2.70 g, 132%). Used without further purification Intermediate 23-3: (Z)-2-(4-Bromo-3-chlorophenyl)-N'-hydroxyacetimidamide

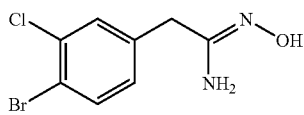

2-(4-Bromo-3-chlorophenyl)acetonitrile (Intermediate 23-4; 2.4 g, 10.41 mmol) in ethanol (15 mL) was added dropwise to potassium carbonate (8.92 g, 64.56 mmol) and hydroxylamine hydrochloride (0.724 g, 10.41 mmol) in ethanol (15 mL) at reflux over a period of 5 minutes. The resulting suspension was stirred at reflux for 8 hours. The reaction mixture was allowed to cool overnight and the salts were filtered and washed with DCM (2×50 mL). The filtrate was evaporated to give crude product. The crude product was purified by flash Silica chromatography {CombiFlash Companion—Presearch Ltd}, column size=120 g, flow rate=85 mL/min, elution gradient 0 to 10% MeOH in DCM}. Pure fractions were evaporated to dryness to afford (Z)-2-(4-bromo-3-chlorophenyl)-N-hydroxyacetimidamide (1.4 g, 51.0%) as a pale brown oil which slowly crystalised.

¹H NMR (400.13 MHz, CDCl₃) δ 3.39 (2H, s), 4.48 (2H, s), 5.30 (0.5H, s), 7.03-7.06 (1H, m), 7.39 (1H, d), 7.55-7.61 (1H, m)

Intermediate 23-4: 2-(4-Bromo-3-chlorophenyl)acetonitrile

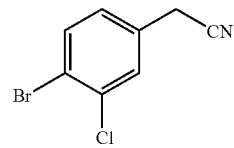

Sodium cyanide (10.91 g, 222.52 mmol) in water (10 mL) was added to a solution of chloroform (20 mL) of N-benzyl-N,N-diethylethanaminium chloride (25.3 g, 111.26 mmol). 1-Bromo-4-(bromomethyl)-2-chlorobenzene (31.64 g, 111.26 mmol) in chloroform (5 mL) was added dropwisely at room temperature. The mixture was stirred at room temperature for 1 h then heated to 45° C. for additional 2 h. The reaction mixture was cooled, separated into two layers and the organic layer was washed with 0.5 N NaOH then brine. The chloroform layer was dried over sodium sulfate, filtered and concentrated. The crude product was purified by flash Silica chromatography {CombiFlash Companion—Presearch Ltd}, column size=330 g, flow rate=100 mL/min, elution gradient 0 to 100% EtOAc in isohexane over 40 minutes. Pure fractions were evaporated to dryness to afford 2-(4-bromo-3-chlorophenyl)acetonitrile (2.430 g, 9.48%) as a orange/yellow oil which solidified on standing.

¹H NMR (400.13 MHz, CDCl₃) δ 3.70 (2H, s), 7.09-7.12 (1H, m), 7.45 (1H, d), 7.62-7.64 (1H, m). m/z (ES−) (M−H)−=228.31; 230.35 & 232.34

Intermediate 23-5: 1-Bromo-4-(bromomethyl)-2-chlorobenzene

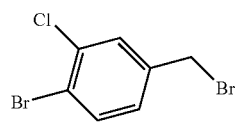

Benzoic peroxyanhydride (3.73 g, 15.41 mmol) was added to a degassed mixture of 1-bromo-2-chloro-4-methylbenzene (24.35 g, 118.50 mmol) and 1-bromopyrrolidine-2,5-dione (23.20 g, 130.35 mmol) in CCl₄ (100 mL) at room temperature under nitrogen. The resulting mixture was stirred at reflux for 18 hrs. The reaction was cooled and washed with water (equal volume); satd sodium thiosulfite (equal volume) and water (equal volume). Mixture dried by passing through a phase seperating cartridge. Solvent removed to give crude 1-bromo-4-(bromomethyl)-2-chlorobenzene (31.7 g, 94%) as pale brown oil which was progressed without further purification.

Example 24

2-(4'-(6-Carbamoyl-3,5-dimethylpyrazin-2-yl)-2,6-difluorobiphenyl-4-yl)acetic acid

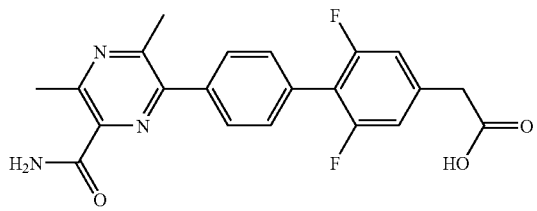

Powdered potassium hydroxide (0.039 g, 0.70 mmol) was added in one portion to methyl 2-(4'-(6-carbamoyl-3,5-dimethylpyrazin-2-yl)-2,6-difluorobiphenyl-4-yl)acetate (Intermediate 24-1; 0.096 g, 0.23 mmol) in tert-butanol (2.00 mL) at 40° C. under nitrogen. The resulting suspension was stirred at 40° C. for 20 minutes. A thick precipitate formed so the reaction was quenched with aq 1M HCl (1.4 mL, 1.40 mmol) and the resulting solution stirred for a further 20 minutes before being evaporated to dryness. The resulting solid was partitioned between water (5 mL) and EtOAc (15 mL). The organic layer was separated and the aqueous re-extracted with EtOAc (2×5 mL). The combined organics were washed with brine (15 mL), dried over $MgSO_4$ and evaporated in vacuo to give product. The crude product was purified by preparative HPLC (Waters—Xbridge Prep C18 5 μm), using decreasingly polar mixtures of water (containing 0.1% formic acid) and {MeOH(3):MeCN(1)} as eluents. Fractions containing the desired compound were evaporated to dryness to afford 2-(4'-(6-carbamoyl-3,5-dimethylpyrazin-2-yl)-2,6-difluorobiphenyl-4-yl)acetic acid (0.052 g, 56.0%) as a colourless solid.

$^1$H NMR (400.13 MHz, DMSO-d6) δ 2.65 (3H, s), 2.76 (3H, s), 3.71 (2H, s), 7.16-7.21 (2H, m), 7.59 (3H, d), 7.87-7.89 (2H, m), 8.05 (1H, s).

m/z (ES+) (M+H)+=398.22

Intermediate 24-1: Methyl 2-(4'-(6-carbamoyl-3,5-dimethylpyrazin-2-yl)-2,6-difluorobiphenyl-4-yl)acetate

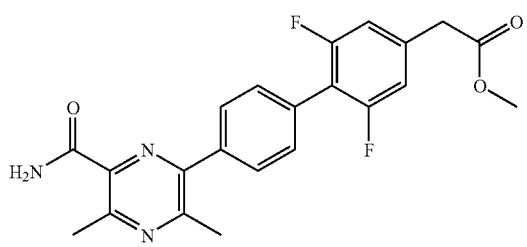

A solution of 4-(6-carbamoyl-3,5-dimethylpyrazin-2-yl)phenylboronic acid (243 mg, 0.90 mmol), methyl 2-(3,5-difluoro-4-(trifluoromethylsulfonyloxy)phenyl)acetate (Intermediate 24-2; 300 mg, 0.90 mmol) and tripotassium phosphate (286 mg, 1.35 mmol) in butyronitrile (2 mL) was put under vacuum and refilled with nitrogen before addition of (1,1'-bis(diphenylphosphino)ferrocene)-dichloropalladium(II) (DCM adduct) (59.1 mg, 0.07 mmol). The reaction mixture was heated in the microwave at 150° C. for 6 hours. The reaction mixture was concentrated and diluted with DCM (25 mL), and washed with water (2×25 mL). The organic layer was dried by passing through a phase seperating cartridge and evaporated to afford crude product. The crude product was purified by flash Silica chromatography {CombiFlash Companion—Presearch Ltd}, column size=12 g, flow rate=30 mL/min, elution gradient 0 to 50% EtOAc in isohexane. Pure fractions were evaporated to dryness to afford methyl 2-(4'-(6-carbamoyl-3,5-dimethylpyrazin-2-yl)-2,6-difluorobiphenyl-4-yl)acetate (96 mg, 26.0%) as a slightly coloured (purple tinge) solid.

$^1$H NMR (400.13 MHz, $CDCl_3$) δ 2.72 (3H, s), 3.00 (3H, s), 3.67 (2H, s), 3.76 (3H, s), 5.47 (1H, s), 6.96-7.01 (2H, m), 7.59-7.61 (2H, m), 7.67-7.70 (2H, m), 7.81 (1H, s). m/z (ES+) M+=412.37

Intermediate 24-2: Methyl 2-(3,5-difluoro-4-(trifluoromethylsulfonyloxy)phenyl)acetate

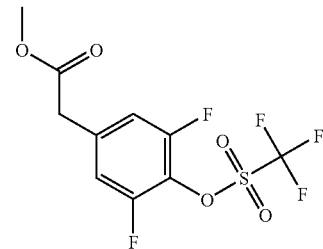

Trifluoromethanesulphonic anhydride (0.854 mL, 5.21 mmol) was added dropwise to a stirred solution of methyl 2-(3,5-difluoro-4-hydroxyphenyl)acetate (Intermediate 24-3; 0.702 g, 3.47 mmol) in DCM (15.06 mL) cooled to 0° C., over a period of 5 minutes under nitrogen. Triethylamine (1.452 mL, 10.42 mmol) was added dropwise over 5 minutes (keeping internal temperature between 5-10° C.) and the resulting solution stirred at room temperature for 4 hours under nitrogen. The reaction mixture was diluted with DCM (100 mL), and washed sequentially with water (100 mL), saturated $NaHCO_3$ (100 mL), and water (100 mL). The organic layer was dried by passing through a phase seperating cartridge and evaporated to afford crude product. The crude product was purified by flash silica chromatography, elution gradient 0 to 20% EtOAc in isohexane. Pure fractions were evaporated to dryness to afford methyl 2-(3,5-difluoro-4-(trifluoromethylsulfonyloxy)phenyl)acetate (0.930 g, 80%) as a straw yellow oil.

¹H NMR (400.13 MHz, CDCl₃) δ 3.63 (2H, s), 3.74 (3H, s), 7.02-7.06 (2H, m)

Intermediate 24-3: Methyl 2-(3,5-difluoro-4-hydroxyphenyl)acetate

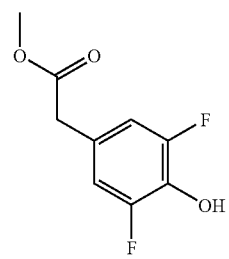

Tribromoborane (2.357 mL, 24.93 mmol) was added dropwise to 2-(3,5-difluoro-4-methoxyphenyl)acetic acid (0.84 g, 4.16 mmol) in dichloromethane (5 mL) at ambient temperature under nitrogen. The resulting solution was stirred at ambient temperature for 16 hours. Methanol (8.41 mL, 207.76 mmol) was added dropwise (—care reaction is vigorous and exothermic—mixture maintained a reflux during the addition) and the mixture was stirred for a further 20 minutes. The reaction mixture was evaporated to dryness and redissolved in DCM (50 mL), and washed sequentially with saturated NaHCO3 (50 mL) and water (50 mL). The organic layer was dried by passing through a phase seperating cartridge and evaporated to afford desired product methyl 2-(3,5-difluoro-4-hydroxyphenyl)acetate (0.660 g, 79%).

¹H NMR (400.13 MHz, CDCl₃) δ 3.52 (2H, s), 3.71 (3H, s), 5.32 (1H, s), 6.81-6.86 (2H, m). m/z (ES−) (M−H)−=201.27; HPLC tR=1.78 min Example 25

2-(4'-(6-carbamoyl-3,5-dimethylpyrazin-2-yl)-2-fluorobiphenyl-4-yl)acetic acid

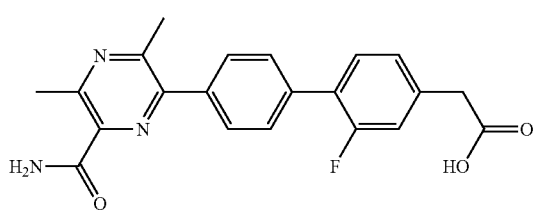

Powdered potassium hydroxide (72.7 mg, 1.30 mmol) was added in one portion to methyl 2-(4'-(6-carbamoyl-3,5-dimethylpyrazin-2-yl)-2-fluorobiphenyl-4-yl)acetate (Intermediate 25-1; 170 mg, 0.43 mmol) in tert-butanol (2.0 mL) at 40° C. under nitrogen. The resulting suspension was stirred at 40° C. for 20 minutes. A thick precipitate formed so the reaction was quenched with acetic acid (0.124 mL, 2.16 mmol) in ethanol (20.0 mL) and the resulting solution stirred for a further 20 minutes before being evaporated to dryness. The resulting solid was partitioned between water (5 mL) and EtOAc (15 mL). The aqueous layer showed a pH=4~5. The organic layer was separated and the aqueous re-extracted with EtOAc (2×5 mL). The combined organics were washed with brine (15 mL), dried over MgSO₄ and evaporated in vacuo to give product. This was washed with Ether (5 mL) and dried under vacuum at room temperature to give an off white solid. The crude product was purified by preparative HPLC (Waters—Xbridge Prep C18 5 μm), using decreasingly polar mixtures of water (containing 0.1% formic acid) and {MeOH (3):MeCN(1)} as eluents. Fractions containing the desired compound were evaporated to dryness to afford 2-(4'-(6-carbamoyl-3,5-dimethylpyrazin-2-yl)-2-fluorobiphenyl-4-yl)acetic acid (80 mg, 48.8%) as a colourless ¹H NMR (400.13 MHz, DMSO-d6) δ 2.64 (3H, s), 2.76 (3H, s), 3.67 (2H, s), 7.21-7.27 (2H, m), 7.56 (2H, t), 7.67-7.69 (2H, m), 7.85-7.87 (2H, m), 8.03 (1H, s)

m/z (ES+) (M+H)+=380.22

Intermediate 25-1: Methyl 2-(4'-(6-carbamoyl-3,5-dimethylpyrazin-2-yl)-2-fluorobiphenyl-4-yl)acetate

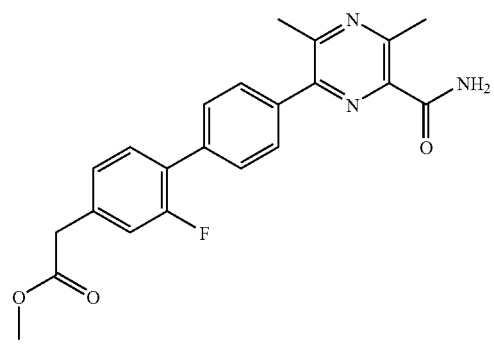

A solution of 3,5-dimethyl-6-(4-(4,4,5,5-tetramethyl-1,3,2-dioxaborolan-2-yl)phenyl)pyrazine-2-carboxamide (353 mg, 1 mmol), methyl 2-(3-fluoro-4-(trifluoromethylsulfonyloxy)phenyl)acetate (Intermediate 25-2; 411 mg, 1.30 mmol) and tripotassium phosphate (318 mg, 1.50 mmol) in DME (6 mL), ethanol (3.00 mL) and water (1.500 mL) was put under vacuum and refilled with nitrogen before addition of (1,1'-bis(diphenylphosphino)ferrocene)-dichloropalladium(II) (DCM adduct) (65.8 mg, 0.08 mmol). The reaction mixture was heated to and left to stir overnight for 16 hrs. The reaction mixture was allowed to cool to room temperature and then evaporated. The residue was partitioned between water (20 mL) and EtOAc (50 mL). The aqueous was re-extracted with EtOAc (2×10 mL) and the combined organics washed with brine (20 mL), dried (MgSO₄) and evaporated to give crude product. The crude product was purified by flash silica chromatography, elution gradient 0 to 50% EtOAc in isohexane on 40 g silicycle column. Pure fractions were evaporated to dryness to afford methyl 2-(4'-(6-carbamoyl-3,5-dimethylpyrazin-2-yl)-2-fluorobiphenyl-4-yl)acetate (180 mg, 45.8%) as a white solid.

¹H NMR (400.13 MHz, DMSO-d6) δ 2.64 (3H, s), 2.79 (3H, s), 3.68 (3H, s), 3.77 (2H, s), 7.23-7.25 (2H, m), 7.55 (1H, t), 7.67-7.70 (2H, m), 7.80-7.82 (2H, m).

m/z (ES+) (M+H)+=394.37

Intermediate 25-2: Methyl 2-(3-fluoro-4-(trifluoromethylsulfonyloxy)phenyl)acetate

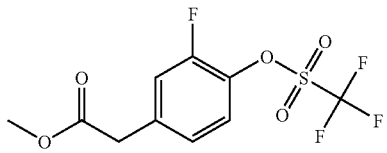

Trifluoromethanesulphonic anhydride (2.67 mL, 16.29 mmol) was added dropwise to a stirred solution of methyl 2-(3-fluoro-4-hydroxyphenyl)acetate (85% by LCMS) (2 g, 10.86 mmol) in DCM (47.1 mL) cooled to 0° C., over a period of 5 minutes under nitrogen. Triethylamine (4.54 mL, 32.58 mmol) was added dropwise over 5 minutes (keeping internal temperature between 5-10° C.) and the resulting solution stirred at room temperature for 4 hours under nitrogen. The reaction mixture was diluted with DCM (100 mL), and washed sequentially with water (100 mL), saturated NaHCO$_3$ (100 mL), and water (100 mL). The organic layer was dried by passing through a phase seperating cartridge and evaporated to afford crude product. The crude product was purified by flash silica chromatography, elution gradient 0 to 20% EtOAc in isohexane. Pure fractions were evaporated to dryness to afford methyl 2-(3-fluoro-4-(trifluoromethylsulfonyloxy)phenyl)acetate (2.250 g, 65.5%) as a straw yellow oil.

$^1$H NMR (400.13 MHz, CDCl$_3$) δ 3.64 (2H, s), 3.73 (3H, s), 7.11-7.14 (1H, m), 7.22-7.31 (2H, m). m/z (ES−) (M−H)−=315.19

Example 26 and Example 27

2-(4'-(6-Carbamoyl-3,5-dimethylpyrazin-2-yl)-2-chloro-2'-fluorobiphenyl-4-yl)propanoic acid enantiomers 1 and 2

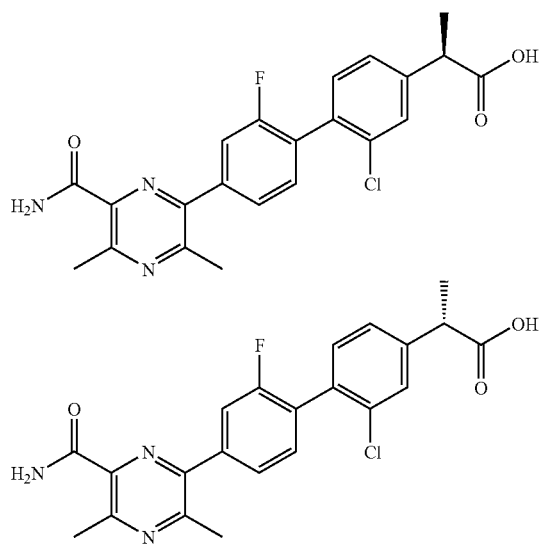

Powdered potassium hydroxide (432 mg, 7.69 mmol) was added in one portion to methyl 2-(4'-(6-carbamoyl-3,5-dimethylpyrazin-2-yl)-2-chloro-2'-fluorobiphenyl-4-yl)propanoate (Intermediate 26-1; 680 mg, 1.54 mmol) in tert-butanol (10 mL). The resulting yellow cloudy suspension was stirred at 40° C. for 1 hour. The reaction mixture was quenched with acetic acid (0.705 mL, 12.31 mmol) in ethanol (2 mL) and the resulting solution stirred for a further 10 minutes before being evaporated to dryness. The resulting solid was partitioned between water (20 mL) and DCM (20 mL). The organic layer was separated and the aqueous re-extracted with DCM (20 mL). The combined organics were evaporated in vacuo to give crude product as an off white solid (578 mg). This crude product was purified by preparative HPLC (Waters XBridge Prep C18 OBD column, 5μ silica, 50 mm diameter, 150 mm length), using decreasingly polar mixtures of water (containing 0.1% formic acid) and MeOH as eluents. Fractions containing the desired compound were evaporated to dryness to afford racemic 2-(4'-(6-carbamoyl-3,5-dimethylpyrazin-2-yl)-2-chloro-2'-fluorobiphenyl-4-yl)propanoic acid (359 mg, 54.5%) as a white solid.

1H NMR (400.132 MHz, DMSO) δ 1.43 (3H, d), 2.67 (3H, s), 2.76 (3H, s), 3.81 (1H, q), 7.42 (2H, m), 7.51 (2H, m), 7.62 (1H, s), 7.70 (1H, m), 7.80 (1H, m), 8.11 (1H, s), 12.51 (1H, s). m/z (ES+) (M+H)+=428

Chiral separation of racemic 2-(4'-(6-carbamoyl-3,5-dimethylpyrazin-2-yl)-2-chloro-2'-fluorobiphenyl-4-yl)propanoic acid. The crude product was purified by preparative chiral-HPLC on a Merck 50 mm 20 μm Chiralpak AD column, eluting isocratically with 30% EtOH in 70% isohexane (acidified with AcOH 0.2%) as eluent. The fractions containing the desired compounds were evaporated to dryness and dried under high vacuum overnight to afford:

(i) 2-(4'-(6-carbamoyl-3,5-dimethylpyrazin-2-yl)-2-chloro-2'-fluorobiphenyl-4-yl)propanoic acid (enantiomer 1) (161 mg, 46.0%) as a white solid $^1$H NMR (400.132 MHz, DMSO) δ 1.44 (3H, d), 2.69 (3H, s), 2.78 (3H, s), 3.83 (1H, q), 7.40 (1H, m), 7.46 (1H, d), 7.53 (2H, m), 7.64 (1H, s), 7.71 (1H, m), 7.81 (1H, m), 8.12 (1H, s), 12.49 (1H, s). m/z (ES+) (M+H)+=428.10.

This enantiomer proved to be the more potent DGAT1 inhibitor and has been assigned the S-configuration by analogy to Examples 8 and 9. This was subsequently confirmed by single crystal diffraction at 200K.

and (ii) 2-(4'-(6-carbamoyl-3,5-dimethylpyrazin-2-yl)-2-chloro-2'-fluorobiphenyl-4-yl)propanoic acid (enantiomer 2) (146 mg, 41.7%) as a white solid.

$^1$H NMR (400.132 MHz, DMSO) δ 1.44 (3H, d), 2.68 (3H, s), 2.78 (3H, s), 3.82 (1H, q), 7.40 (1H, m), 7.46 (1H, d), 7.53 (2H, m), 7.64 (1H, s), 7.71 (1H, m), 7.81 (1H, m), 8.12 (1H, s), 12.40 (1H, s). m/z (ES+) (M+H)+=428.17.

This enantiomer proved to be the less potent DGAT1 inhibitor and has been assigned the R-configuration by analogy to Examples 8 and 9.

Intermediate 26-1: Methyl 2-(4'-(6-carbamoyl-3,5-dimethylpyrazin-2-yl)-2-chloro-2'-fluorobiphenyl-4-yl)propanoate

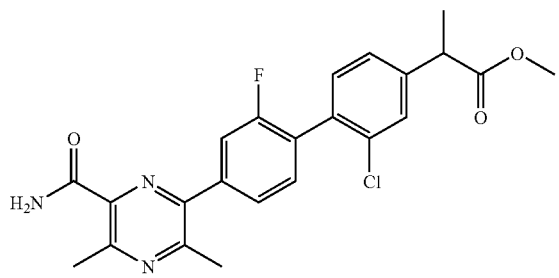

A solution of 4-(6-carbamoyl-3,5-dimethylpyrazin-2-yl)-2-fluorophenyl trifluoromethanesulfonate (Intermediate 6-4; 703 mg, 1.79 mmol) and methyl 2-(3-chloro-4-(4,4,5,5-tetramethyl-1,3,2-dioxaborolan-2-yl)phenyl)propanoate (Intermediate 8-2; 580 mg, 1.79 mmol), lithium chloride (133 mg, 3.13 mmol) and potassium phosphate, tri-basic (455 mg, 2.14 mmol) in DME (20 mL), methanol (10 mL) and water (5 mL) was thoughroughly degassed. The mixture was treated with PdCl$_2$(dppf)-DCM adduct (73.0 mg, 0.09 mmol), degassed again and the atmosphere replaced with nitrogen before being heated to 85° C. for 17 hours. The reaction mixture was allowed to cool and evaporated, the residue was partitioned between EtOAc (100 mL), and water (75 mL) and the aqueous layer was further extracted with EtOAc (100 mL). The organic layers were combined and washed with saturated brine (100 mL), dried over MgSO$_4$, filtered and evaporated to afford crude product. The crude product was purified by flash silica chromatography, elution gradient 0 to 60% EtOAc in isohexane. Pure fractions were evaporated to dryness to afford methyl 2-(4'-(6-carbamoyl-3,5-dimethylpyrazin-2-yl)-2-chloro-2'-fluorobiphenyl-4-yl)propanoate (681 mg, 86%) as a cream solid.

$^1$H NMR (400.132 MHz, DMSO) δ 1.46 (3H, d), 2.66 (3H, s), 2.77 (3H, s), 3.64 (3H, s), 3.95 (1H, q), 7.37-7.40 (1H, m), 7.45 (1H, d), 7.51 (1H, t), 7.55-7.55 (1H, m), 7.63 (1H, s), 7.69-7.71 (1H, m), 7.78-7.81 (1H, m), 8.11 (1H, s). m/z (ES+) (M+H)+=442

Example 28

1-(4'-(6-Carbamoyl-3,5-dimethylpyrazin-2-yl)-2,6-difluorobiphenyl-4-yl)cyclopropanecarboxylic acid

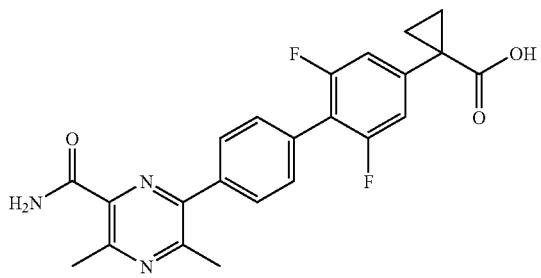

Powdered potassium hydroxide (91 mg, 1.62 mmol) was added in one portion to methyl 1-(4'-(6-carbamoyl-3,5-dimethylpyrazin-2-yl)-2,6-difluorobiphenyl-4-yl)cyclopropanecarboxylate (Intermediate 28-1; 142 mg, 0.32 mmol) in tert-butanol (10 mL). The resulting yellow cloudy suspension was stirred at 40° C. for 1 hour. The reaction mixture was quenched with acetic acid (0.149 mL, 2.60 mmol) in ethanol (2 mL) and the resulting solution stirred for a further 10 minutes before being evaporated to dryness. The resulting solid was partitioned between water (20 mL) and ethyl acetate (20 mL). An insoluble solid was filtered off. The organic layer was separated and the aqueous re-extracted with ethyl acetate (20 mL). The combined organics were evaporated in vacuo to give crude product as an off white solid. The crude solid was triturated with mixture of DCM (3 mL) and methanol (3 mL) to give a solid which was collected by filtration and dried under vacuum to give 1-(4'-(6-carbamoyl-3,5-dimethylpyrazin-2-yl)-2,6-difluorobiphenyl-4-yl)cyclopropanecarboxylic acid (52.0 mg, 37.8%) as a white solid.

$^1$H NMR (400.132 MHz, DMSO) δ 1.30 (2H, m), 1.51 (2H, m), 2.66 (3H, s), 2.79 (3H, s), 7.25 (2H, d), 7.60 (3H, d), 7.89 (2H, d), 8.06 (1H, s), 12.58 (1H, s).

m/z (ES+) (M+H)+=424

Intermediate 28-1: Methyl 1-(4'-(6-carbamoyl-3,5-dimethylpyrazin-2-yl)-2,6-difluorobiphenyl-4-yl)cyclopropanecarboxylate

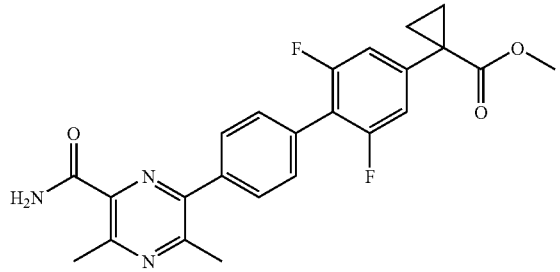

A solution of 4-(6-carbamoyl-3,5-dimethylpyrazin-2-yl)phenylboronic acid (226 mg, 0.83 mmol), methyl 1-(3,5-difluoro-4-(trifluoromethylsulfonyloxy)phenyl)cyclopropanecarboxylate (Intermediate 28-2; 300 mg, 0.83 mmol), lithium chloride (70.6 mg, 1.67 mmol) and tripotassium phosphate (265 mg, 1.25 mmol) in butyronitrile (2 mL) was degassed for 10 minutes then put under vacuum and refilled with nitrogen before addition of (1,1'-bis(diphenylphosphino)ferrocene)-dichloropalladium(II) (DCM adduct) (137 mg, 0.17 mmol). The reaction mixture was heated in the microwave at 150° C. for 1 hours. The crude product was purified by flash silica chromatography, elution gradient 0 to 90% EtOAc in isohexane. Pure fractions were evaporated to dryness to afford methyl 1-(4'-(6-carbamoyl-3,5-dimethylpyrazin-2-yl)-2,6-difluorobiphenyl-4-yl)cyclopropanecarboxylate (160 mg, 43.9%)

$^1$H NMR (400.132 MHz, DMSO) δ 1.34 (2H, q), 1.53 (2H, q), 2.65 (3H, s), 2.76 (3H, s), 3.62 (3H, s), 7.27 (2H, d), 7.59 (3H, d), 7.88 (2H, d), 8.05 (1H, s).

m/z (ES+) (M+H)+=438

Intermediate 28-2: Methyl 1-(3,5-difluoro-4-(trifluoromethylsulfonyloxy)phenyl)cyclopropanecarboxylate

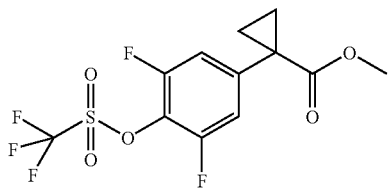

Methyl 1-(3,5-difluoro-4-hydroxyphenyl)cyclopropanecarboxylate (Intermediate 28-3; 635 mg, 2.78 mmol), 1,1,1-trifluoro-N-phenyl-N-(trifluoromethylsulfonyl)methanesulfonamide (994 mg, 2.78 mmol) and potassium carbonate (1154 mg, 8.35 mmol) were suspended in THF (15 mL) and sealed into a microwave tube. The reaction was heated to 120° C. for 8 minutes in the microwave reactor and cooled to RT. The suspension was filtered, the solid was washed with EtOAc (20 mL) and the filtrate was evaporated to afford crude product. The crude product was purified by flash silica chromatography, elution gradient 10 to 20% EtOAc in isohexane. Pure fractions were evaporated to dryness to afford methyl 1-(3,5-difluoro-4-(trifluoromethylsulfonyloxy)phenyl)cyclopropanecarboxylate (968 mg, 97%) as a colourless oil.

$^1$H NMR (400.132 MHz, DMSO) δ 1.35 (2H, m), 1.52 (2H, m), 3.58 (3H, s), 7.55 (2H, m)

Intermediate 28-3: Methyl 1-(3,5-difluoro-4-hydroxyphenyl)cyclopropanecarboxylate

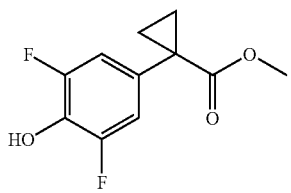

Tribromoborane (0.666 ml, 7.04 mmol) was added dropwise to methyl 1-(3,5-difluoro-4-methoxyphenyl)cyclopropanecarboxylate (Intermediate 28-4; 1.4216 g, 5.87 mmol) in dichloromethane (46.2 mL) at 0° C. under nitrogen. The resulting solution was stirred at 0° C. for 1 hour. The reaction mixture was added dropwise to methanol (11.87 mL, 293.45 mmol) (care reaction is vigorous and exothermic—MeOH kept in ice bath) and the mixture was stirred for a further 20 minutes. The reaction mixture was evaporated to dryness and redissolved in DCM (50 mL), and washed sequentially with saturated NaHCO$_3$ (50 mL) and water (50 mL). The organic layer was dried with MgSO$_4$ and evaporated to afford crude product. The crude product was purified by flash silica chromatography, eluted at 25% EtOAc in isohexane. Pure fractions were evaporated to dryness to afford methyl 1-(3,5-difluoro-4-hydroxyphenyl)cyclopropanecarboxylate (0.657 g, 49.1%) as a white solid.

$^1$H NMR (400.132 MHz, CDCl$_3$) d1.08 (2H, q), 1.52 (2H, q), 3.57 (3H, s), 5.08 (1H, s), 6.78-6.86 (2H, m)m/z (ES–), (M–H)–=227

Intermediate 28-4: Methyl 1-(3,5-difluoro-4-methoxyphenyl)cyclopropanecarboxylate

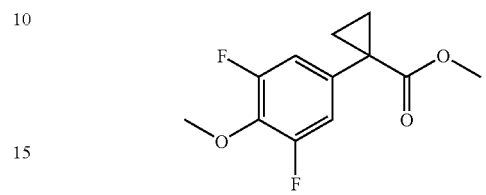

Sodium hydride (0.326 g, 8.14 mmol) was added in one portion to methyl 2-(3,5-difluoro-4-methoxyphenyl)acetate (1.76 g, 8.14 mmol) in DMF (46.3 mL) at 0° C. under nitrogen. The resulting suspension was stirred at 0° C. for 10 minutes. Following this 1,2-dibromoethane (0.772 mL, 8.96 mmol) was added to the reaction mixture and the solution was stirred for 5 minutes. Additional sodium hydride (0.326 g, 8.14 mmol) was then added and the reaction allowed to stir for 2 hours. The reaction mixture was quenched with saturated NH$_4$Cl (50 mL). The reaction mixture was diluted with EtOAc (75 mL), and washed sequentially with water (4×50 mL) and saturated brine (50 mL). The organic layer was evaporated to afford crude product. The crude product was purified by flash silica chromatography, elution at 10% EtOAc in isohexane. Pure fractions were evaporated to dryness to afford methyl 1-(3,5-difluoro-4-methoxyphenyl)cyclopropanecarboxylate (1.540 g, 78%) as a colourless gum.

$^1$H NMR (400.132 MHz, CDCl$_3$) d1.15 (2H, q), 1.60 (2H, q), 3.64 (3H, s), 3.98 (3H, s), 6.85-6.91 (2H, m)

Example 29

3,5-Dimethyl-6-(2'-methyl-4'-((5-oxo-2,5-dihydro-1,2,4-oxadiazol-3-yl)methyl)biphenyl-4-yl)pyrazine-2-carboxamide

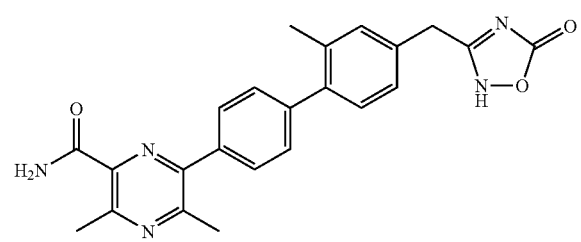

3-(4-Iodo-3-methylbenzyl)-1,2,4-oxadiazol-5(2H)-one (Intermediate 29-1; 200 mg, 0.63 mmol) and 2M sodium carbonate (aq) (0.633 mL, 1.27 mmol), tetrakis(triphenylphosphine)palladium(0) (45.3 mg, 0.04 mmol) in DME (4 mL) was degassed and then stirred at 85° C. for 17 hours under nitrogen. The reaction mixture was evaporated and partitioned between EtOAc (75 mL) and saturated brine (15 mL). The organic layer was dried over MgSO$_4$, filtered and evaporated to afford crude product. The crude product was purified by flash silica chromatography, elution gradient 0 to 100% EtOAc in isohexane. Fractions were evaporated to dryness to afford a cream solid (117 mg). The product was purified by preparative HPLC (Waters XBridge Prep C18 OBD column, 5μ silica, 50 mm diameter, 150 mm length), using decreasingly polar mixtures of water (containing 0.1% formic acid) and MeOH as eluents. Fractions containing the desired compound were evaporated to dryness to afford 3,5-dimethyl-6-(2'-methyl-4'-((5-oxo-2,5-dihydro-1,2,4-oxadiazol-3-yl)methyl)biphenyl-4-yl)pyrazine-2-carboxamide (13 mg, 0.031 mmol, 4.95%)

$^1$H NMR (400.132 MHz, DMSO) δ 2.23 (3H, s), 2.60 (3H, s), 2.70 (3H, s), 3.84 (2H, s), 7.19 (3H, m), 7.41 (2H, d), 7.49 (1H, m), 7.77 (2H, d), 7.98 (1H, s), 12.26 (1H, s). m/z (ES−) (M−H)−=414

Intermediate 29-1: 3-(4-iodo-3-methylbenzyl)-1,2,4-oxadiazol-5(4H)-one

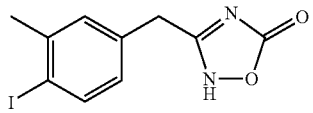

(Z)-Phenyl 1-(hydroxyimino)-2-(4-iodo-3-methylphenyl) ethylcarbamate (Intermediate 29-2; 1.67 g, 4.07 mmol) was dissolved in anhydrous toluene (30 mL). The resulting solution was stirred at reflux for 16 hours. The cooled reaction mixture was evaporated to dryness and redissolved in DCM (50 mL) and extracted with saturated NaHCO$_3$ (50 mL). The aqueous layer was acidified with 2M HCl and extracted with EtOAc (3×50 mL). The organic layers were combined and dried over MgSO$_4$, filtered and evaporated to afford desired product. 3-(4-iodo-3-methylbenzyl)-1,2,4-oxadiazol-5(4H)-one (0.787 g, 61.2%) as a yellow solid.

$^1$H NMR (400.132 MHz, DMSO) δ 2.34 (3H, s), 3.81 (2H, s), 6.87 (1H, d), 7.27 (1H, s), 7.78 (1H, d), 12.25 (1H, s). m/z (ES−) (M−H)−=315

Intermediate 29-2: (Z)-Phenyl 1-(hydroxyimino)-2-(4-iodo-3-methylphenyl)ethylcarbamate

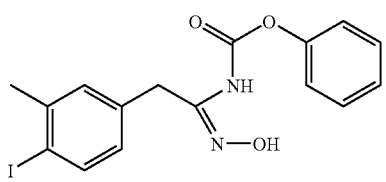

Triethylamine (0.651 mL, 4.67 mmol) was added to (Z)—N'-hydroxy-2-(4-iodo-3-methylphenyl)acetimidamide (Intermediate 29-3; 1.13 g, 3.90 mmol) in dry dichloromethane (30 mL) at 0° C. The resulting yellow solution was stirred at 0° C. for 1 hour. Phenyl chloroformate (0.598 mL, 4.67 mmol) was added and the reaction mixture stirred at 0° C. for a further 1 hour. The solution was washed sequentially with saturated Na$_2$CO$_3$ (50 mL) and water (50 mL×2). The organic layer was dried over MgSO$_4$, filtered and evaporated to afford (Z)-phenyl 1-(hydroxyimino)-2-(4-iodo-3-methylphenyl) ethylcarbamate (1.675 g, 105%) as crude product.

$^1$H NMR (400.132 MHz, DMSO) δ 2.41 (3H, s), 3.38 (2H, s), 6.69 (1H, s), 6.99 (1H, d), 7.42 (7H, m), 7.82 (1H, d). m/z (ES+) (M+H)+=411

Intermediate 29-3: (Z)—N'-hydroxy-2-(4-iodo-3-methylphenyl)acetimidamide

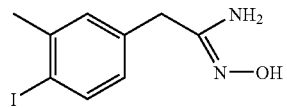

2-(4-Iodo-3-methylphenyl)acetonitrile (2 g, 7.78 mmol) in ethanol (30 mL) was added dropwise to potassium carbonate (6.67 g, 48.24 mmol) and hydroxylamine hydrochloride (0.541 g, 7.78 mmol) in ethanol (30 mL) at reflux over a period of 5 minutes. The resulting suspension was stirred at reflux for 8 hours. The reaction mixture was allowed to cool overnight and the salts were filtered and washed with DCM (2×50 mL). The filtrate was evaporated to give crude product. The crude product was purified by flash silica chromatography on a combi flash companion 40 g cartridge, elution gradient 0 to 30% MeOH in DCM. Pure fractions were evaporated to dryness to afford (Z)—N'-hydroxy-2-(4-iodo-3-methylphenyl)acetimidamide (1.135 g, 50.3%) as a yellow gum.

$^1$H NMR (400.132 MHz, DMSO) δ 2.32 (3H, s), 3.18 (2H, s), 5.35 (2H, s), 6.84 (1H, d), 7.22 (1H, s), 7.70 (1H, d), 8.86 (1H, s). m/z (ES+) (M+H)+=291

Example 30

6-(4'-(2-Amino-2-oxoethyl)-2'-chlorobiphenyl-4-yl)-3,5-dimethylpyrazine-2-carboxamide

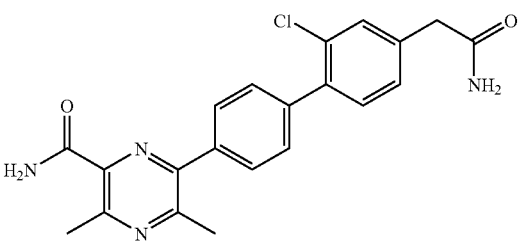

Methyl 2-(4'-(6-carbamoyl-3,5-dimethylpyrazin-2-yl)-2-chlorobiphenyl-4-yl)acetate (Intermediate 1-1; 60 mg, 0.15 mmol) and ammonia (7M in methanol) (2091 μL, 14.64 mmol) were sealed into a microwave tube. The reaction was heated to 140° C. for 1 hour in the microwave reactor and cooled to RT. Removal of the solvent under reduced pressure gave crude product. The crude product was purified by preparative HPLC (Waters—Xbridge Prep C18 5 μm), using decreasingly polar mixtures of water (containing 0.1% formic acid) and {MeOH(3):MeCN(1)} as eluents. Fractions containing the desired compound were evaporated to dryness to afford 6-(4'-(2-amino-2-oxoethyl)-2'-chlorobiphenyl-4-yl)-3,5-dimethylpyrazine-2-carboxamide (16.20 mg, 28.0%) as a colourless solid.

$^1$H NMR (400.13 MHz, CDCl$_3$) δ 2.73 (3H, s), 3.00 (3H, s), 3.63 (2H, s), 5.49 (3H, s), 7.30 (1H, d), 7.40 (1H, d), 7.46 (1H, s), 7.57-7.61 (2H, m), 7.67 (2H, d), 7.82 (1H, s)
m/z (ES+) (M+H)+=395.28

Example 31

(2S)-2-[4-[4-(6-carbamoyl-3,5-dimethylpyrazin-2-yl)-2-fluorophenyl]-3-chlorophenyl]propanoic acid

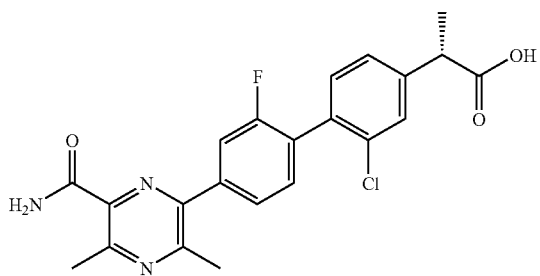

2-[4-[4-(6-Carbamoyl-3,5-dimethylpyrazin-2-yl)-2-fluorophenyl]-3-chlorophenyl]prop-2-enoic acid (Intermediate 31-10; 142 g, 283.44 mmol), bis(1,5-cyclooctadiene) rhodium(I) tetrafluoroborate (1.381 g, 3.40 mmol), (R)-1-[(Sp)-2-(di-tert-butylphosphino)ferrocenyl]ethylbis(2-methylphenyl)phosphine (2.102 g, 3.68 mmol) in degassed methanol (2.5 L) and degassed toluene (836 mL) were stirred under an atmosphere of hydrogen at 5 bar and 45° C. for 4 hours. Chiral HPLC analysis (chiralpak AD 5 μm, 250 mm×4.6 mm column, eluted with 60% isohexane/40% ethanol/0.2% acetic acid, retention time for required enantiomer 14.5 minutes) indicated the ratio of desired to undesired enantiomer was 87:13. The solvent was removed in vacuo. The crude product was dissolved in 5% methanol/dichloromethane and then chromatographed on silica (5 Kg of Merck lichro prep silica 15-25 μm, 200 mm diameter column), eluting with a solvent mixture of 5% methanol/dichloromethane. Pure fractions were evaporated to dryness to afford the mixture of the enantiomers, chiral prep HPLC chromatography (5 Kg of chiralpak AD 20 μm, 200 mm diameter column, eluted with 70% isohexane/30% ethanol/ 0.2% acetic acid, retention time for required enantiomer 17 minutes) then gave (2S)-2-[4-[4-(6-carbamoyl-3,5-dimethylpyrazin-2-yl)-2-fluorophenyl]-3-chlorophenyl]propanoic acid (58 g, 40%, 99% ee) as a white solid.

$^1$H NMR (400 MHz, DMSO-d6) δ1.43 (3H d, J=7.2 Hz), 2.66 (3H, s), 2.77 (3H, s), 3.81 (1H q, J=7.1 Hz), 7.38-7.45 (2H, m), 7.51 (1H t, J=7.8 Hz), 7.54 (1H d, J=1.9 Hz), 7.63 (1H, s), 7.69-7.71 (1H, m), 7.78-7.81 (1H, m), 8.11 (1H, s), 12.51 (1H, s)

m/z (ES+) (M+H)+=428

Intermediate 31-1: Methyl 2-(3-chloro-4-hydroxyphenyl)acetate

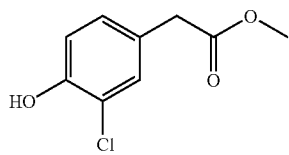

A solution of 2-(3-chloro-4-hydroxyphenyl)acetic acid (1000 g, 5359 mmol) and sulfuric acid (0.029 L, 535 mmol) in methanol (10 L) was stirred at reflux for 3 hours. The reaction mixture was cooled to 25° C. The solvent was then removed in vacuo. Ethyl acetate (5.0 L) was added and the solution was washed with water (4.0 L), brine (2.0 L), dried (magnesium sulphate), filtered and the solvent was removed in vacuo. Gave methyl 2-(3-chloro-4-hydroxyphenyl)acetate (1078 g, 99%) as an orange oil.

$^1$H NMR (400 MHz, CDCl$_3$) δ 3.53 (2H, s), 3.70 (3H, s), 5.53 (1H, s), 6.96 (1H, d), 7.08 (1H, dd), 7.25 (1H+CHCl3, m).

m/z (ES−) (M−H)−=199

Intermediate 31-2: Methyl 2-[3-chloro-4-(trifluoromethylsulfonyloxy)phenyl]acetate

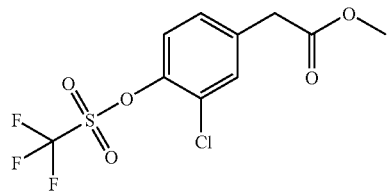

Pyridine (0.068 L, 841 mmol) was added to a stirred solution of methyl 2-(3-chloro-4-hydroxyphenyl)acetate (Intermediate 31-1; 150 g, 672 mmol) in toluene (1.0 L) at 25° C. The reaction was cooled to −5° C. Trifluoromethanesulfonic anhydride (130 mL, 773 mmol) was then added over a period of 45 minutes, keeping the temperature below 0° C. The reaction was then warmed to room temperature and the resulting suspension left to stand over night. The reaction was quenched with sodium phosphate (50 g in 500 mL water). Ethyl acetate (1.0 L) was added. The organic layer was separated and the aqueous layer extracted with ethyl acetate (1.0 L). The organics were combined and washed with 50% brine/ water (500 mL), dried (magnesium sulphate), filtered and the solvent removed in vacuo. The crude product was then azeotroped with toluene (1.0 L). Gave 2-[3-chloro-4-(trifluoromethylsulfonyloxy)phenyl]acetate (209 g, 93%) as a pale orange oil that solidified on standing.

$^1$H NMR (400 MHz, DMSO-d6) δ 3.64 (3H, s), 3.81 (2H, s), 7.43-7.46 (1H, m), 7.60 (1H d, J=8.5 Hz), 7.71 (1H d, J=2.1 Hz)

m/z (ES−) (M−H)−=331

Intermediate 31-3: Methyl 2-[3-chloro-4-(4,4,5,5-tetramethyl-1,3,2-dioxaborolan-2-yl)phenyl]acetate

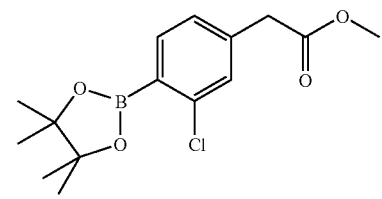

To a degassed solution of methyl 2-(3-chloro-4-(trifluoromethylsulfonyloxy)phenyl)acetate (Intermediate 31-2; 865 g, 2600 mmol) in 1,4-dioxane (8.6 L) was added potassium acetate (766 g, 7800 mmol), bis(pinacolato)diboron (806 g, 3172 mmol) and PdCl$_2$(dppf)-CH$_2$Cl$_2$ adduct (37.2 g, 45.5 mmol). The suspension was stirred at 25° C. for 30 minutes and then heated to reflux for 27 hours, monitoring by LCMS (230 nm). The reaction was cooled to 25° C., then filtered through a glass sinter. The solid obtained was washed with 1,4-dioxane (5.0 L) and discarded. The solvent was then removed in vacuo from the combined filtrates to give the crude product. Gave methyl 2-[3-chloro-4-(4,4,5,5-tetramethyl-1,3,2-dioxaborolan-2-yl)phenyl]acetate (1168 g) as a brown sludge, proton NMR strength indicated 52% pure (therefore 607 g, 75%). The material was used crude in the next stage.

$^1$H NMR (400.132 MHz, CDCl$_3$) δ 1.36 (12H, s), 3.59 (2H, s), 3.68 (3H, s), 7.13-7.16 (1H, m), 7.28-7.28 (1H, m), 7.65 (1H, d)

Intermediate 31-4: 2-Fluoro-4-(4,4,5,5-tetramethyl-1,3,2-dioxaborolan-2-yl)phenol

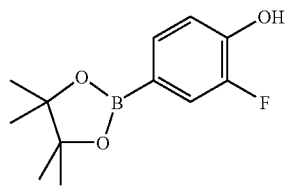

A solution of 4-bromo-2-fluorophenol (143 mL, 1308 mmol) in dioxane (2.5 L) was degassed with nitrogen for a period of 30 minutes. Potassium acetate (514 g, 5235 mmol), bis(pinacolato)diboron (399 g, 1570 mmol), (1,1'-bis(diphenylphosphino)ferrocene)-dichloropalladium(II) (7.54 g, 9.2 mmol) and 1,1'-bis(diphenylphosphino)ferrocene (5.13 g, 9.2 mmol) were then added. The resulting mixture was stirred and heated to 100° C. under a nitrogen atmosphere. The reaction was strongly exothermic once the internal temperature had reached >85° C., after 10 minutes the reaction stopped foaming. The internal reaction temperature reached reflux (~100° C.) and the reaction was stirred for 20 hours. The reaction was then cooled to 25° C. Ethyl acetate (2.5 L) and water (2.5 L) were added then this was filtered through a pad of celite. The aqueous layer was separated and the organic layer was washed with 50% brine/water (2.5 L), dried (magnesium sulphate), filtered and the solvent removed in vacuo. The crude product was then chromatographed on silica (5 Kg of Merck lichro prep silica 15-25 μm, 200 mm diameter column), eluting with a solvent gradient of 0-20% ethylacetate/isohexane. Pure fractions were evaporated to dryness to afford 2-fluoro-4-(4,4,5,5-tetramethyl-1,3,2-dioxaborolan-2-yl)phenol (348 g) as a yellow solid, proton NMR strength indicated 80% pure (therefore 278 g, 89%). The material was used crude in the next stage.

$^1$H NMR (400.132 MHz, CDCl$_3$) δ 1.33 (12H, s), 5.38 (1H, s), 6.98 (1H, t), 7.47-7.51 (2H, m)

m/z (ES−) (M−H)−=237

Intermediate 31-5: 6-(3-Fluoro-4-hydroxyphenyl)-3,5-dimethylpyrazine-2-carboxamide

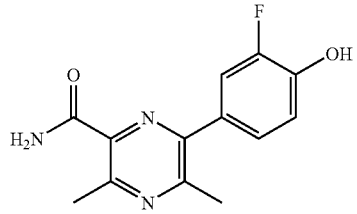

A suspension of 2-fluoro-4-(4,4,5,5-tetramethyl-1,3,2-dioxaborolan-2-yl)phenol (Intermediate 31-4; 348 g, 1169 mmol) (80% strength by proton NMR), 6-chloro-3,5-dimethylpyrazine-2-carboxamide (217 g, 1169 mmol) and potassium phosphate tribasic (298 g, 1403 mmol) in DME (3.6 L), ethanol (0.9 L) and water (1.8 L) was stirred. The mixture was degassed with nitrogen for 30 minutes at 30° C. Dichloro[1,1'-bis(diphenylphosphino)ferrocene]palladium(II) dichloromethane adduct (8.60 g, 10.5 mmol) was then added to the suspension. The reaction was further degassed for 10 minutes before being heated to 80° C., stirred for 4 hours. The reaction was cooled to 25° C. The solvents were then removed in vacuo until a slurry in water remained. A solution of citric acid (640 g) in water (6.0 L) was then added slowly with stirring. The suspension was filtered, washed with water (2×2.5 L), MTBE (2.5 L), sucked dry on the sinter and then dried at 65° C. in a vacuum over for 48 hours. Gave 6-(3-fluoro-4-hydroxyphenyl)-3,5-dimethylpyrazine-2-carboxamide (295 g, 97%) as a light brown solid.

$^1$H NMR (400.132 MHz, DMSO) δ 2.66 (3H, s), 2.78 (3H, s), 7.11 (1H, t), 7.47 (1H, d), 7.65 (1H, s), 7.70 (1H, d), 8.09 (1H, s), 10.24 (1H, s)

m/z (ES+) (M+H)+=262

Intermediate 31-6: [4-(6-Carbamoyl-3,5-dimethylpyrazin-2-yl)-2-fluorophenyl]trifluoromethanesulfonate

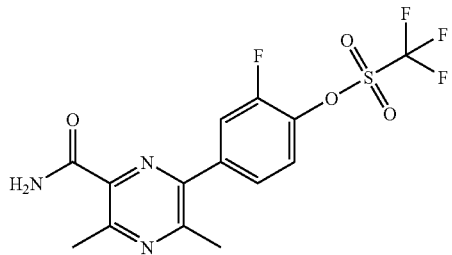

Potassium carbonate (468 g, 3387 mmol) was added in one go to a stirred mixture of 6-(3-fluoro-4-hydroxyphenyl)-3,5-dimethylpyrazine-2-carboxamide (Intermediate 31-5; 295 g, 1129 mmol) and N-phenylbis(trifluoromethanesulphonimide) (403 g, 1129 mmol) in THF (3.0 L), under a nitrogen atmosphere, at 25° C. The reaction was stirred at 25° C. for 20 hours. The reaction was filtered through a celite pad, washing through with ethyl acetate (5.0 L). The solvents were removed in vacuo. The crude product was dissolved in dichloromethane and then chromatographed on silica (5 Kg of Merck lichro prep silica 15-25 μm, 200 mm diameter column), eluting with a solvent mixture of 40% ethylacetate/isohexane. Pure fractions were evaporated to dryness to afford [4-(6-carbamoyl-3,5-dimethylpyrazin-2-yl)-2-fluorophenyl]trifluoromethanesulfonate (406 g, 91%) as a white solid.

$^1$H NMR (400.132 MHz, DMSO) δ 2.62 (3H, s), 2.76 (3H, s), 7.63 (1H, s), 7.77-7.85 (2H, m), 8.09 (1H, d), 8.12 (1H, s)

m/z (ES+) (M+H)+=394

Intermediate 31-7: Methyl 2-[4-[4-(6-carbamoyl-3,5-dimethylpyrazin-2-yl)-2-fluorophenyl]-3-chlorophenyl]acetate

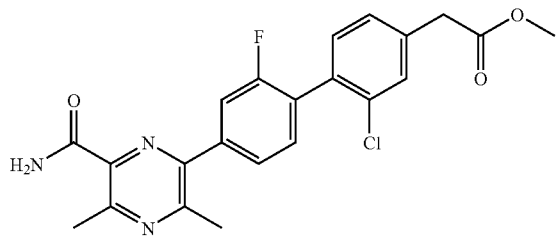

Dichloro[1,1'-bis(diphenylphosphino)ferrocene]palladium(II) dichloromethane adduct (68.2 g, 83.5 mmol) was added in one go to a stirred mixture, which had been degassed for 30 minutes with nitrogen, of 4-(6-carbamoyl-3,5-dimethylpyrazin-2-yl)-2-fluorophenyl trifluoromethanesulfonate (Intermediate 31-6; 730 g, 1856 mmol), methyl 2-(3-chloro-4-(4,4,5,5-tetramethyl-1,3,2-dioxaborolan-2-yl)phenyl)acetate (Intermediate 31-3; 1164 g, 1948 mmol) (52% strength by proton NMR), tripotassium phosphate (690 g, 3248 mmol) and lithium chloride (138 g, 3248 mmol) in DME (5 L), methanol (2.5 L) and water (2.5 L) at 20° C. The reaction was heated to reflux and stirred under a nitrogen atmosphere overnight. The reaction was cooled to room temperature. The organic layer was filtered through a glass sinter. Ethyl acetate (10.0 L) and 30% brine/water (5.0 L) were added. The aqueous layer was separated and extracted with ethyl acetate (5.0 L), the organic layers were combined, washed with 50% brine/water (10.0 L), dried (magnesium sulphate), filtered and the solvents removed in vacuo. The crude product was dissolved in dichloromethane and then chromatographed on silica (5 Kg of Merck lichro prep silica 15-25 µm, 200 mm diameter column), eluting with a solvent gradient of 0-70% ethylacetate/isohexane. Pure fractions were evaporated to dryness to afford methyl 2-[4-[4-(6-carbamoyl-3,5-dimethylpyrazin-2-yl)-2-fluorophenyl]-3-chlorophenyl]acetate (389 g, 49%) as a white solid.

$^1$H NMR (400.132 MHz, DMSO) δ 2.68 (3H, s), 2.79 (3H, s), 3.68 (3H, s), 3.84 (2H, s), 7.39 (1H, d), 7.46 (1H, d), 7.52 (1H, t), 7.58 (1H, s), 7.63 (1H, brs), 7.71 (1H, d), 7.80 (1H, d), 8.11 (1H, brs) m/z (ES+) (M+H)+=428

Intermediate 31-8: Methyl 2-[4-[4-(6-carbamoyl-3,5-dimethylpyrazin-2-yl)-2-fluorophenyl]-3-chlorophenyl]-3-hydroxypropanoate

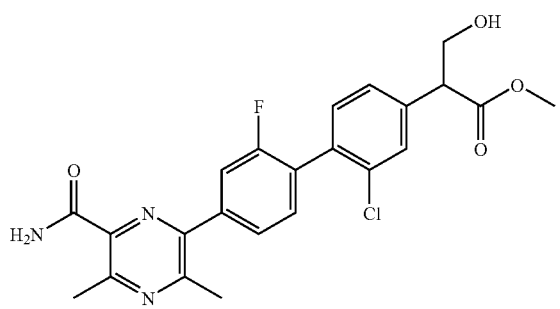

A stirred solution of methyl 2-(4'-(6-carbamoyl-3,5-dimethylpyrazin-2-yl)-2-chloro-2'-fluorobiphenyl-4-yl)acetate (Intermediate 31-7; 615 g, 1437 mmol) in DMF (2.5 L) was cooled to 15° C., under a nitrogen atmosphere. Potassium carbonate (214 g, 1545 mmol) was then added followed by paraformaldehyde (47.5 g, 1581 mmol). The reaction was stirred for 5 hours at 30° C. The reaction was then added to stirred water (25.0 L) and ethyl acetate (10.0 L). Concentrated hydrochloric acid (430 ml) was then added slowly with stirring. The aqueous layer was separated and extracted with ethyl acetate (7.5 L). The organics were combined and washed with, 50% brine/water (10.0 L), dried (magnesium sulphate), filtered and the solvent was removed in vacuo. Gave methyl 2-[4-[4-(6-carbamoyl-3,5-dimethylpyrazin-2-yl)-2-fluorophenyl]-3-chlorophenyl]-3-hydroxypropanoate (762 g) as a yellow gum, 64% by LCMS (therefore 488 g, 74% yield). The material was used crude in the next stage.
m/z (ES+) (M+H)+=458, 460

Intermediate 31-9: Methyl 2-[4-[4-(6-carbamoyl-3,5-dimethylpyrazin-2-yl)-2-fluorophenyl]-3-chlorophenyl]prop-2-enoate

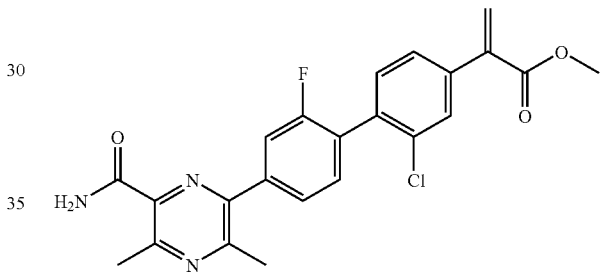

Methanesulfonyl chloride (0.145 L, 1865 mmol) was added over 5 minutes to a stirred solution of methyl 2-(4'-(6-carbamoyl-3,5-dimethylpyrazin-2-yl)-2-chloro-2'-fluorobiphenyl-4-yl)-3-hydroxypropanoate (Intermediate 31-8; 488 g, 1065 mmol) and triethylamine (0.520 L, 3730 mmol) in tetrahydrofuran (5.0 L) at 10° C. The reaction was heated to 50° C. and left stirring for 2 hours. The reaction was then cooled to 20° C. The mixture was diluted with ethyl acetate (10.0 L), then water (3.0 L) was added. Saturated aqueous ammonium chloride solution (4.1 L) was added. The organic layer was separated and the aqueous layer extracted with ethyl acetate (2.5 L). The organics were combined, washed with 50% brine/water (5.0 L), dried (magnesium sulphate), filtered and the solvent removed in vacuo. The crude product was dissolved in dichloromethane and then chromatographed on silica (5 Kg of Merck lichro prep silica 15-25 µm, 200 mm diameter column), eluting with a solvent gradient of 0-70% ethylacetate/isohexane. Pure fractions were evaporated to dryness to afford methyl 2-[4-[4-(6-carbamoyl-3,5-dimethylpyrazin-2-yl)-2-fluorophenyl]-3-chlorophenyl]prop-2-enoate (188 g, 40%) as a white solid.

$^1$H NMR (400.132 MHz, DMSO) δ 2.73 (3H, s), 2.84 (3H, s), 3.86 (3H, s), 6.29 (1H, s), 6.46 (1H, s), 7.55-7.62 (3H, m), 7.70 (1H, s), 7.76 (1H, d), 7.77-7.80 (1H, m), 7.86-7.90 (1H, m), 8.18 (1H, s)
m/z (ES+) (M+H)+=440, 442

Intermediate 31-10: 2-[4-[4-(6-Carbamoyl-3,5-dimethylpyrazin-2-0)-2-fluorophenyl]-3-chlorophenyl]prop-2-enoic acid

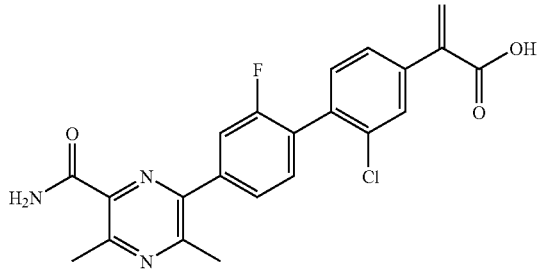

Potassium hydroxide (flakes) (232 g, 4137 mmol) was added to a suspension of methyl 2-[4-[4-(6-carbamoyl-3,5-dimethylpyrazin-2-yl)-2-fluorophenyl]-3-chlorophenyl]prop-2-enoate (Intermediate 31-9; 364 g, 827 mmol) in tert-butanol (4.3 L). The reaction was stirred for 4 hours at 30° C. The reaction was poured into stirring saturated citric acid solution (3.6 L), the resulting suspension (~pH 5) was reduced in vacuo until only the aqueous remained. Ethyl acetate (700 mL) was added and the two phase mixture stirred for 1 hour at 20° C. The white solid was filtered off, washed with water (2×2.5 L) followed by acetonitrile (2.0 L), sucked dry on the sinter then in a vacuum oven at 65° C. overnight. Gave 2-[4-[4-(6-carbamoyl-3,5-dimethylpyrazin-2-yl)-2-fluorophenyl]-3-chlorophenyl]prop-2-enoic acid (265 g, 75%) a yellow solid.

$^1$H NMR (400.132 MHz, DMSO) δ 2.67 (3H, s), 2.77 (3H, s), 6.12 (1H, s), 6.33 (1H, s), 7.47-7.54 (3H, m), 7.63 (1H, s), 7.69-7.73 (2H, m), 7.79-7.83 (1H, m), 8.11 (1H, s), COOH not seen m/z (ES−) (M−H)−=424, 426

The invention claimed is:
1. A compound of formula (I), or a pharmaceutically-acceptable salt thereof,

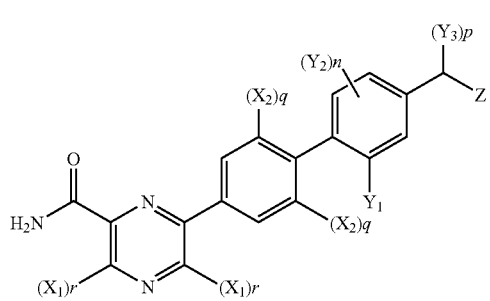

wherein
each r is 1;
each $X_1$ is independently linear (1-3C)alkyl;
each q is independently 0 or 1;
each $X_2$ is independently fluoro;
$Y_1$ is chloro;
n is 0;
p is 0 or 1;
$Y_3$ (1-3C)alkyl; and
Z is carboxy.

2. The compound of claim 1, wherein the compound is 2-(4'-(6-carbamoyl-3,5-dimethylpyrazin-2-yl)-2-chloro-2'-fluorobiphenyl-4-yl)propanoic acid or a pharmaceutically acceptable salt thereof.

3. The compound of claim 2, wherein the compound is (S)-2-(4'-(6-carbamoyl-3,5-dimethylpyrazin-2-yl)-2-chloro-2'-fluorobiphenyl-4-yl)propanoic acid or a pharmaceutically acceptable salt thereof.

4. A pharmaceutical composition which comprises a compound of claim 3, in association with a pharmaceutically acceptable excipient or carrier.

5. The compound of claim 2, wherein the compound is (R)-2-(4'-(6-carbamoyl-3,5-dimethylpyrazin-2-yl)-2-chloro-2'-fluorobiphenyl-4-yl)propanoic acid or a pharmaceutically acceptable salt thereof.

6. A pharmaceutical composition which comprises a compound of claim 5, in association with a pharmaceutically acceptable excipient or carrier.

7. The compound of claim 2, wherein the compound is 2-(4'-(6-carbamoyl-3,5-dimethylpyrazin-2-yl)-2-chloro-2'-fluorobiphenyl-4-yl)propanoic acid.

8. A pharmaceutical composition which comprises a compound of claim 7, in association with a pharmaceutically acceptable excipient or carrier.

9. The compound of claim 2, wherein the compound is (S)-2-(4'-(6-carbamoyl-3,5-dimethylpyrazin-2-yl)-2-chloro-2'-fluorobiphenyl-4-yl)propanoic acid.

10. A pharmaceutical composition which comprises a compound of claim 9, in association with a pharmaceutically acceptable excipient or carrier.

11. The compound of claim 2, wherein the compound is (R)-2-(4'-(6-carbamoyl-3,5-dimethylpyrazin-2-yl)-2-chloro-2'-fluorobiphenyl-4-yl)propanoic acid.

12. A pharmaceutical composition which comprises a compound of claim 2, in association with a pharmaceutically acceptable excipient or carrier.

13. A pharmaceutical composition which comprises a compound of claim 12, in association with a pharmaceutically acceptable excipient or carrier.

* * * * *